United States Patent [19]

Hibino et al.

[11] Patent Number: 4,855,819
[45] Date of Patent: Aug. 8, 1989

[54] ENDOSCOPE IMAGING SYSTEM FOR USE WITH MULTIPLE COLOR IMAGING SYSTEMS

[75] Inventors: Hiroki Hibino, Hachioji; Kenji Kimura, Tachikawa; Masahide Kanno, Hachioji; Toshiaki Nishikori, Sagamihara; Jun Yoshinaga, Hino; Atsushi Kidawara, Tachikawa; Hisao Yabe, Hachioji; Shinichi Katou, Oume; Koji Takamura, Hachioji; Takeaki Nakamura, Hino, all of Japan

[73] Assignee: Olympus Optical Co., Ltd., Tokyo, Japan

[21] Appl. No.: 150,255

[22] Filed: Jan. 29, 1988

[30] Foreign Application Priority Data

Jan. 31, 1987 [JP] Japan ................................. 62-21459
Jan. 31, 1987 [JP] Japan ................................. 62-21461
Mar. 10, 1987 [JP] Japan ................................. 62-54599
Mar. 17, 1987 [JP] Japan ................................. 62-61688

[51] Int. Cl.$^4$ .......................................... H04N 7/18
[52] U.S. Cl. .................................... 358/98; 128/6
[58] Field of Search .................. 358/98, 901; 128/4, 128/6, 303.15; 350/96.26, 96.27; 250/227

[56] References Cited

U.S. PATENT DOCUMENTS

| | | | |
|---|---|---|---|
| 4,407,272 | 10/1983 | Yamaguchi | 128/6 |
| 4,621,284 | 11/1986 | Nishioka et al. | 358/98 |
| 4,638,353 | 1/1987 | Nagasaki et al. | 358/98 |
| 4,646,724 | 3/1987 | Sato et al. | 128/6 |
| 4,653,478 | 3/1987 | Nagasaki et al. | 358/98 |
| 4,729,018 | 3/1988 | Watanabe et al. | 128/6 |
| 4,740,837 | 4/1988 | Yamagisawa et al. | 128/6 |

Primary Examiner—James J. Groody
Assistant Examiner—John K. Peng
Attorney, Agent, or Firm—Armstrong, Nikaido, Marmelstein, Kubovcik & Murray

[57] ABSTRACT

A system comprising a frame sequential type color imaging device, a color imaging device provided with a color filter, an illuminating light outputting device which can output illuminating lights corresponding to these different color imaging devices, a signal processing device processing the signals corresponding to the respective color imaging devices and a color monitor displaying the processed color video signals so that any color imaging device can be used.

63 Claims, 41 Drawing Sheets

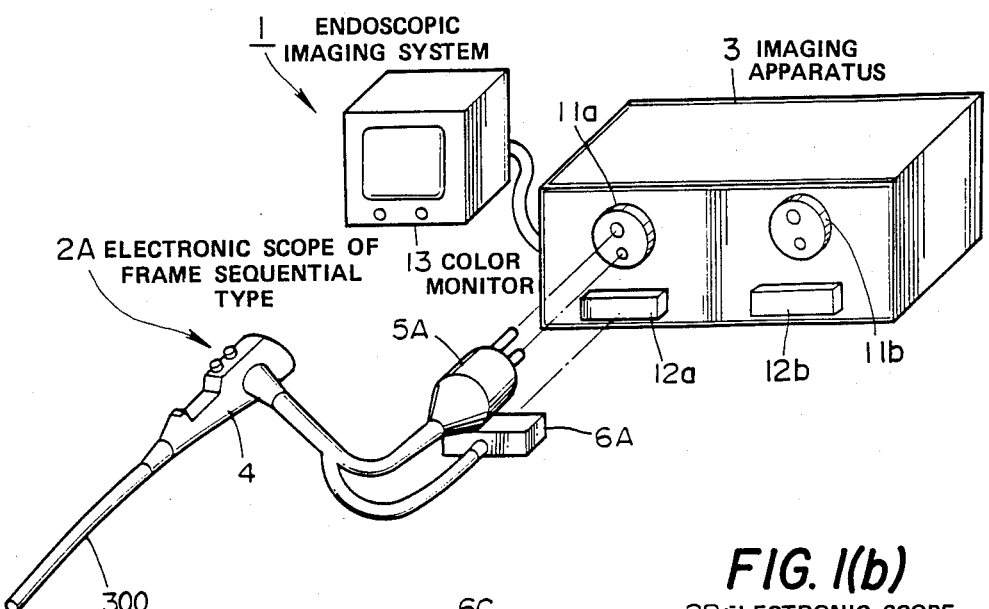
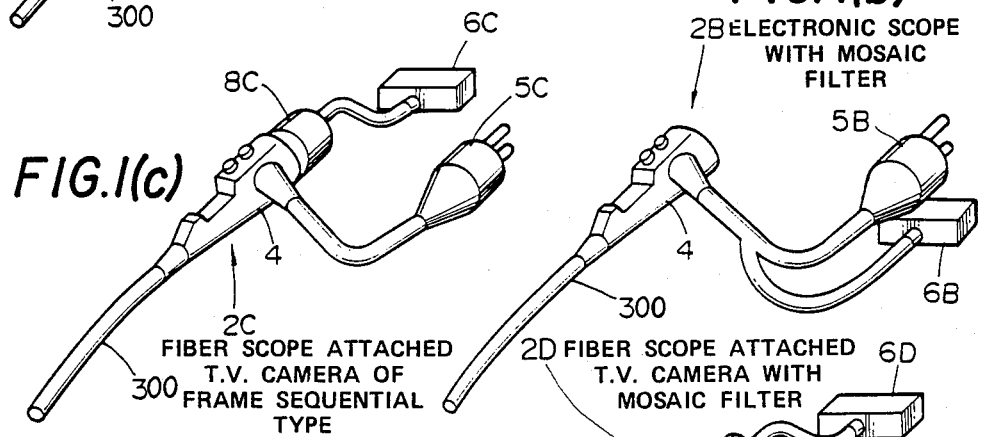
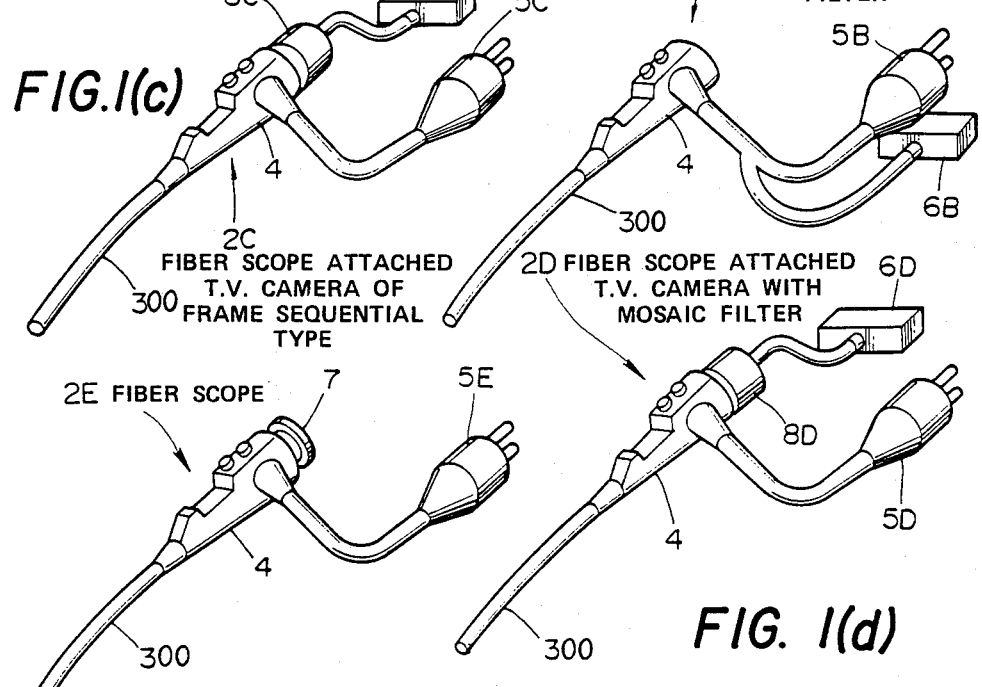
FIG. 1(a), FIG. 1(b), FIG. 1(c), FIG. 1(d), FIG. 1(e)

FIG.30(a)
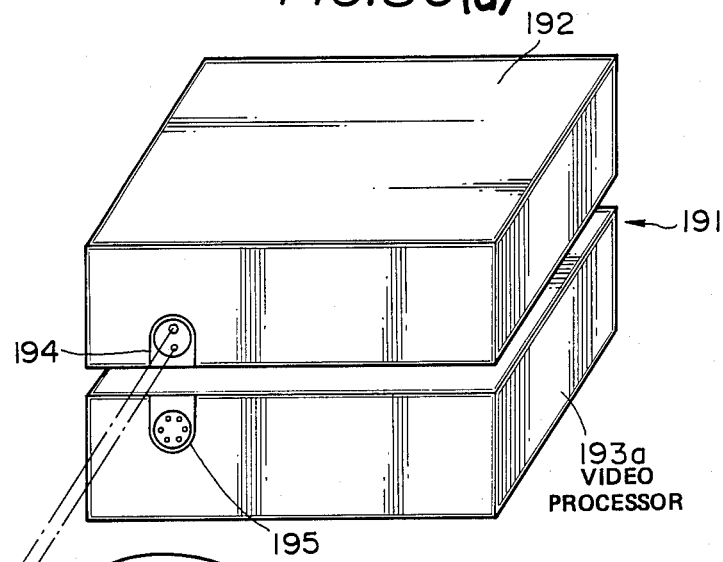
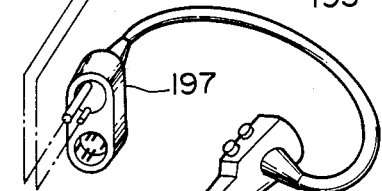
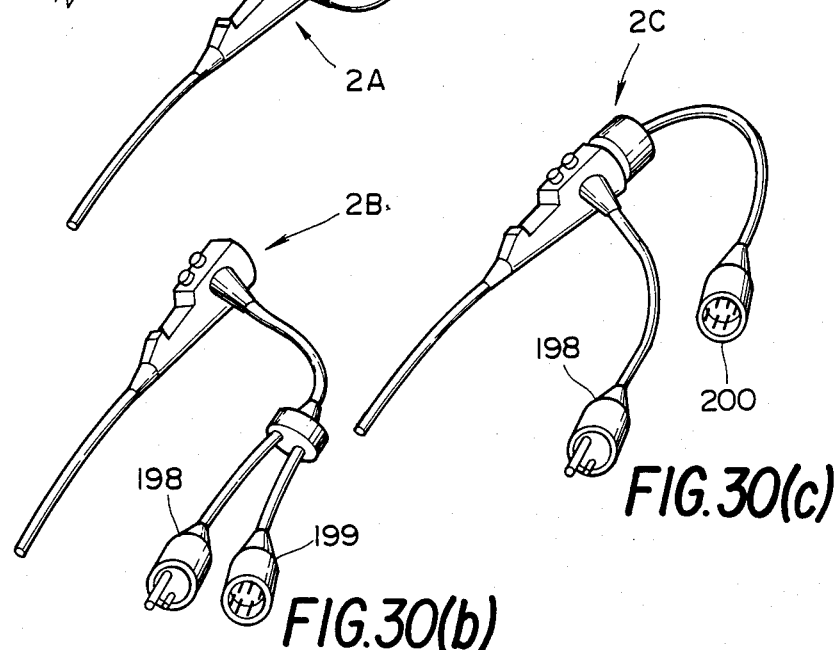
FIG.30(b)
FIG.30(c)

254
253
252a IMAGING AP.
252b MOSAIC TYPE PRI-PROCESSOR UNIT
13 COLOR MONITOR 13
71
254
252a
72

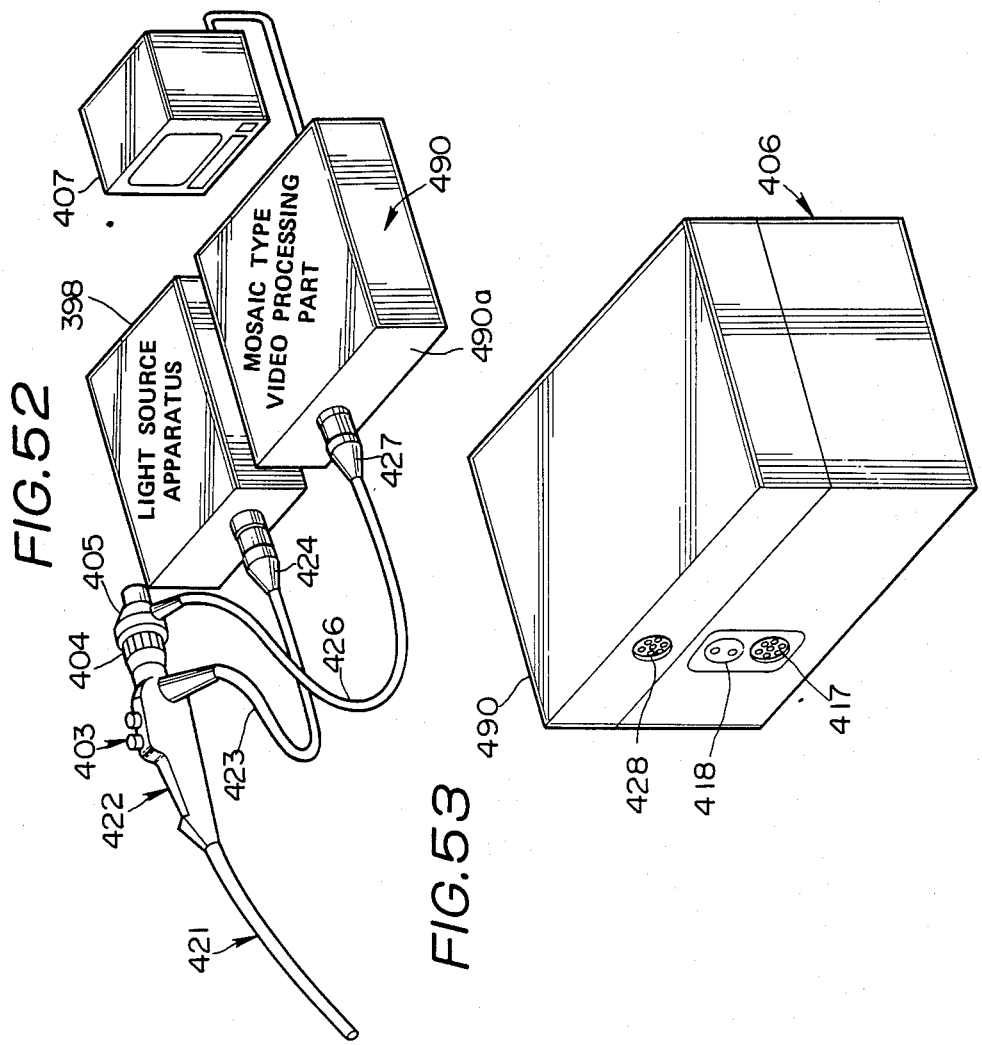

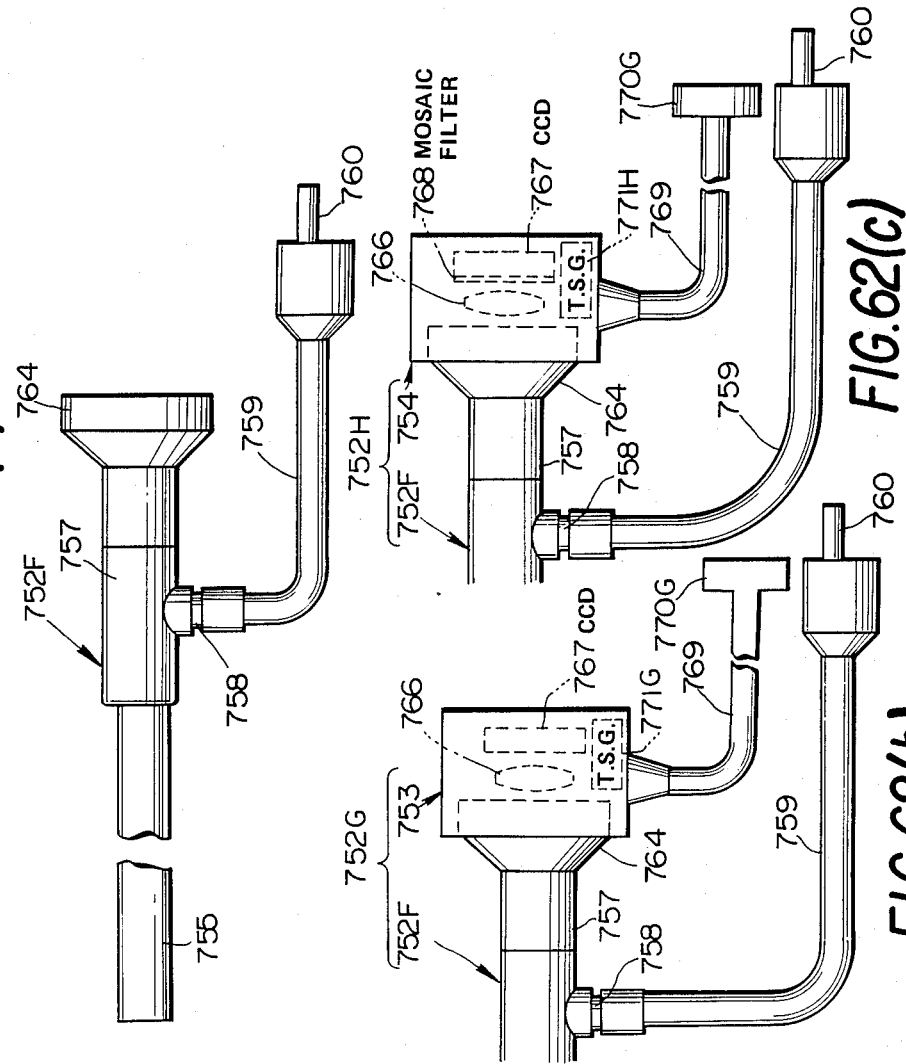

ENDOSCOPE IMAGING SYSTEM FOR USE WITH MULTIPLE COLOR IMAGING SYSTEMS

BACKGROUND OF THE INVENTION

Field of the Invention and Related Art Statement

This invention relates to an endoscope imaging system which can be used also for endoscopes of different color imaging systems.

Recently, instead of an optical endoscope (for example, a fiber scope) wherein an optical image formed by an objective in the tip part of an insertable part is transmitted to the base side by an image guide formed of a fiber bundle, there has come to be practically used an electronic endoscope (which shall be called an electronic endoscope or electronic scope hereinafter) wherein an optical image formed by an objective is photoelectrically converted to an electric signal, is transmitted to the base side and can be displayed by a color monitor through a video processor.

The above mentioned electronic scope now used for upper and lower digesting tubes is of a diameter of 10 mm. However, for example, an endoscope for the bronchus is usually required to be of a diameter less than about 5 mm. In order to realize an electronic scope for the bronchus (thin diameter), an imaging device of a small number of pixels must be used.

In case the above mentioned number of pixels is small, in order to prevent the reduction of the resolution, a frame sequential type color imaging system, wherein a object is illuminated by a frame sequential system with lights of respective wavelengths of red, blue and green and is imaged frame sequentially under the illumination and the images are composed and color-displayed, is more advantageous than a color-imaging system wherein a color mosaic filter is used. On the other hand, in case the number of pixels, which can be made thick in the diameter, is large and a sufficient resolution can be obtained, a mosaic type color imaging system using a mosaic filter will be adopted.

In the case of the above mentioned electronic scope, a video processor wherein a signal is processed to be a video signal which can be displayed by a color monitor is used in addition to a light source apparatus used in a fiber scope.

However, a prior art example is exclusively used for only a fiber scope or electronic scope, and a light source apparatus for the fiber scope or a video processor and light source apparatus for the electronic scope, can not be commonly used.

In the electronic scope, too, it is necessary to have different signal processing in a different color imaging system and a respective video processor and light source apparatus have been required.

Therefore, as disclosed, for example, in the gazette of a Japanese patent laid open No. 243625/1985, there is suggested a system wherein an imaging adapter is connected to a fiber scope to display an image on a color monitor picture surface.

In the above mentioned prior art example, in case the imaging adapter is connected, an electronic scope making a frame sequential system color imaging can be formed and, in case it is connected to a control apparatus (integrating a video processor and light source apparatus), a color displaying by frame sequential imaging can be made.

In the above mentioned system, there is a defect that a color mosaic type electronic scope can not be connected to be used. Also, .as the system can be applied only to the above mentioned frame sequential system, when a moving object is to be image, it can not be selected and used, though it is desirable to use it by fitting a color mosaic type electronic scope.

OBJECTS AND SUMMARY OF THE INVENTION

An object of the present invention is to provide an endoscope imaging system which can be used also for color imaging device of different color imaging systems.

Another object of the present invention is to provide an endoscope imaging system which can adopt different color imaging systems to be use.

In the present invention, there are provided a color imaging device of different systems, an illuminating light output device corresponding to the respective color imaging device, a signal processing device corresponding to the respective color imaging device and a monitor device displaying color video signals produced by the respective signal processing device so that a color displaying may be made by the monitor for any color imaging device.

BRIEF DESCRIPTION OF THE DRAWINGS

FIGS. 1 go 8 relate to the first embodiment of the present invention.

FIG. 1a–1e are a perspective view showing the entire system of the first embodiment.

FIG. 30a–30c are a perspective view showing the appearance of the ninth embodiment of the present invention.

FIG. 52 is a perspective view showing that a mosaic type endoscope apparatus can be used as separated in the fourteenth embodiment.

FIG. 53 is a perspective view showing a control apparatus (imaging apparatus) in the fifteenth embodiment of the present invention.

FIG. 53 is a formation diagram of a system of the sixteenth embodiment of the present invention.

FIG. 62a–62c are a side view showing a rigid endoscope which can be used for the system, for example, of the first embodiment and a rigid endoscope fitted with an externally fitted camera.

DETAILED DESCRIPTION OF PREFERRED EMBODIMENTS

Figure 2:
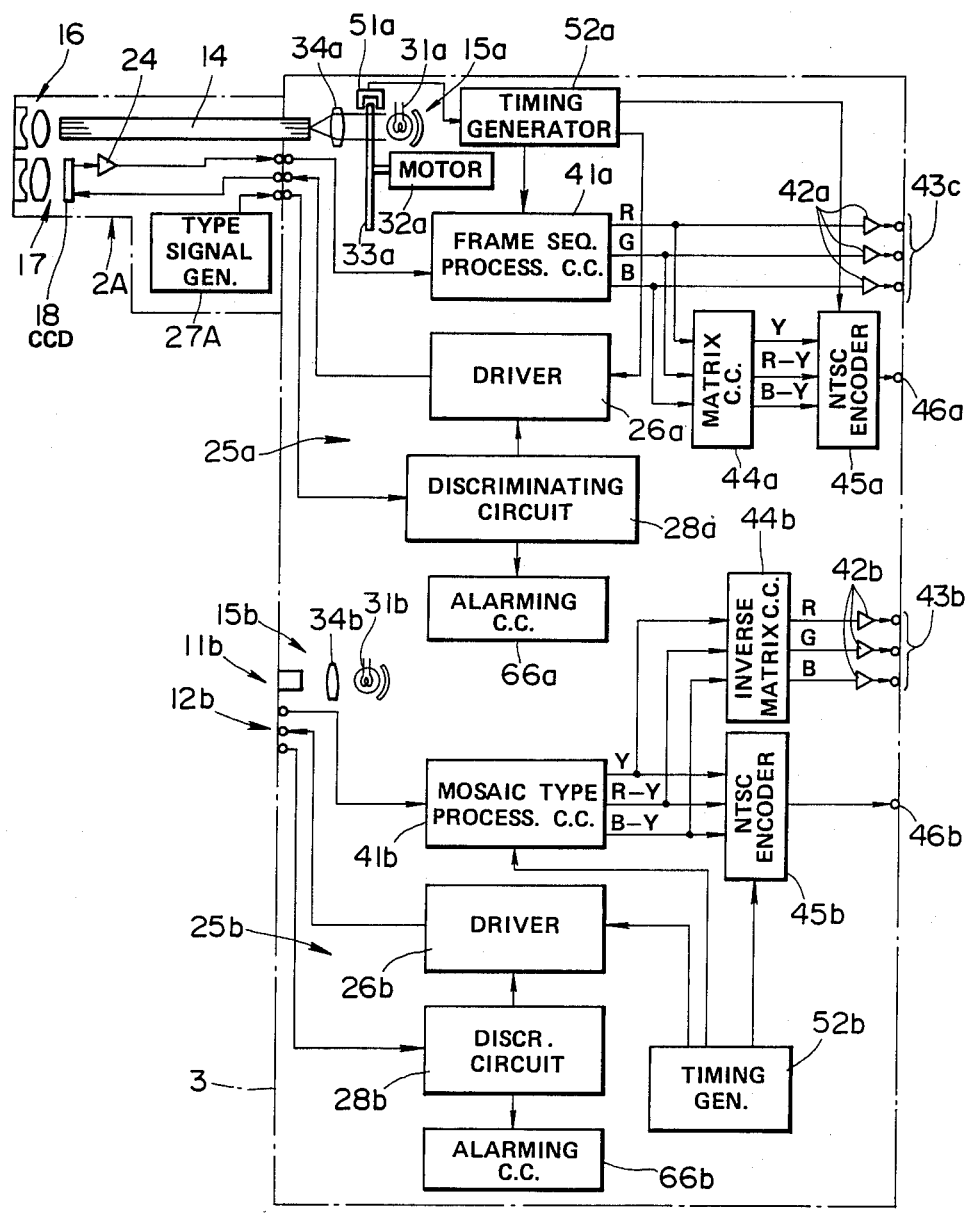
FIG. 2 is a block diagram showing the formation of an imaging apparatus in the first embodiment.
Figure 3:
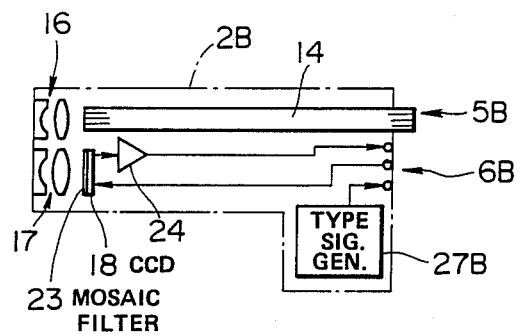
FIG. 3 is a schematic formation view of an electronic scope using a color mosaic filter.
Figure 4:
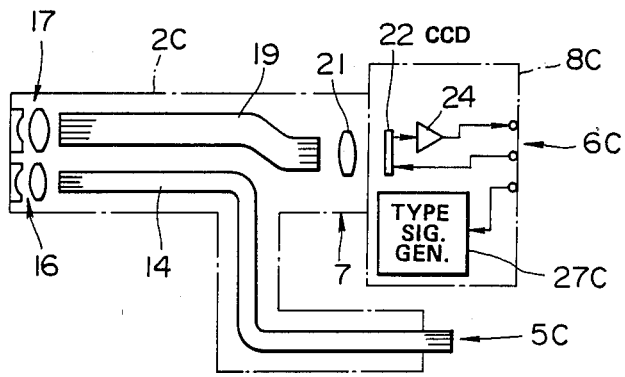
FIG. 4 is a schematic formation view of a fiber scope fitted with a frame sequential type TV camera.
Figure 5:
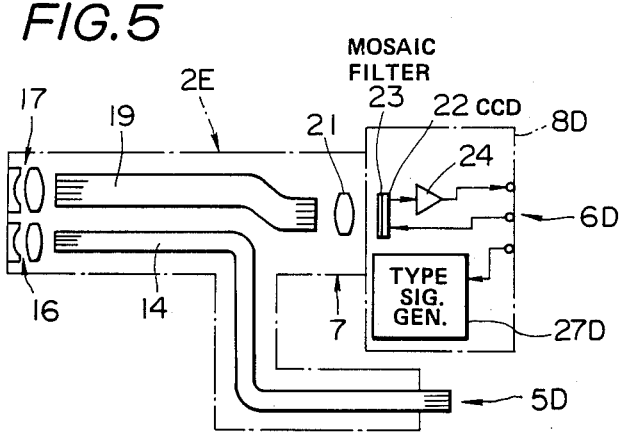
FIG. 5 is a schematic formation view of a fiber scope fitted with a TV camera using a color mosaic filter.
Figure 6:
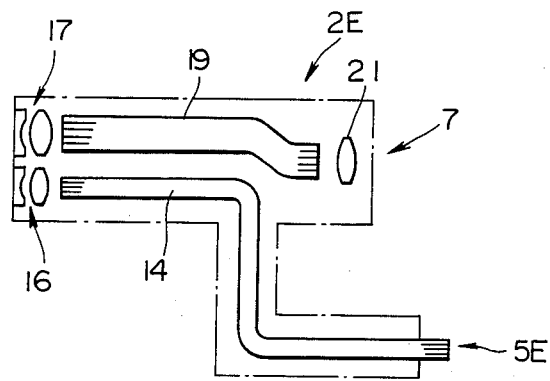
FIG. 6 is a schematic formation view of a fiber scope.

As shown in FIG. 1, the endoscope imaging system 1 of the first embodiment has an imaging apparatus 3 which can be connected with any of various scopes (endoscopes) 2A, 2B, 2C, 2D and 2E. The scopes are of five kinds as shown in FIG. 1, that is, a frame sequential type electronic scope 2A, an electronic scope using a color mosaic filter 2B (which shall be mentioned as a color mosaic type electronic scope or an electronic scope having a mosaic filter hereinafter). A fiber scope externally fitted with a frame sequential type TV camera (which shall be mentioned as a fiber scope fitted with a field sequential type TV camera) 2C. A fiber scope externally fitted with a color mosaic type TV camera 9 which shall be mentioned as a fiber scope fitted with a (color) mosaic type TV camera) 2D and a fiber scope 2E. Each of the scopes 2A, 2B, 2C, 2D and 2E has an elongate insertable part 300, has an operating part 4 formed on the rear end side of the insertable part 300, has a universal cord extended out of this operating part and has each of light source connectors 5A, 5B, 5C, 5D and 5E provided at the tip. In this case, in the frame sequential type electronic scope 2A and color mosaic type electronic scope 2B, not only light source connectors 5A and 5B but also signal connectors 6A and 6B are provided on the tip sides of the above mentioned universal cords. In the fiber scope 2C fitted with a frame sequential type TV camera and fiber scope 2D fitted with a color mosaic type TV camera, a frame sequential type TV camera 8C and color mosaic type TV camera 8D are respectively fitted to the eyepiece part 7 of the fiber scope 2E. Two sets of connector receptacles are provided, for example, on the front surface of a housing of an imaging apparatus 3 so that the respective scopes 2 may be set in a usable state by connecting the connectors 5A, 6A; 5B, 6B; 5C, 6C; 5D, 6D; 5E of these respective scopes 2A, 2B, 2C, 2D and 2E (represented by the reference numeral 2 in case they are common to all these scopes). These connector receptacles consist of a frame sequential type light source connector receptacle 11a, frame sequential type signal connector 12a, white light source connector receptacle 11b and color mosaic type signal connector 12b. The light source connectors 5A and 5C of the same form with each other of the frame sequential type electronic scope 2AQ and the fiber scope 2C fitted with the frame sequential type TV camera (these two scopes 2A and 2C shall be mentioned also as frame sequential type scopes) are of such forms as can be connected respectively to the frame sequential type light source connector receptacle 11a. The respective signal connectors 6A and 6C of the same forms with each other of the frame sequential type electronic scope 2A and the fiber scope 2C fitted with the frame sequential type TV camera, that is, the frame sequential type scopes 2A and 2C are of such forms as can be connected to the frame sequential type signal connector 12a adjacent to the lower side of the above mentioned frame sequential type light source connector receptacle 12a.

On the other hand, so that the light source connector 5B of the color mosaic type electronic scope 2B, the light source connector 5D of the fiber scope 2D fitted with the color mosaic type TV camera (these two scopes 2B and 2D shall be mentioned also as mosaic type scopes) and the light source connector 5E of the fiber scope 2E may be respectively connected to the white light source connector receptacle 11b, these connectors 5B, 5D and 5E are made in the same form. Also, so that the signal connector 6B of the color mosaic type electronic scope 2B and the signal connector 6D of the fiber scope 2D fitted with color mosaic type TV camera may be connected to the color mosaic type signal connector 12b adjacent to the lower side of this white light source connector receptacle 11b, these connectors 6B and 6D are made in the same form.

In case the above mentioned fiber scope 2E is connected and used, the observation is made by a naked eye. When the other scope 2A, 2B, 2C or 2D is used, the imaged image can be color-displayed by a color monitor 13 connected to the signal output end of the imaging apparatus 3.

In this embodiment, the light source connectors 5A, 5B, 5C, 5D and 5E in the respective scopes 2 are provided with light guide connectors and air and water feeding connectors which can be connected to the connector receptacles 11a and 11b.

The internal formations of the above mentioned respective scopes 2A, 2B, 2C, 2D and 2E are shown respectively in FIGS. 2, 3, 4, 5 and 6. A light guide 14 transmitting an illuminating light is inserted through each scope 2 so that the illuminating light fed from the light source part 15a or 15b within the imaging apparatus 3 to the entrance end surface may be transmitted to the exit end surface side to illuminate the object side in the front through a light distributing lens arranged in front of this exit end surface.

An image forming objective 17 is arranged in the tip part of the insertable part 300 of each scope 2. In the frame sequential type or color mosaic type electronic scope 2A or 2B, a CCD 18 is arranged in the focal plane of this objective 17. On the other hand, in the fiber scope 2E or the fiber scope 2C or 2D fitted with a TV camera 8C or 8D, the entrance end surface of the image guide 19 is arranged to be present in the focal plane of the objective 17.

An eyepiece 21 is arranged as opposed to the exit end surface of the above mentioned image guide 19. In the fiber scope 2E, an observation can be made with a naked eye brought close to the eyepiece part 7.

On the other hand, in the fiber scope 2E fitted in the eyepiece part 7 with the frame sequential type TV camera 8C or color mosaic type TV camera 8D, a CCD 22 is arranged as opposed to the eyepiece 21 (through an image forming lens not illustrated). A color mosaic filter 23 is arranged on the front surface of the imaging surface of the CCD 18 or 22 used in the color mosaic type electronic scope 2B or color mosaic type TV camera 8D. The optical image formed on the imaging surface is photoelectrically converted by the CCD 18 or 22 forming an imaging means, is amplified by a preamplifier 24, in then transmitted to the signal connector 6 (representing 6A, 6B, 6C and 6D) side through a signal transmitting line and is input into a video processor 25a or 25b through the signal connector receptacle 12a or 12b to which the connector 6 is connected. Also, a CCD driving clock is applied from a driver 26a or 26b forming a video processor 25a or 25b to the CCD 18 or 22. Here, the video processor 25a represents the entire frame sequential type signal processing system. The video processor 25b represents the entire mosaic type signal processing system.

Type signal generating circuits 27A, 27B, 27C and 27D outputting scope discriminating type signals are provided in the scopes other than the fiber scope 2E1 and the type signal is discriminated by a discriminating circuit 28a or 28b within the imaging apparatus through the signal connector 6.

The imaging apparatus 3 to which any of the above mentioned scopes 2 can be connected contains two sets of light source parts 15a and 15b and two sets of video processors 25a and 25b as shown in FIG. 2.

One light source part 15a is of a frame sequential type. A white light of a light source lamp 31a is made of illuminating light of R, G and B through a rotary filter 33a rotated by a motor 32a, is then condensed by a condenser lens 34a and is fed to the entrance end surface of the light guide 14 fitted to the connector receptacle 11a.

The other light source part 15b is a white light source. A white light of a white lamp 31b is condensed by a condenser lens 34b, is led to a white light source connector receptacle 11b and is fed to the entrance end surface of a light guide 14 fitted to this connector receptacle 11b.

Now, one video processor 25a is for frame sequential type signal processing. The signal input into the signal input terminal of the frame sequential type signal connector receptacle 12a is input into a frame sequential type process circuit 41a and the signals respectively imaged under the illuminating lights of the respective wavelengths of R, G and B are output as color signals R, G and B. The above mentioned color signals R, G and B output three primary color signals R, G and B from three primary color signals R, G and B.

The above mentioned color signals R, G and B are transmitted through a matrix circuit 44a to produce a luminance signal Y and color difference signals R-Y and B-Y which are then input into an NTSC encoder 45a to be converted to a composite video signal of an NTSC system which is output out of an NTSC output end 46a.

A rotary position sensor 51a detecting the rotary position is provided in one place on the outer periphery of the rotary filter 33a forming the above mentioned frame sequential system light source part 15a. By its output, the timing of the clock of the timing generator 52a is synchronized with the rotation of the rotary filter 33a and the timing of the frame sequential type process circuit 41a is controlled by the output of this timing generator 52a.

Figure 7:
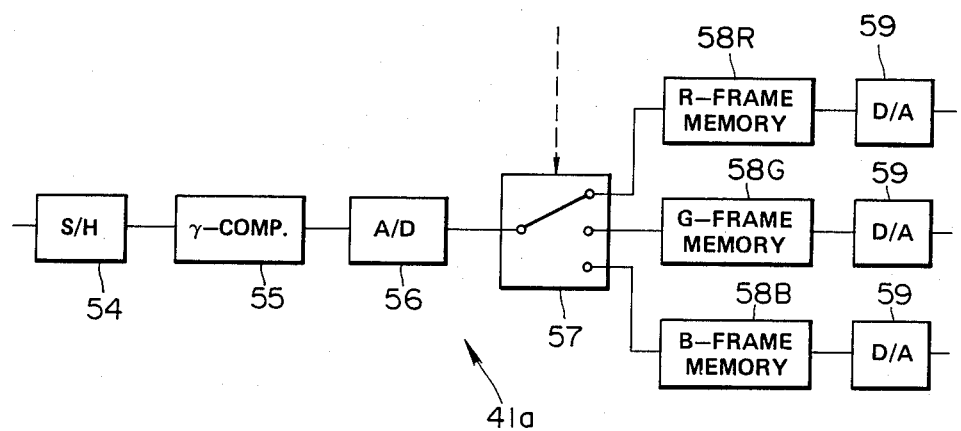
FIG. 7 is a block diagram showing the formation of a frame sequential process circuit.

This frame sequential type process circuit 41a is formed as shown for example, in FIG. 7.

That is to say, the signal input through a pre-amplifier is input into a sample holding circuit 54, is sample-held, is then γ-corrected in a γ-correcting circuit 55 and is converted to be in a digital amount in an A/D converter 56. Then, the signal imaged under the frame sequential illumination of R, G and B through a multiplexer 57 switched by the signal of the above mentioned timing generator 52a is written into an R-frame memory 58R, G-frame memory 58G and B-frame memory 58B. The signal data written into these respective frame memories 58R, 58G and 58B are read out simultaneously, are converted respectively to analogue color signals R, G and B by D/A converters 59 and are output to the above described matrix circuit 44a side.

On the other hand, the signal imaged by the CCD 18 or 22 through the color mosaic type signal connector 12b is input into a color mosaic type process circuit 41b to output a luminance signal Y, color difference signals R-Y and B-Y. These signals are input into an NTSC encoder 45b and converted to a composite video signal which is output from the NTSC output end 46b. Also, these signals are input into an inverse matrix circuit 44b and are converted to color signals R, G and B and three primary color signals R, G and B are output from three primary color output ends 43b respectively through buffers 42b forming drivers.

Figure 8:
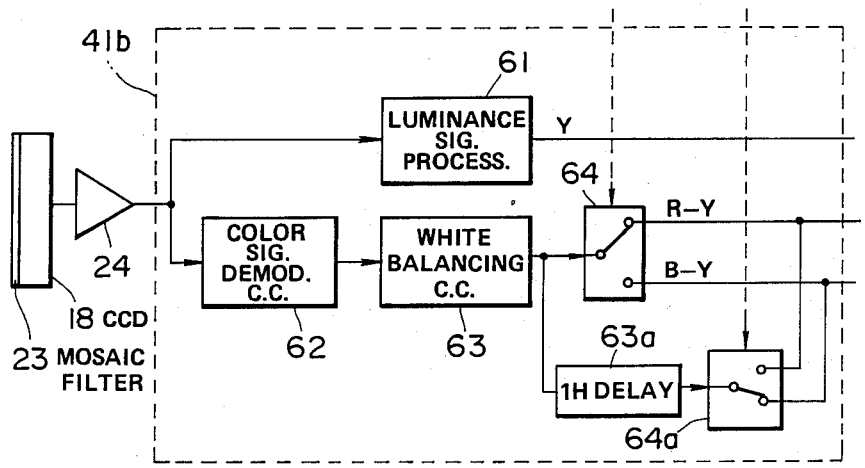
FIG. 8 is a block diagram showing the formation of a color mosaic type process circuit.

In the above mentioned color mosaic type process circuit 41b, for example, as shown in FIG. 8, the signal from the CCD 18 (or 22) amplified by a pre-amplifier 24 produces a luminance signal Y through a luminance signal processing circuit 61. The above mentioned signal is also input into a color signal demodulating circuit 62. Color difference signals R-Y and B-Y are produced in each horizontal line in time series and are white balance-compensated in a white balance circuit 63. One of the signals is input directly into an analogue switch 64 and the other is delayed by one horizontal line by a 1H delay line 63a and is input into an analogue switch 64a to obtain color signals R-Y and B-Y by a switching signal of a timing generator 52b.

The respective timing generator 52a and 52b apply signals respectively to the drivers 26a and 26b and the encoders 45a and 45b and control to process the signal synchronized with the driving pulse used to read out signals from the CCD 18 or 22. In this case, the above mentioned timing generator 52a is synchronized with the rotary filter 33 by the output of the rotary position sensor 51a. The above mentioned NTSC encoders 45a and 45b are formed to contain buffers.

Now, each of the type signal generating circuits 27A, 27B, 27C and 27D is formed, for example, by connecting a resistance or the like of a different resistance value between two terminals. On the other hand, the connected scope of any resistance value between the two terminals can be discriminated by using a comparator or the like in the discriminating circuits 28a and 28b.

For example, in case the signal connector 6B or 6D of the color mosaic type electronic scope 2B or the fiber scope 8D fitted with the color mosaic type TV camera is connected to the frame sequential type signal connector receptacle 12a, it will be discriminated that it is not of a resistance value for the frame sequential type, a warning circuit 66a will be operated by the discriminated signal and it will be made known to the user by a warning sound by a buzzer or a fickering by an ED.

Also, in case the connector 6A of the frame sequential type electronic scope 2A or the connector 6C of the fiber scope 2C fitted with the frame sequential type TV camera is connected to the color mosaic type signal connector receptacle 12b, it will be discriminated by the discriminating circuit 28b and will be warned by a warning circuit 66b.

On the other hand, when the connector 6A or 6C of the frame sequential type scope 2A or 2C is connected to the frame sequential type signal connector receptacle 12a, it will not be warned. (If the connection is right, it may be displayed by lighting an LED.) Likewise, if the connector 6B or 6D of the color mosaic type scope 2B or 2D is connected to the color mosaic type connector receptacle 12b, the warning circuit 66b will not operate. (It may be displayed by the lighting of the LED of a position or color different from the case of discriminating and warning that the connection is right.) Also, in case two signal connectors are simultaneously connected to both signal connector receptacle 12a and 12b, it may be warned. Also, a light source connector connection sensing means may be provided within the frame sequential type light source connector receptacle 11a so that, in case the connector 5E of the fiber scope 2E is connected, it may be made known to be a mis-connection. That is to say, it is possible to warn in case the connector 5E is connected to the connector receptacle 11a and no connector is connected to the signal connector receptacle 11a and 11b.

In the thus formed first embodiment, the frame sequential type scope light source part 15a and frame sequential type video processor 25a and the color mosaic type scope light source part 15b and color mosaic type video processor 25b are provided and the connecting means for the respective scopes are provided, even if any of the frame sequential type scopes 2A and 2C and color mosaic type scopes 2B and 2D is connected, the illuminating light feed and signal process corresponding to the connected scope can be made and the object image imaged by the connected scope can be color-displayed.

In case the fiber scope 2E is used, its light source connector 5E can be connected to the white light source connector receptacle 11b and thus a naked eye observation can be made.

On the other hand, in case a wrong scope is connected to two sets of connector receptacles 12a and 12b, the wrong connection can be sensed by the discriminating circuit 28a or 28b and can be warned by the warning circuit 66a or 66b.

Therefore, according to this first embodiment, when one imaging apparatus 3 is provided, a scope different in the color imaging system can be used and even the fiber scope 2E can be simultaneously used. In case a wrong connection is made, it will be warned. Therefore, the apparatus is convenient to use. It is apparent that, if the connector 6 and connector receptacle 12 are made in forms different between the frame sequential type and mosaic type, the mis-connection can be eliminated.

The signals processed for the above mentioned two color imaging systems are the same in the output type. That is to say, they are made to coincide with the three primary color outputs or NTSC system video signals and therefore the same color monitor 13 can be used. (This color monitor may input either three primary colors or NTSC system video signals.)

When the TV camera 8C or 8D is fitted to the fiber scope 2E, the imaged picture image will be displayed in the color monitor 13. In case the TV camera 8C or 8D is removed, this removed state may be displayed on the picture surface of the color monitor 13.

According to the system of this first embodiment, a color imaging system adapted to the use can be selectively used.

For example, in case a high resolution is required, by using the frame sequential type color imaging scope 2A or 2C, a high resolution color picture image can be displayed in the color monitor B.

On the other hand, in case of use near a moving position, if the frame sequential type color imaging scope 2B or 2D is used, a color imaged picture image having little color displacement can be obtained.

Figure 9A:
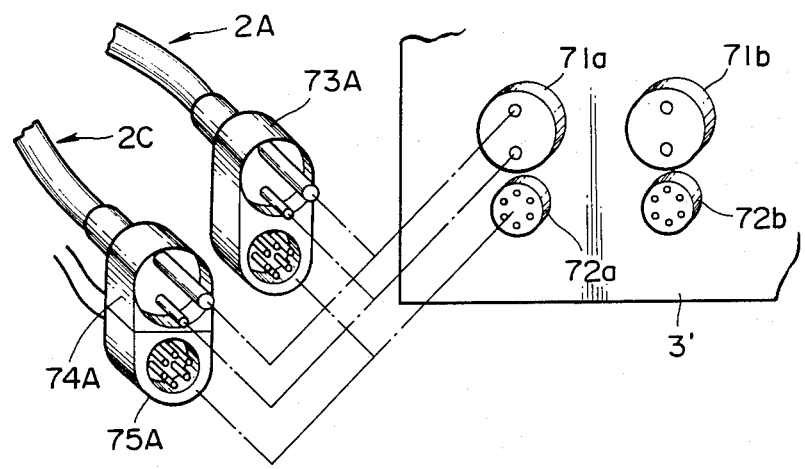
FIG. 9a–9b are a perspective view showing another embodiment of a light source and signal connector.
Figure 9B:
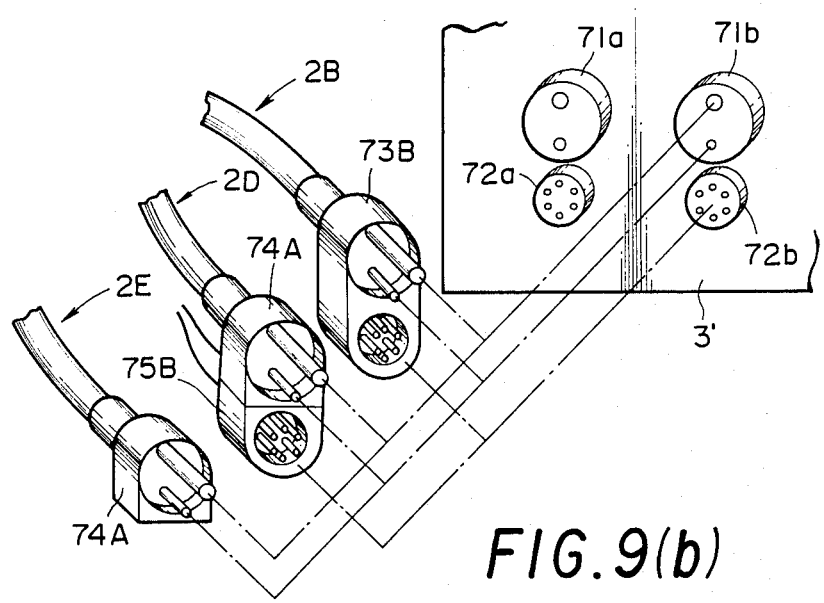

FIG. 9 shows modification of a connector and connector receptacle.

An imaging apparatus 3' is provided with a round frame sequential type light source connector receptacle 71a and signal connector receptacle 72a and white light source connector receptacle 71b and color mosaic type signal connector receptacle 72b as separated on a housing front surface or the like. Both connector receptacles 71a and 71b or 72a and 72b are of the same form with each other.

On the other hand, as shown in FIG. 9 (a), a frame sequential type scope 2A is provided with a connector 73A integrating a light source connector part and signal connector part so as to be connectable to a frame sequential type light source connector receptacle 71a and signal connector receptacle 72a.

In the same manner, as shown in FIG. 9 (b), a color mosaic type scope 2B is provided with a connector 73B connectable to the above mentioned white light source connector receptacle 71b and color mosaic type signal connector receptacle 72b.

As shown in FIG. 9 (a), a fiber scope 2C fitted with a frame sequential type TV camera can be made in the same form as of the connector 73A of the above mentioned frame sequential type electronic scope 2A when a light source connector 74A and signal connector 75A are combined with each other and can be used as connected to the frame sequential type connector receptacles 71a and 72a.

Also as shown in FIG. 9 (b), a fiber scope 2D fitted with a color mosaic type TV camera can be made in the same form as of the connector 73B of the above mentioned color mosaic type electronic scope 2B when a light source connector 74B and signal connector 75 are combined with each other and is connectable to the white light source connector receptacle 71b and signal connector receptacle 72b.

When connected to the white light source connector receptacle 71b, the light source connector 74A of the fiber scope 2E can feed a white light toward the light guide of the fiber scope 2E and a naked eye observation can be made.

In case a connection different from the connections shown in FIGS. 9 (a) and (b) is made, as explained in the first embodiment, by the connection of the signal connector, the signal of the type signal generating circuit is discriminated by a discriminating circuit and a warning is issued.

Figure 10:
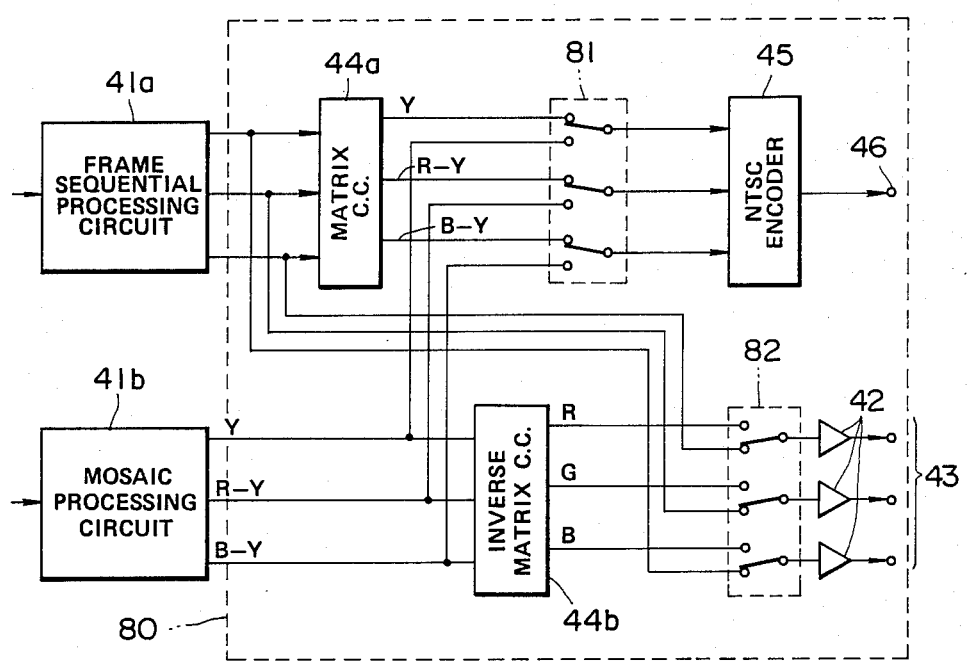
FIG. 10 is a formation view showing an output circuit commonly using a signal converting part.

FIG. 10 shows an essential part of a video processor in the second embodiment of the present invention.

In this second embodiment, an output circuit 80 (provided with a signal converting function) having in common the output ends of the video processors 25a and 25b in the first embodiment.

That is to say, in FIG. 2 a 3-circuit 2-contact switching switch 81 is provided between the output ends of a matrix circuit 44a and an NTSC encoder 45a and a 3-circuit 2-contact switching switch 82 is provided also between the output ends of an inverse matrix circuit 44b and buffers 42 forming a driver.

In the above mentioned switching switch 81, when one contact side is on, the signals of the matrix circuit 44a will be led to a common NTSC encoder 45 and will be made a video signal of an NTSC system in this NTSC encoder 45 and the video signal will be output from a common NTSC output end 46. When the other contact side is selected, the signals of a mosaic type process circuit 41b will be led to the NTSC encoder 45 and will be output from a common NTSC output end 46.

On the other hand, on the other switching switch 82, when the frame sequential side is selected, the output signals of the frame sequential process circuit 41a will pass through common buffers 42 forming a driver and three primary color signals will be output from common R, G and B output ends 43. When the mosaic type process circuit side is selected, three primary color signals R, G and B transmitted through the inverse matrix circuit 44b will be output from the common R, G and B output ends 43.

The above mentioned switching switches 81 and 82 can be respectively switched manually or as operatively connected. Also, the type signal output from the scope in which the above mentioned switching switches 81 and 82 are connected as shown in FIG. 2 is discriminated by a discriminating circuit 28a or 28b. By this discriminated signal, the switching switches 81 and 82 can be switched to a process circuit 41a or 41b processing the signal corresponding to the connected scope.

Figure 11:
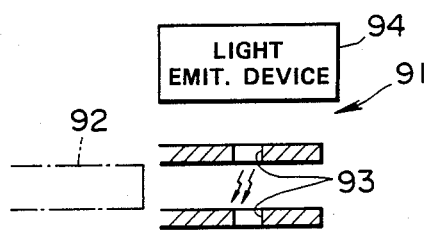
FIG. 11 is an explanatory view showing a connected scope sensing device.

In case the above mentioned switching switches 81 and 82 are formed of analogue switches or the like, they will be able to be automatically switched by a connection sensing apparatus 91 shown in FIG. 11.

For example, the frame sequential type connector is provided with a discriminating pin 92 which is not provided in the mosaic type. On the other hand, the frame sequential type connector receptacle is provided with a recess in which this pin 92 can be engaged. Horizontal hole 93 are provided on both sides opposed to this recess, a light emitting device 93 such as an LED and a light receiving device 95 such as a photodiode are arranged and the output of the light receiving device 95 is input into a sensing circuit 96. When the pin 92 is engaged in the recess, the light of the light emitting device 94 will be intercepted, the output of the light receiving device 95 will vary from "L" to "H" or the like, this output variation will be sensed by the sensing circuit 96 and the switching switches 81 and 82 will be switched so that the frame sequential side may be conductive. In case the output of the light receiving device 94 is "L", the color mosaic type process circuit side will be selected.

Figure 12:
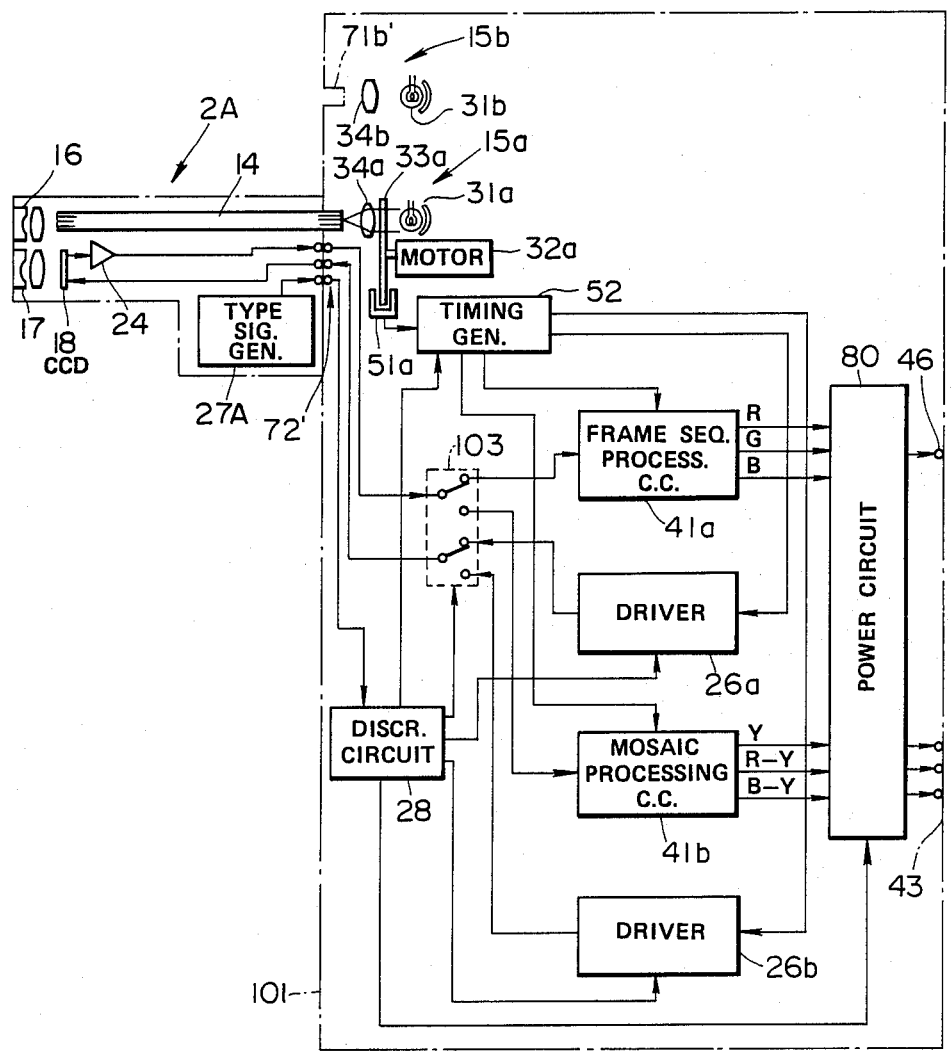
FIG. 12 is a formation view of an imaging apparatus in the third embodiment of the present invention.

FIG. 12 shows the third embodiment of the present invention.

In the imaging apparatus shown in FIG. 2, the signal side input end of the electronic scope 2 is made common and, in this embodiment, the output side is made common.

Figure 13:
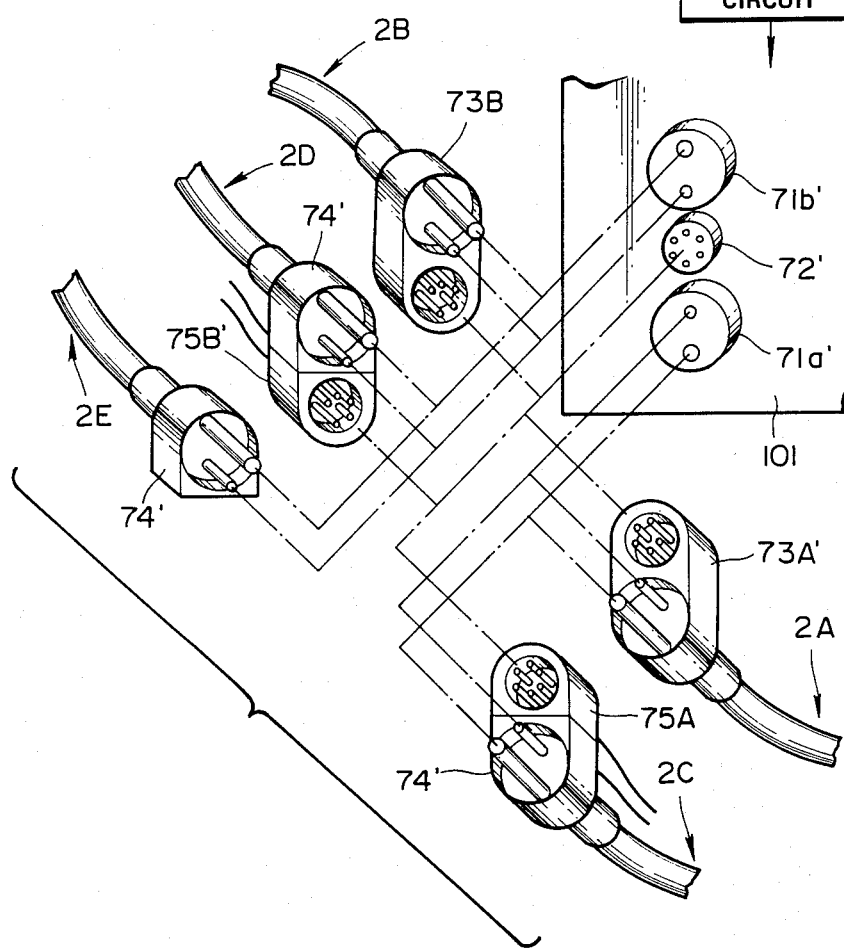
FIG. 13 is a perspective view showing a connector forming the third embodiment.

A signal connector receptacle 72' common with light source side connector receptacles 71a' and 71b' of the imaging apparatus of this embodiment is of the form shown, for example, in FIG. 13. Together with a connector 73A' of the frame sequential type scope 2A or connector 73B' of the mosaic type electronic scope 2B, the respective signal connector parts can be connected to the common signal connector receptacle 72' and the light source side connector parts can be connected to the light source connector receptacles 71a' and 71b' provided respectively below and above. The light source connector 74' and signal connector 75A' of the scope 2C fitted with the frame sequential type TV camera or the connectors 74' and 75B' of the scope 2D fitted with the mosaic type TV camera are also in the same condition. Further, the connector 74' of the fiber scope 2E can be connected to the white light source side connector receptacle 71b'.

The internal formation of the above mentioned imaging apparatus 101 is as shown in FIG. 12.

As shown in FIG. 12, for example, the output signal of the type signal generating circuit (for example, 27A) input into the common discriminating circuit 28 through the common signal connector receptacle 72' discriminates the connected scope in this discriminating circuit 28. As in the first embodiment, this discriminating circuit 28 controls not only both drivers 26a and 26b but also the switching of a newly provided switching switch 103. For example, as shown in FIG. 12, if the frame sequential type scope 2A or 2C is connected, the circuit will be switched to the frame sequential side, the driving pulse of the driver 26a will be applied to the CCD 18 through the connector and the signal read out of the CCD 18 will be input into the frame sequential type process circuit 41a.

On the other hand, if the frame sequential type scopes 2A and 2C are not connected, the mosaic type process circuit side will be selected. By detecting use of the mosaic type scope 2B or 2D, the switching switch 103 may be switched to the mosaic type side.

The above mentioned discriminating circuit 28 feeds a control signal also to a timing generator 52 made common so as to be able to cope with either system.

Also, in this embodiment, the signal through the process circuit 41a or 41b uses an output circuit 80 shown, for example, in FIG. 10. The switching switches 81 and 82 (See FIG. 10) are switched as operatively connected by the output of the discriminating circuit 28. For example, in case the frame sequential type scope 2A or 2C is discriminated, the switches will be switched to the frame sequential side shown in FIG. 10.

Instead of using the output circuit 80 shown in the above mentioned FIG. 10, the output end may be separate for the frame sequential type and mosaic type.

Also, by using the output circuit 80 shown in the above mentioned FIG. 10, the switching switches 81 and 82 may be manually switched.

The others are of the same formation as of the above mentioned first embodiment. In the embodiment shown in FIG. 12, if the light source lamps 31a and 31b are made either one only, for example, the lamp 31b only and the position of this lamp 31b and the position of the other lamp 31a are made movable to be switched, both systems will be able to be illuminated with one lamp. Also, two light source lamps 31a and 31b are provided on both sides passing the center of a rotary plate so that the positions of each other may be exchanged (that is, the lamp 31a in the position of 31b) by the rotary operation and, even if one lamp is broken, the other lamp may be used as an auxiliary lamp.

In this embodiment, it is the same as in the first embodiment that, if the light source connector of the fiber scope 2E is connected to the imaging apparatus 101, a naked eye observation will be able to be made.

In case only the connector 74' of the fiber scope 2E is connected to the white light source connector receptacle 71b', by providing a sensing means of the connection, it may be displayed by a monitor that the fiber scope 2E is connected.

In the above mentioned third embodiment, the signal connector receptacle 72' is common but may be separate as shown in FIG. 1 or 9.

Figure 14:
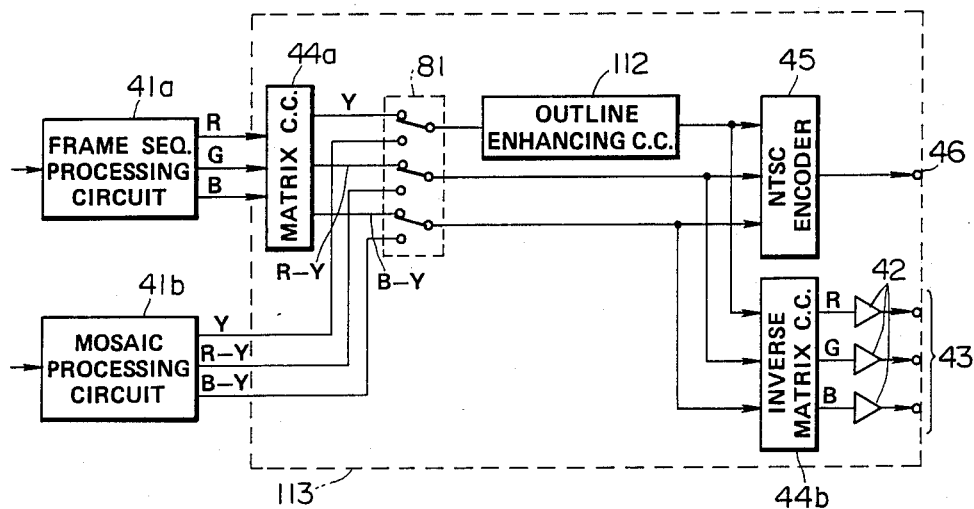
FIG. 14 is a formation view showing an output circuit provided with a signal processing function in the fourth embodiment of the present invention.

FIG. 14 shows an essential part of a video processor in the fourth embodiment of the present invention.

In this video processor, in the output circuit 80 having a signal converting function shown in FIG. 10, there is made an output circuit 113 wherein an outline enhancing signal process is made through an outline enhancing circuit 112 on a luminance signal switched by a switching switch 81. The other switching switch 82 shown in FIG. 10 is not provided but may be provided.

The above mentioned switching switch 81 may be switched by the output of the discriminating circuit 28 shown in FIG. 12 or may be manually switched.

The others are the same as are shown in FIG. 10.

According to this embodiment, the outline is enhanced in common for different luminance signals of two systems. Therefore, as compared with the case that two sets are provided for the respective systems, the number of parts can be made less, the formation is simpler and the cost can be made lower.

In FIG. 14, not only the outline enhancement (horizontal or vertical or both) but also the NTSC encoder 45, inverse matrix circuit and coaxial cable driver 42 are used in common. Instead of the outline enhancing circuit 112, a line interpolating circuit may be provided and an auto gain control circuit ma be provided.

The other commonly used circuits may be such circuits as, for example, of a frame memory, stationary picture memory, color burst generation, power source, character generator, superimposing circuit, keyboard controller and tone adjustment.

Figure 15:
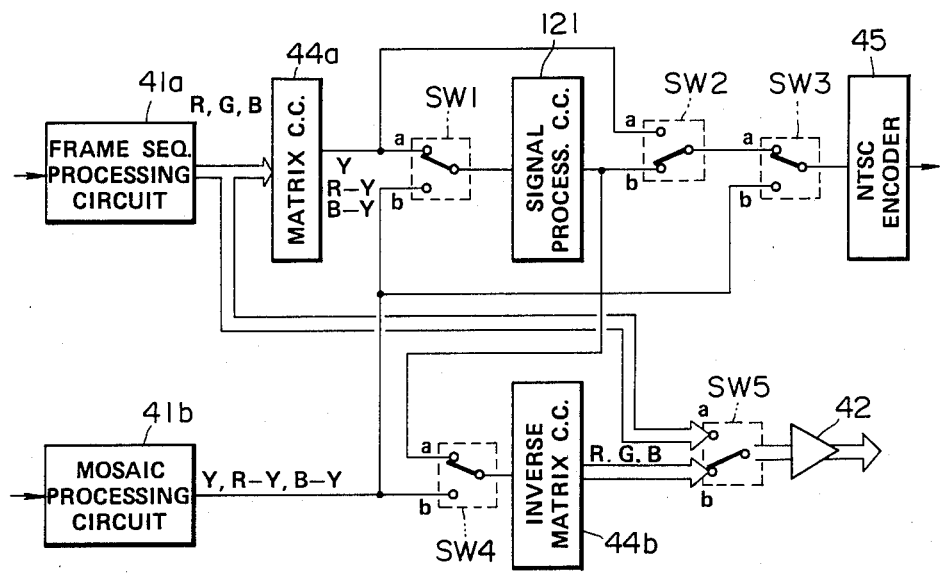
FIG. 15 is a formation view showing a modification of FIG. 14.

FIG. 15 shows a modification of FIG. 14. That is to say, in the circuit shown in FIG. 14, the line enhancing signal process is made for the signal (luminance signal) of either of the frame sequential type and mosaic type. In the signal processing part shown in FIG. 15, a signal process such as the outline enhancement can be selected. In case no signal is processed, the signal deterioration will be prevented. Therefore, switches SW1 and SW2 are provided in front and rear of the signal processing circuit 121 in the rear step of the matrix circuit 44a. The output of the mosaic type process circuit 41b can be input into the NTSC encoder 45 through a switch SW3 on the output side of the switch SW2. In case the signal having passed through the above mentioned signal processing circuit 121 is output from the RGB output end, it will pass through a switch SW4, inverse matrix circuit 44b and switch SW so that the R, G and B signals of the frame sequential type process circuit 41a may not be deteriorated by returning again to the R, G and B signals through the matrix circuit 44a and inverse matrix circuit 44b, R, G and B three primary color signals can be output directly from the RGB output end through a switch SW5.

Whether the signal is processed (on) or not (off) in the state of the respective switches SW1 to SW4 in the modification shown in FIG. 15 is as in the logical table below.

| Output | Signal process | SW1 | SW2 | SW3 | SW4 | SW5 |
|---|---|---|---|---|---|---|
| Frame sequential type | On | a | b | a | a | b |
| | Off | Δ | a | Δ | a | a |
| Mosaic type | On | b | b | a | a | b |
| | Off | Δ | Δ | b | b | b |

Δ represents that either side is good.

In the embodiment in FIG. 15, the luminance signal Y, color difference signals R-Y and B-Y are processed but only the luminance signal may be processed.

In the circuit shown in FIG. 10, the luminance signal and respective R, G and B color signals may be processed in the later steps of the respective switching switches.

Figure 16:
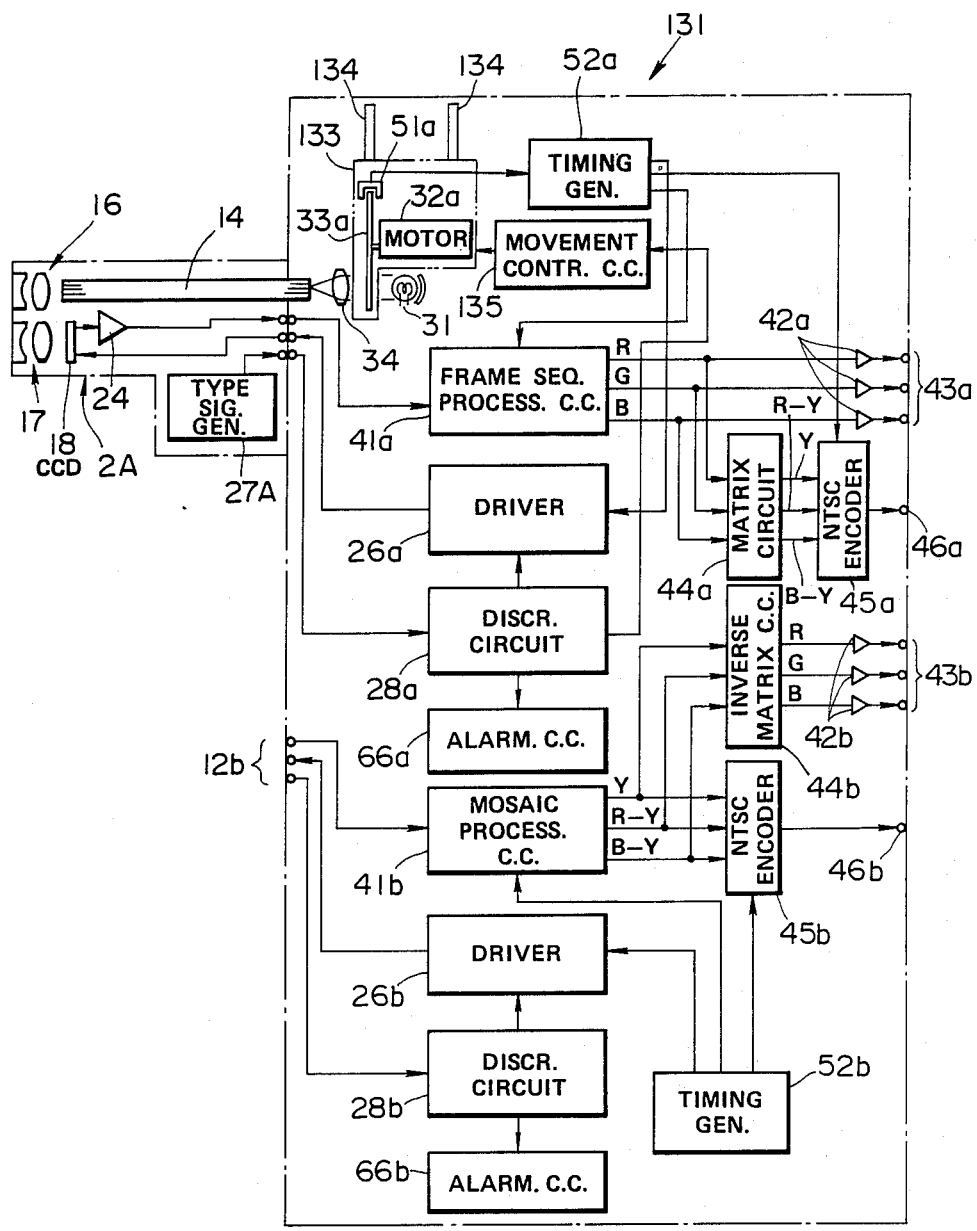
FIG. 16 is a formation view of an imaging apparatus in the fifth embodiment of the present invention.

FIG. 16 shows an imaging apparatus having in common the light source connector part in the fifth embodiment of the present invention.

Figure 17:
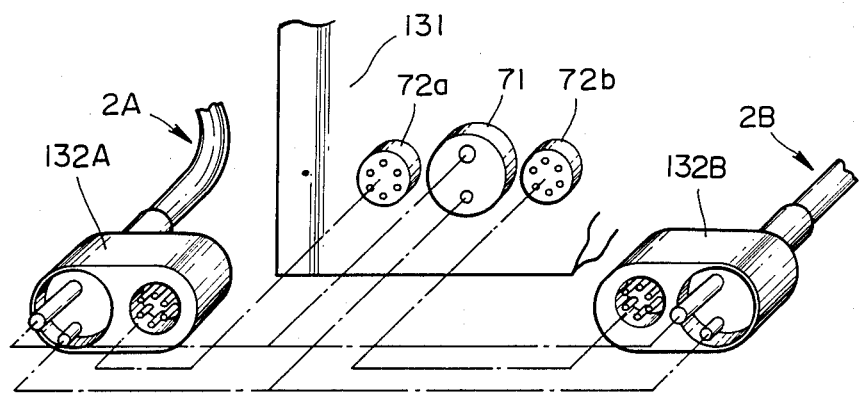
FIG. 17 is a perspective view showing a connector in the fifth embodiment.

For example, on the front surface of a housing of an imaging apparatus 131 in the fifth embodiment, as shown in FIG. 17, a common light source connector receptacle 71 is provided and a frame sequential type signal connector receptacle 72a and color mosaic type signal connector receptacle 72b are symmetrically provided on both sides of it.

On the other hand, the connector 132A of the field sequential type electronic scope 2A and the connector 132B of the color mosaic type electronic scope 2B are so made that both of their light source connector parts can be fitted to the light source connector receptacle 71 and that the respective signal connector parts can be connected respectively to the frame sequential type connector receptacle 72a and color mosaic type connector receptacle 72b. Though not shown in FIG. 17, the case of the electronic scopes 2C and 2D fitted respectively with the frame sequential type and mosaic type TV cameras is also the same. The fiber scope 2E can have its connector connected to the light source connector receptacle 71 to make a naked eye observation.

Figure 18:
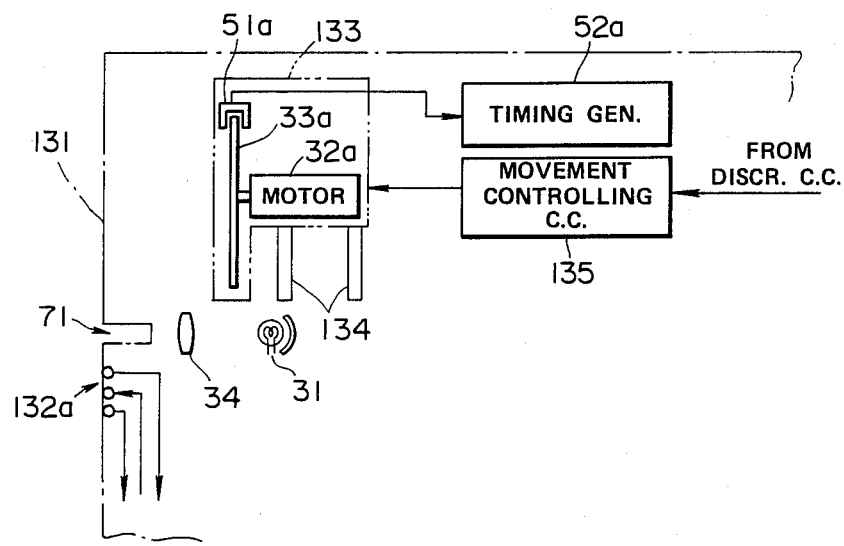
FIG. 18 is a formation view showing as magnified a light source part in the fifth embodiment.

In the imaging apparatus 131 shown in FIG. 16, as magnified and shown in FIG. 18, a rotary filter part 133 is made movable along rails 134.

The above mentioned rotary filter part 133 is set normally at the ends on one side of the rails 134. For example, as shown in FIG. 18, when the rotary filter 33a is retreated from the light path between the light source lamp 31 and lens 34, the white light source part will be formed. On the other hand, when the rotary filter part 133 is moved from this state to the lower side of the rails 134, as shown in FIG. 16, it will be interposed in the light path and the frame sequential light source part will be formed.

Now, the above mentioned rotary filter part 133 is controlled in the movement by the movement controlling circuit 135 which is operated by a discriminating signal of the discriminating circuit 28a. In this embodiment, when the frame sequential type scope is identified by the type signal by a type signal generating circuit 27A or 27C, from the discriminating circuit 28a, a movement controlling instruction will be output to a movement controlling circuit 135 and a rotary filter part 133 will be moved from the state shown in FIG. 18 to the state shown in FIG. 16.

On the other hand, in case the connector of the mosaic type scope 2B or 2D is connected, the rotary filter part 133 will not be moved and a white light will be fed. Also, in case a fiber scope 2E is fitted, a white light will be fed to the connector of the fiber scope.

When the frame sequential type scope 2A or 2C is fitted and is then removed, the rotary filter part 133 will be returned to be retreated from the light path.

The others are the same as of the formation shown in FIG. 2.

According to this fifth embodiment, as the light source part is used in common, without providing two sets of light source parts, the frame sequential type or mosaic type scope can be coped with. Also, in case the connector of the fiber scope is to be connected, such mis-connection as connecting by mistake to the frame sequential type side if there are two light source connector receptacles can be easily prevented.

The above mentioned rotary filter part 133 may be manually moved.

Figure 19:
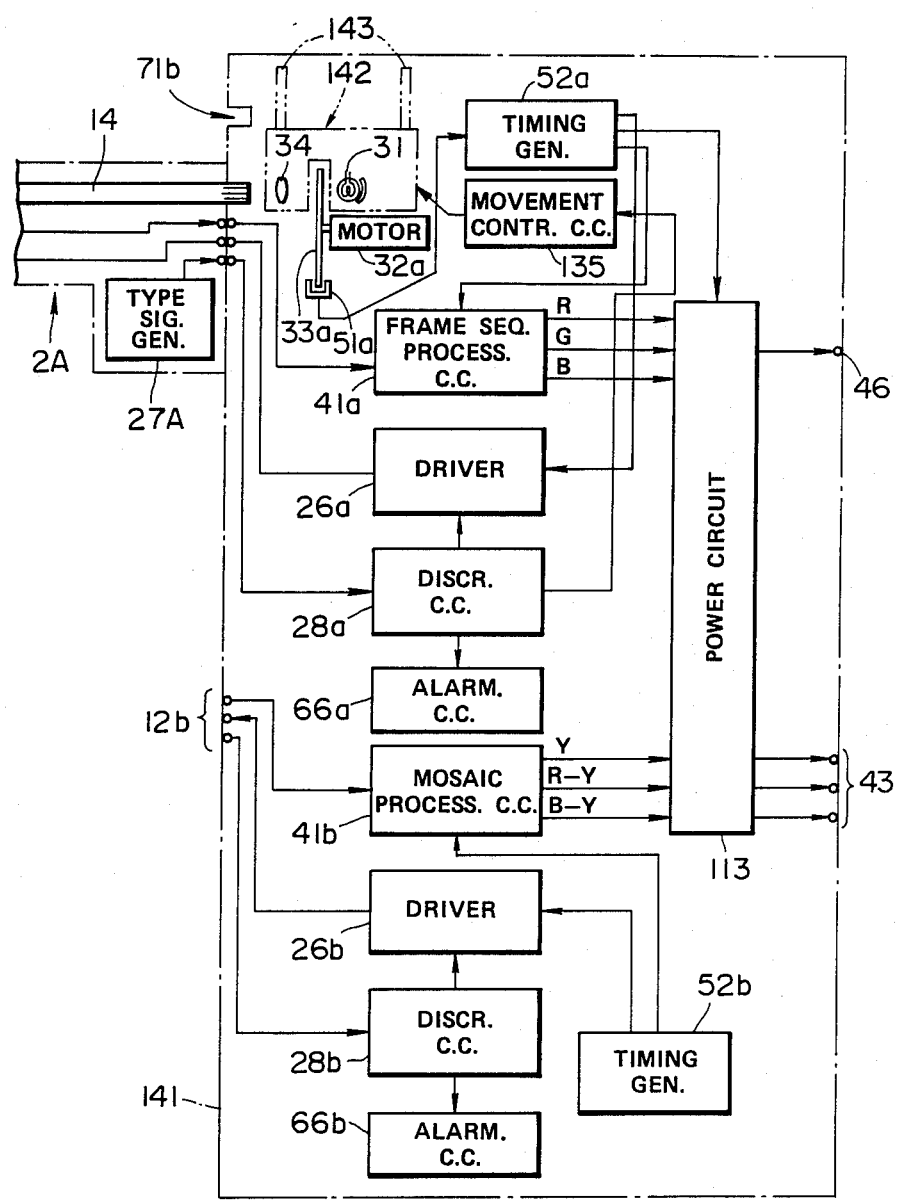
FIG. 19 is a formation view of an imaging apparatus in the sixth embodiment of the present invention.

FIG. 19 shows an imaging apparatus body 141 in the sixth embodiment.

In the above mentioned fifth embodiment, the rotary filter part 133 is made movable. In this embodiment, a light source part 142 is made movable along rails 143.

The connector receptacle part, for example, on the front surface of the imaging apparatus 141 of this embodiment is of such formation as is shown in FIG. 9. On other hand, the scope side connector is also of the form shown in the same view.

Figure 20:
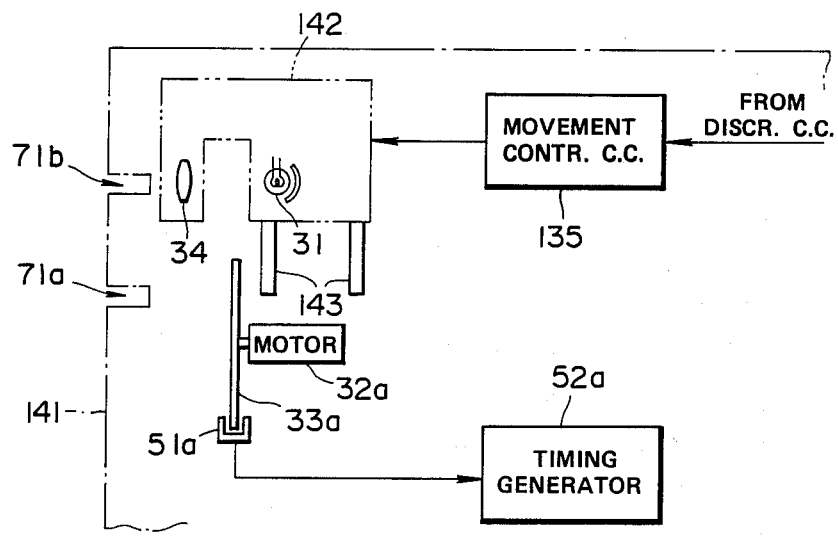
FIG. 20 is a formation view showing as magnified a light source part in the sixth embodiment.

Now, as shown in FIG. 20, the light source part 142 within the imaging apparatus 141 is normally opposed to the inside of the white light source connector receptacle (represented by the same reference numeral as is shown in FIG. 9) 71b. When the frame sequential type scope 2A or 2C is connected the same as in the fifth embodiment, it will be discriminated by the type signal by the discriminating circuit 28a, the light source part 142 will be moved (downward in FIG. 20 and horizontally in FIG. 9) through the movement controlling circuit 135 and will be opposed to the inside of the frame sequential type connector receptacle 71a as shown in FIG. 19 and the illuminating lights of R, G and B having passed through the rotary filter 33a will be fed to the frame sequential type light source connector part.

Now, as shown in FIG. 19, the imaging apparatus 141 of this embodiment is different from the one shown in FIG. 16 and uses a common output circuit 113. The concrete formation of this output circuit 113 is shown in FIG. 14.

The others are of the same formation as is shown in the above mentioned FIG. 16 and have substantially the same operation and effect.

In the above mentioned sixth embodiment, the connector receptacle can be moved together with the light source part 142. In such a case, it will not be moved in case the mosaic type scope 2B or 2D is connected but will be moved in case the frame sequential type scope 2A or 2C is connected. It will not be moved in the case of the fiber scope 2E. In this case, the connector receptacle will be one.

In this embodiment, too, a manually movable structure can be made.

Figure 21:
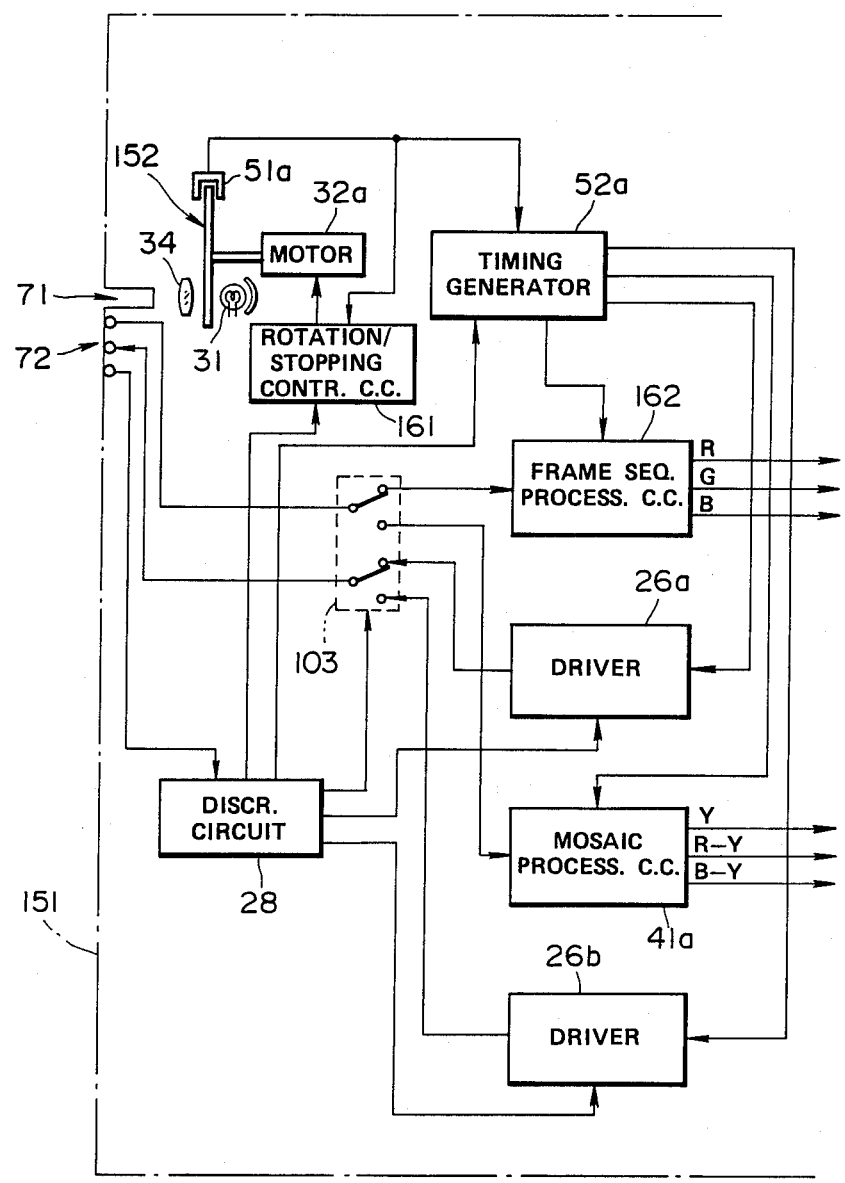
FIG. 21 is a formation view of an essential part of an imaging apparatus in the seventh embodiment.

FIG. 21 shows an essential part of an imaging apparatus 151 in the seventh embodiment of the present invention.

In this embodiment, the frame sequential illuminating lights are not of R, G and B in the embodiment shown in FIG. 12 but are of R, W and B.

Figure 22:
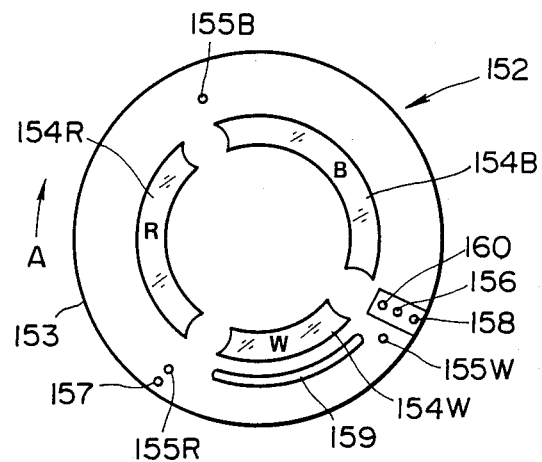
FIG. 22 is an explanatory view showing the structure of a rotary filter forming a light source part of the seventh embodiment.

The rotary filter 152 to be used for the frame sequential illumination with the above mentioned illuminating lights of R, W and B is provided with fan-shaped window parts in a disc-like filter frame 153 as shown in FIG. 22. R, W and B color transmitting filters 154R, 154W and 154B are fitted to the respective window parts. This W transmitting filter 154W is a filter transmitting R, G and B. (It may be an approximately transparent plate to transmit all the white light.)

The R, W and B color transmitting filters 154R, 154W and 154B are adjusted in the arcuate length so that the illuminating period may be different in response to the photosensitive characteristic of the CCD 18 or 22. In the above mentioned filter frame 15 leading pulse (detecting) holes 155R, 155W and 155B are provided respectively near the ends (with respect to the rotating direction) of the R, W and B color transmitting filters 154R, 154W and 154B so that the leading time just after being illuminated with R, W and B may be detected. The positions of these leading pulse holes 155R, 155W and 155B can be detected by the fact that, in case the position opposed to the photosensor 156 arranged as opposed to the light emitting device to hold the filter frame 153 is reached, the light of the light emitting device will be received in the form of pulses in the photosensor 156. When this pulse-like light is detected, the detecting signal will be transmitted to the timing generator 52a and a readout driving pulse will be applied to the CCD 18 or 22 through the driver 26a or 26b.

In the above mentioned filter frame 153, a starting pulse hole 157 is provided for example, in a position radially adjacent to the leading pulse hole 155R. When this position reaches a position opposed to the photosensor 158, the photosensor 158 will output a starting pulse.

Further, in order to detect the position of the W color transmitting filter 154W, an arcuate slot 159 is formed in a peripheral outside position of this color transmitting filter 154W. The position of the W color transmitting filter 154W can be detected by detecting this slot 159 with the photosensor 160. The output of this photosensor 160 controls the stopping position of the rotary filter 152. That is to say, in case the motor 32a rotating and driving the rotary filter 152 is not in a rotating driving state, the output of the photosensor 160 is input into a rotation/stop controlling apparatus 161 to control the stopping position of the rotary filter 152 so that the stopping position of the rotary filter 152 may be the position opposed to the photosensor 160. In this stopping position state, the illuminating light of the light source lamp 31 passes through the W color transmitting filter 154W and can feed a white illuminating light as opposed to the light source connector receptacle 71. When a fiber scope is connected to the connector receptacle 71 but nothing is connected to the connector receptacle 72 or when nothing is connected to the connector receptacles 71 and 72 (Both of these states can be discriminated by the discriminating circuit sensing the high impedance state) or, when a mosaic type scope is connected this white illuminated state will be made.

On the other hand, when a frame sequential type scope is connected, the connection will be sensed by the discriminating circuit 28, a motor 32a rotating and driving instruction signal is output to the rotation/stop controlling circuit 161 to rotate and drive the motor 32a to be in a frame sequential illuminating state.

Figure 23:
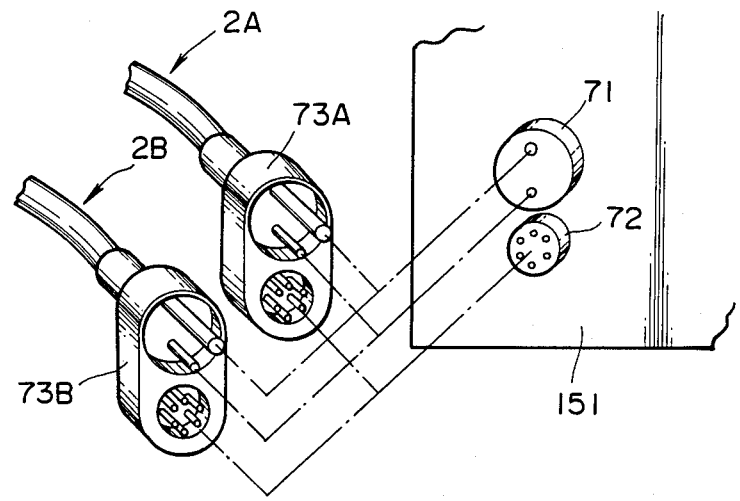
FIG. 23 is a perspective view showing a connector in the seventh embodiment.

In this embodiment, the light source connector receptacle 71 of the imaging apparatus 151 can be used in common for the white color and sequence. The signal connector receptacle can be used in common for the frame sequential type and mosaic type as shown, for example, in FIG. 23. Two electronic scopes 2A and 2B are shown in FIG. 23. The other scopes 2C, 2D and 2E can be also connected.

Figure 24:
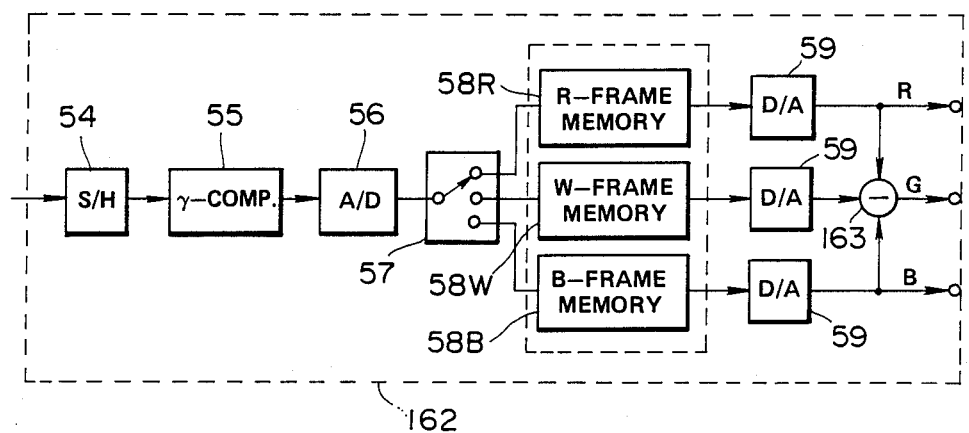
FIG. 24 is a block diagram showing the formation of a field sequential type process circuit in the seventh embodiment.

Now, in this embodiment, as the frame sequential illuminating light is not of R, G and B, the frame sequential process circuit 162 is of such formation as is shown, for example, in FIG. 24. That is to say, in the process circuit 41a shown in FIG. 7, the G frame memory 58G is replaced with the W frame memory 58W (though the memory contents are different, the same frame memory can be used in the hardware), further the W color signal read out of the W frame memory 58W and made an analogue signal by the D/A converter 59 is input into a deductor 163 and the R color signal and B color signal are deducted to produce the G color signal. The others are the same as in the process circuit 41a shown in FIG. 7.

The other formation of the imaging apparatus 151 shown in the above mentioned FIG. 21 are the same as are shown in FIG. 12.

According to this embodiment, both frame sequential type and mosaic type commonly use the light source part, can be easily used when merely a scope is connected. Also, there is no need of newly providing a moving means of moving the light source part or rotary filter part. The cost can be reduced and the size can be made small.

In the above mentioned embodiment, the light source connector means and signal connector means are commonly used but the signal connector means can be used not commonly.

In the above mentioned embodiment, the frame sequential illumination is made with R, W and G but is not limited to this. The illumination can be made, for example, with R, G, W; W, G and B; Cy (cyanine), Ye (yellow) W; Cy, W, Mg (magenta); W, Ye, Mg, etc.

Figure 25:
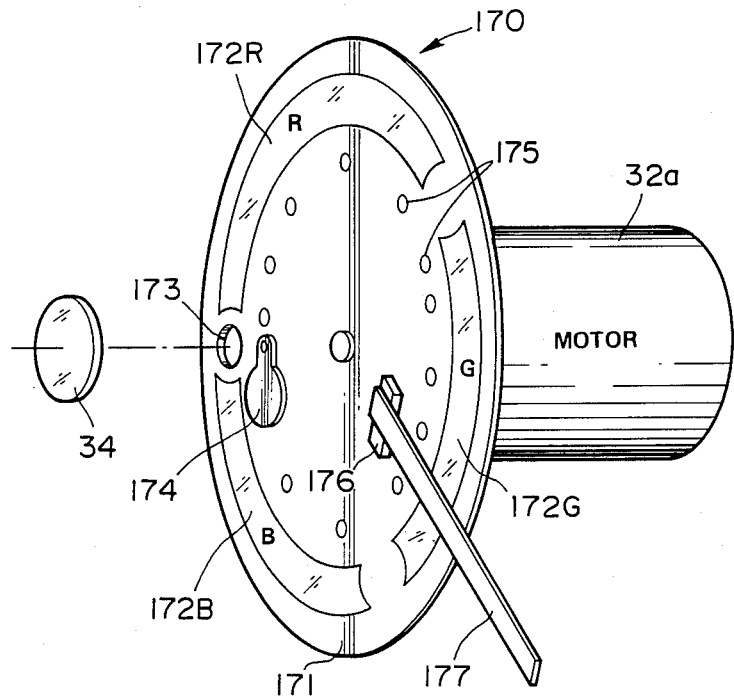
FIG. 25 is a perspective view showing a rotary filter in the eighth embodiment of the present invention.

FIG. 25 shows the periphery of a rotary filter part 170 in the eighth embodiment of the present invention.

In this embodiment, R, G and B color transmitting filters 172R, 172G and 172B are provided in a filter frame 171. A white illuminating hole 173 is provided in a light intercepting part, for example, between the R and B color transmitting filters 172R and 172B and can intercept the light with a light intercepting plate 174 rotatably fitted with a position in the course of a line segment connecting the hole 173 and the center as a pivotal point.

Figure 26:
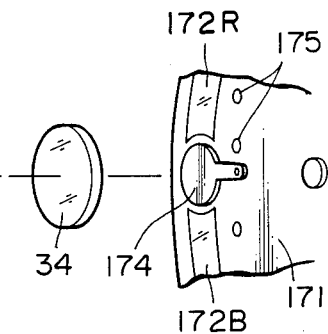
FIG. 26 is a perspective view showing a part of a rotary filter as being rotated.

That is to say, in the above mentioned light intercepting plate 174, when the filter frame 171 is rotated by the motor 32a, by the centrifugal force, as shown in FIG. 26, the direction connecting the center position of the disc-like light intercepting part and the pivotal point will coincide with the radial direction, in this state, the hole 173 will be closed with the light intercepting plate and ordinary R, G and B frame sequential illuminations will be able to be made.

On the other hand, when stopped, no centrifugal force will operate and therefore, as shown in FIG. 25, the light intercepting plate 174 will retreat from the hole 173 due to the gravity.

The above mentioned filter frame 171 is controlled in the position so that, when stopped, the hole 173 may be on the optical axis connecting the light source lamp and lens 34. For controlling the position or for detecting the timing of reading out the CCD signal in the case of the R, G and B frame sequence, many holes 175 are provided in the peripheral direction in the filter frame 171 and a light emitting device and photosensor 176 are arranged on both sides f the plate surface of the filter frame 171 to form a position detecting rotary encoder. In FIG. 25, the photosensor 176 is fitted to the tip of the sensor fitting plate 177.

Figure 27:
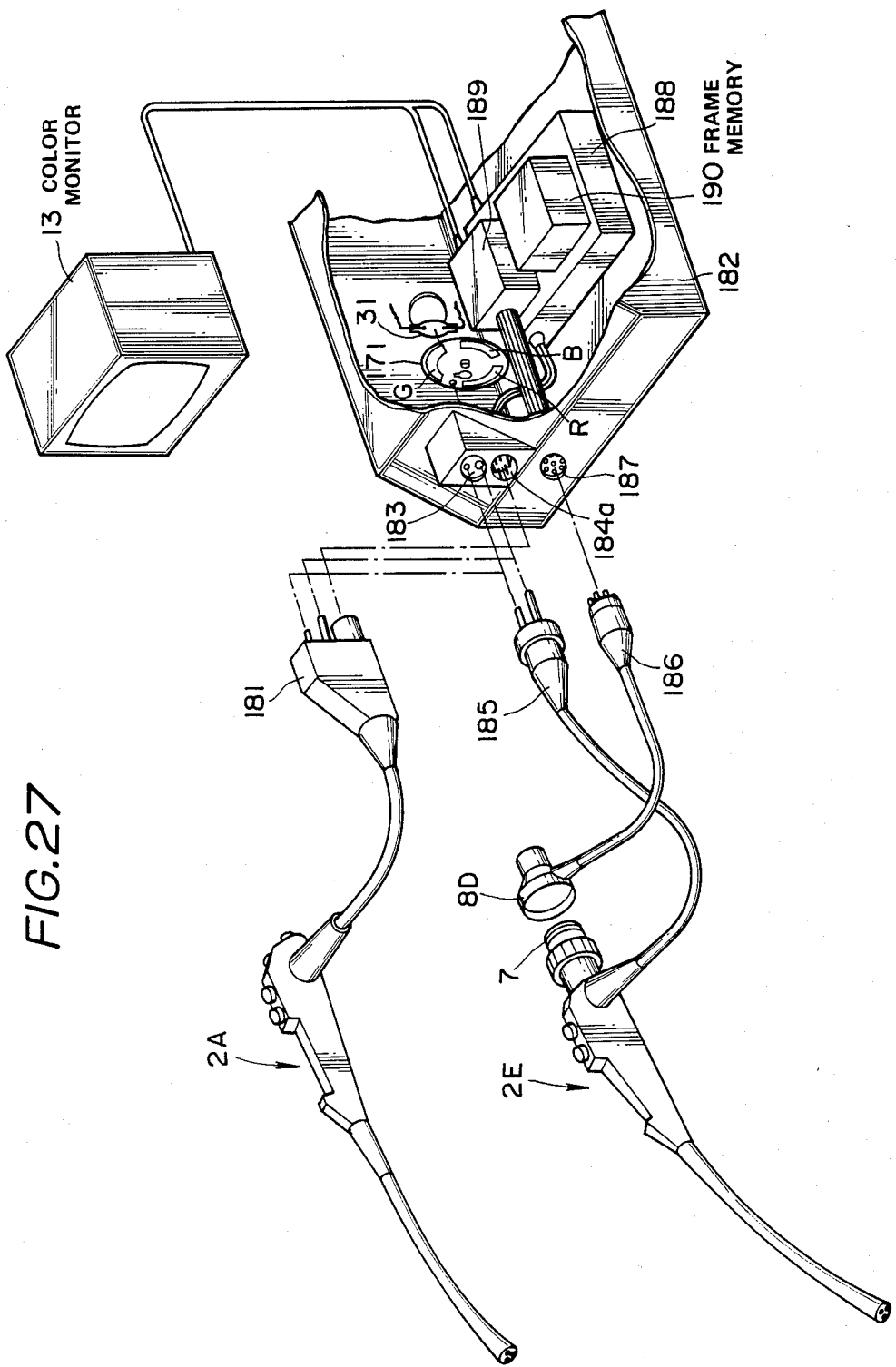
FIG. 27 is a perspective view showing a part of the system of the eighth embodiment.
Figure 28:
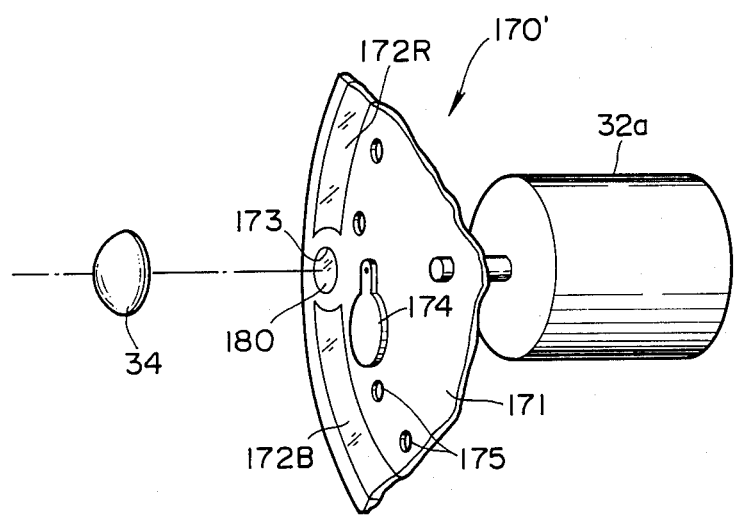
FIG. 28 is a perspective view showing an essential part of a modification a rotary filter in the eighth embodiment of the present invention.

Now, the entire system of this embodiment is of the structure shown, for example, in FIG. 27.

FIG. 27 shows, for example, a frame sequential type electronic scope 2A, a fiber scope 2E and a mosaic type TV camera 8D connectable to this fiber scope 2E.

The connector 181 of the above mentioned frame sequential type electronic scope 2A has a light source connector and signal connector made integral and can be connected to a light source connector receptacle 183 and frame sequential type connector receptacle 184a.

On the other hand, with the fiber scope 2E, its connector 185 can be connected to the light source connector receptacle 183 to make a naked eye observation. For example, a mosaic type TV camera 8D is fitted to the eyepiece part y to form a scope fitted with a mosaic type TV camera. The signal connector 186 of this mosaic type TV camera 8D may be used as connected to a mosaic type signal connector receptacle 187.

Though not shown in FIG. 27, the mosaic type electronic scope 2B can be also used. The above mentioned fiber scope 2E to which the frame sequential type TV camera 8C is connected can be also used.

Now, the formation within the image apparatus 182 is substantially the same as the combination of FIGS. 19 and 21. (The light source part 142 and its controlling circuit system of FIG. 19 are replaced with the light source part of FIG. 21 and the filter par is replaced with the rotary filter part shown in FIG. 25 so that R, G and B frame sequential lights and a white light may be output.) These are arranged as shown in FIG. 27.

For example, the frame sequential type video processor is contained within a box-like housing 188 and a housing 189 containing a mosaic type video processor is arranged on the upper surface of the housing 188. A frame memory 190 forming a frame sequential type video processor is arranged also on the upper surface of the above mentioned housing 188.

A color monitor 13 is connected through a signal cable to the signal output ends of both of these housings 188 and 189.

The filter frame 171 forming the rotary filter part 170 and the light source lamp 31 are arranged inside the above mentioned light source connector receptacle 183.

Figure 38:
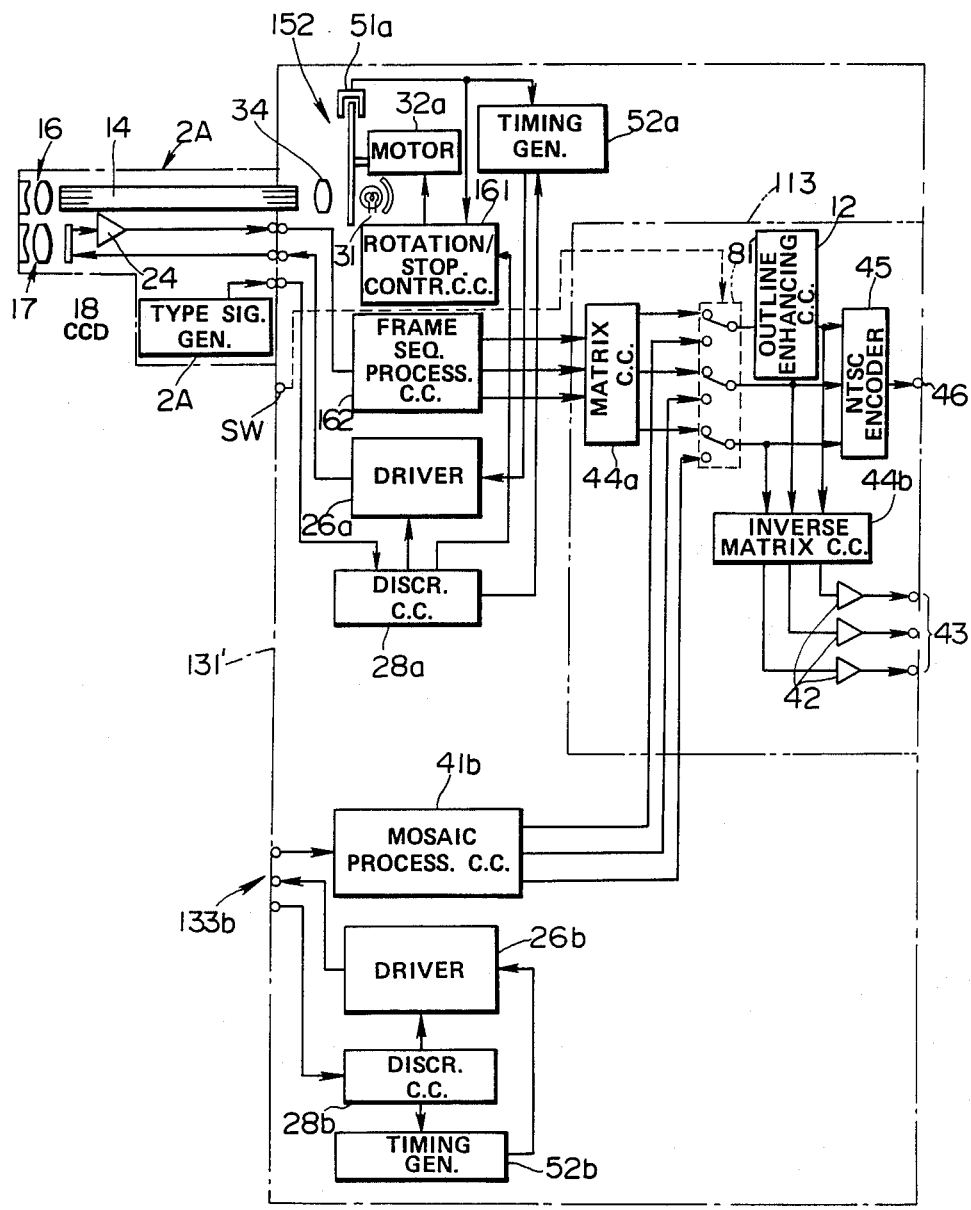
FIG. 38 is a formation diagram of an imaging apparatus in a modification of the eleventh embodiment.

FIG. 38 shows a rotary filter part 170' of a modification of the above mentioned seventh embodiment.

Figure 29:
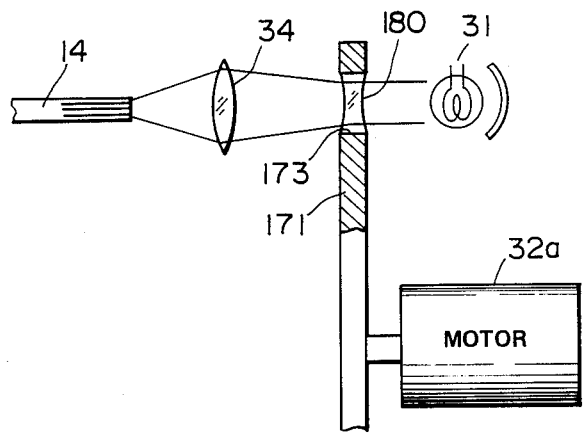
FIG. 29 is sectioned view of an essential part of FIG. 28.

In this rotary filter 170', a concave lens 180 is fitted in the hole 173 of the filter frame 171 shown in the above mentioned FIG. 25 and the light source part shown in section through this hole 173 is as in FIG. 29.

By the above mentioned concave lens 180, the illuminating light condensed on the light guide fiber end surface in the case of the illumination with a white light is defocused so that the light guide fibers may not burn. In case the concave lens 180 is interposed, that is, in case the light is passed through the filter, it will be focused on the light guide fiber end surface. In such a case, the light will be reduced by the filter and therefore the light guide fiber end surface will not substantially burn. It may be set that, by moving the lens 34 or light source lamp 31 (on rails) in the optical axis direction, in the case of the illumination with a white light, the light will be defocusive and, in the case of the frame sequence it will be focused.

Figure 31:
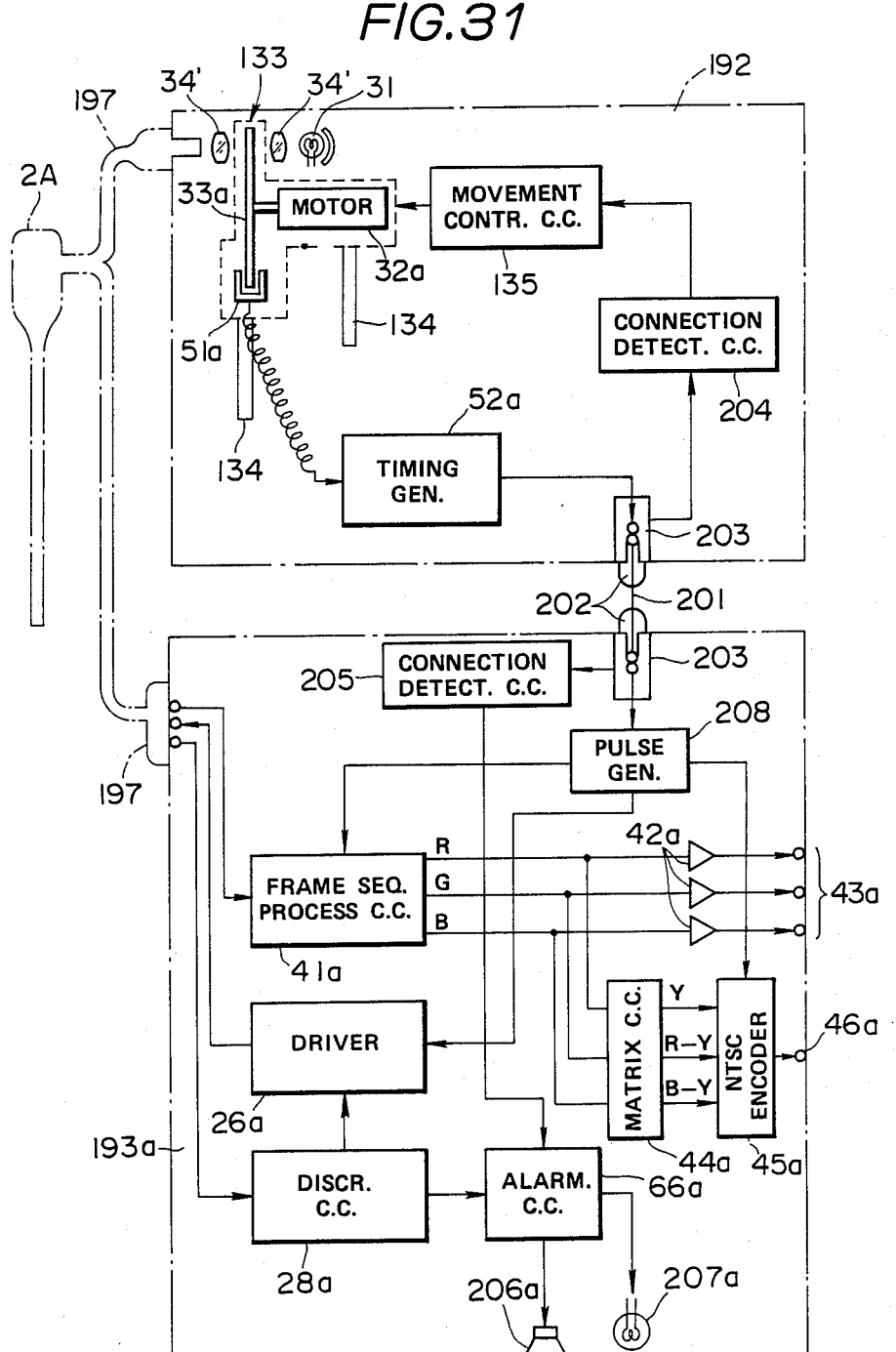
FIG. 31 is a formation diagram of the ninth embodiment as combined with a frame sequential type electronic scope.
Figure 32:
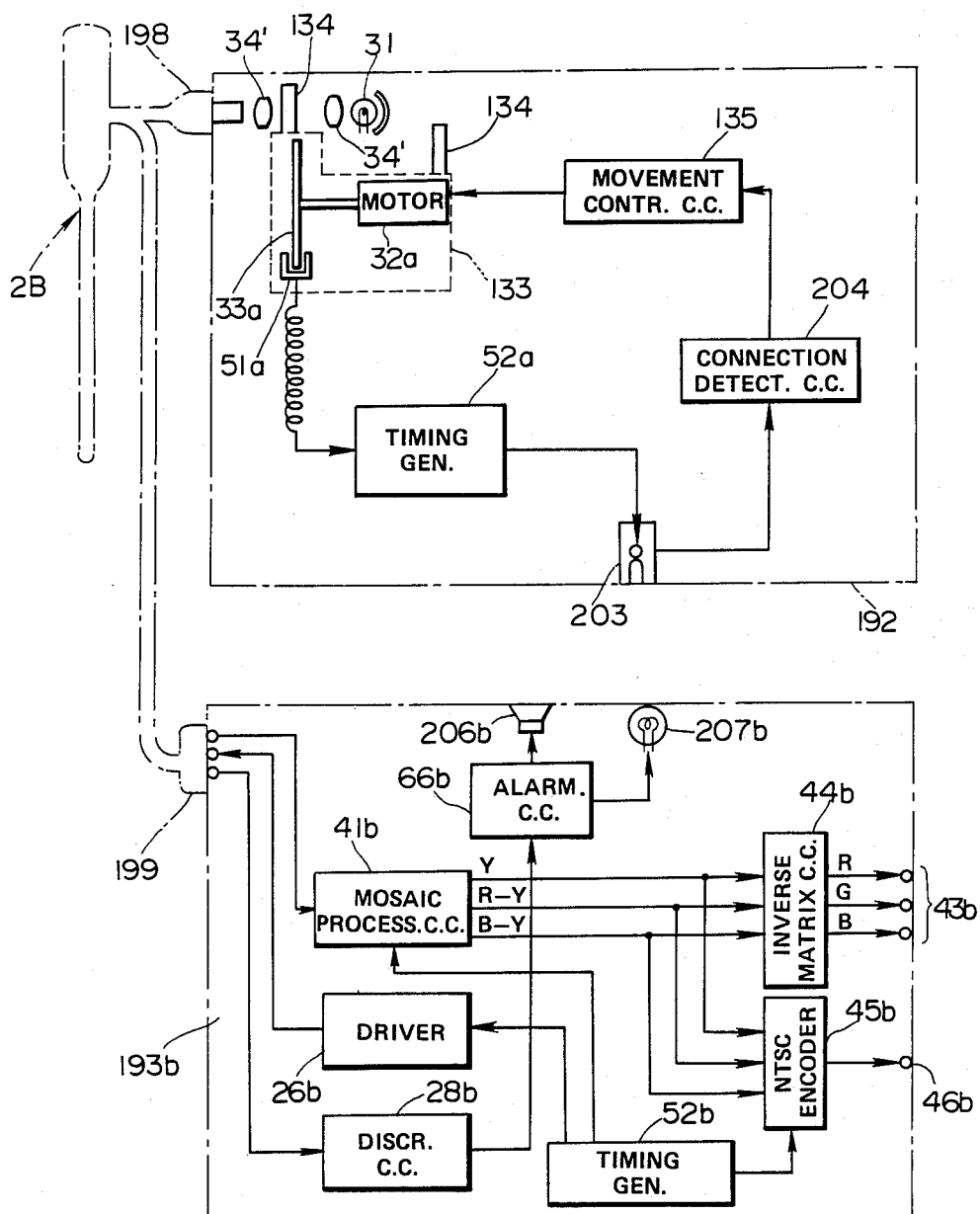
FIG. 32 is a formation diagram of the ninth embodiment as combined with a mosaic type electronic scope.

FIG. 30 shows the contour of the ninth embodiment of the present invention. FIG. 31 shows a frame sequential type scope as assembled. FIG. 32 shows a mosaic type scope as assembled.

In this embodiment, an imaging apparatus 191 is formed of a separate and commonly used light source part 192 and a frame sequential type video processor part 193a shown in FIG. 31 or a mosaic type video processor part 193b shown in FIG. 32. As shown in FIG. 30, a light source connector receptacle 194 is provided on the lower side on the front surface of the light sources part 192. On the other hand, a signal connector receptacle 195 is provided on the upper side on the front surface of the video processor part 193a or 193b. These both connector receptacles 194 and 195 will be adjacent to each other above and below when the light source part 192 is overlapped on the upper surface of the video processor part 193a or 193b (one video processor part 193a is shown in FIG. 30).

On the other hand, in the frame sequential type electronic scope 2A, its connector 197 has the light source connector part and signal connector part made integral. As shown in FIG. 30, when the light source part 192 is overlapped on the video processor part 193a, both connector parts can be connected to the respective connector receptacles 194 and 195.

On the other hand, for example, in the mosaic type electronic scope 2B, its connector is separated into a light source connector 198 and a signal connector 199 which can be connected respectively to the connector receptacles 194 and 195. For example, even in the fiber scope 2C fitted with a frame sequential type TV camera, the light source connector 198 and signal connector 200 can be connected respectively to the connector receptacles 194 and 195.

Now, the above mentioned light source part 192 is of a formation similar to that of the light source part in FIG. 16 or 18. The lens 34 in FIG. 16 is made two lenses 34' in this embodiment.

This light source part 192 is provided with a connector receptacle 203 connecting one of connectors 202 of a cable 201 to feed a timing pulse of the timing generator 52a to the frame sequential type video processor part 193a and, in the same manner, the frame sequential type video processor part 193a is also provided with the connector receptacle 203.

The above mentioned light source part 192 is provided with a connection sensing circuit 204 for sensing whether the connector 202 of the signal cable 201 is connected to the connector receptacle 203 or not. When the cable 201 is connected as shown in FIG. 31, a movement instructing signal will be output to the movement controlling circuit 135 by the output of this circuit 204, the rotary filter part 133 will be moved along the rails 134, the rotary filter 33a will be interposed in the course of the illuminating light path and a frame sequential illumination will be made.

On the other hand, a connection sensing circuit 205 for sensing whether the connector 202 of the signal cable 201 is connected to the connector receptacle 203 or not is provided also within the frame sequential video processor part 193a. The output of this sensing circuit 205 is input into the warning circuit 66a. When this warning circuit 66a senses from the discriminating circuit 28a that the frame sequential scope 2A or 2C is connected, if a sensing signal showing that the cable 201 is not connected is input from the connection sensing circuit 205, it will be warned by a warning buzzer 206a and warning light 207a that the cable 201 is not connected. Also, it will be warned that the signal connector 199 of the mosaic type scope 2B or 2D is connected to the signal connector receptacle 195.

Through the above mentioned cable 201, the timing pulse from the light source part 192 outputs a control signal to the driver or the like through the pulse generator 208 within the video processor part 193a. The other formations are the same as are shown in FIG. 16.

The formation of the mosaic type video processor part 193b shown in FIG. 32 is similar to that shown in FIG. 16.

The above mentioned video processor part 193b is provided with a warning circuit 66b operated by the output of the discriminating circuit 28b when the signal connector of the frame sequential type scope 2A or 2C is connected to the mosaic type signal connector receptacle 195, this warning circuit 66b will sense the misconnection and it will be warned by the buzzer 206b or warning light 207b. The others are of the same formation as of the one shown in FIG. 16.

In case the above mentioned mosaic type scope 2B or 2D or the fiber scope 2E is connected, the rotary filter part 133 will not be moved and therefore the white light of the light source lamp 31 will be condensed and radiated to the connector 198 through the lens 34.

FIG. 31 shows the frame sequential type electronic scope 2B as connected but its connector 197 is separated for the sake of convenience.

In the above mentioned embodiment, even if the connector is integral as in the case of the frame sequential type scope 2A or is separated as in the case of the mosaic type scope 2B, it can be connected.

In FIG. 30, the connector 197 of the frame sequential type electronic scope 2A is made integral for the light source and for the signal but may be separated as in the case of the mosaic type electronic scope 2B. On the contrary, the connectors 198 and 199 of the mosaic type electronic scope 2B may be made integral.

The above mentioned connection sensing circuits 204 and 205 are not always necessary. In the above mentioned embodiment, the rotary filter part 133 is made movable but the lamp 31 and connector receptacle 195 part may be made movable.

Also, a signal for increasing or decreasing the light amount of the lamp 31 may be sent through a signal line not illustrated to the light source part 192 also from the video processors 193a and 193b side to automatically adjust the light.

Figure 33:
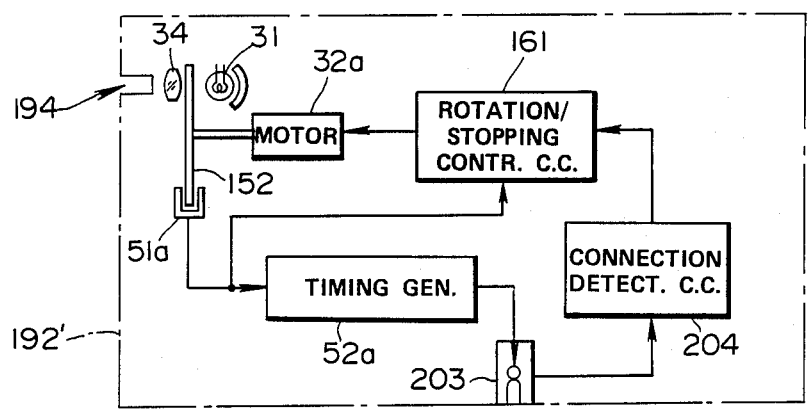
FIG. 33 is a formation diagram showing a modification of a light source part in the ninth embodiment.

FIG. 33 shows a modification of the light source part 192 in the above mentioned ninth embodiment.

In the light source part 192' of this embodiment, instead of the movable structure in which the rotary filter 152 shown in FIG. 22 is used as a rotary filter of the rotary filter part 133 of FIG. 31, the rotation/stop is controlled by the rotation/stop controlling circuit 161 (See FIG. 21). In this case, the frame sequential type process circuit 162 shown in FIG. 24 is used. This embodiment has substantially the same function as of the above mentioned ninth embodiment.

Instead of the above mentioned rotary filter 152, the rotary filter part 170 shown in FIG. 25 may be used. In this case, the frame sequential type process circuit 41a shown in FIG. 31 can be used.

Figure 34:
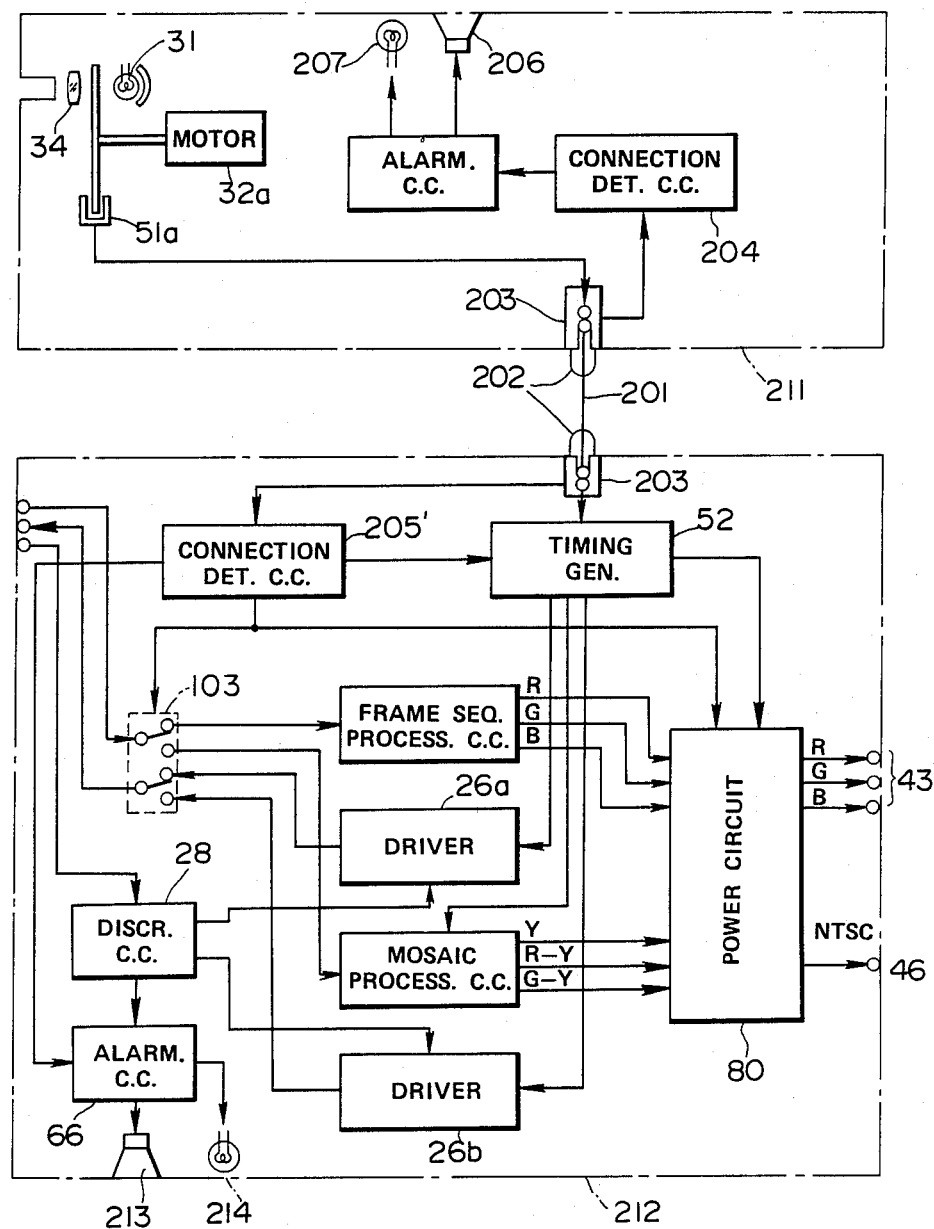
FIG. 34 is a formation diagram of an imaging apparatus in the tenth embodiment of the present invention.

FIG. 34 shows the tenth embodiment of the present inventions.

In this embodiment, the light source part 211 is not provided with the timing generator 452a in the light source part 192' shown in FIG. 33 but uses a common timing generator 52 within a common video processor part 212. In the case of the illumination by frame sequence, unless the cable 201 is connected by the connection sensing circuit 204, it will be warned by the buzzer 206 or by lighting the lamp 207.

The above mentioned video processor part 212 is provided with a connection sensing circuit 205' the same as in the above mentioned ninth embodiment, a buzzer 213 driven by the warning circuit 66 and a warning light 214 in addition to those shown in FIG. 12. This connection sensing circuit 205' has the same function as of the connection sensing circuit 205 shown in FIG. 31 in the ninth embodiment.

The above mentioned buzzer 213 and warning light 214 are operated by the output of the discriminating circuit 28 and have the same function as of the operation by both discriminating circuit 28a and 28b of the above mentioned ninth embodiment.

The others are of the same formation as of the above mentioned ninth embodiment.

According to this embodiment, as the video processor part 212 is commonly used, the number of units forming the entire system can be reduced and the movement is convenient. As at least a part of the signal processing system is commonly used, the number of the component parts can be reduced and the cost can be made low.

Instead of the output circuit 80 provided with the signal converting function in the above mentioned embodiment, the output circuit 113 shown in FIG. 14 or the one shown in FIG. 15 may be used.

Figure 35:
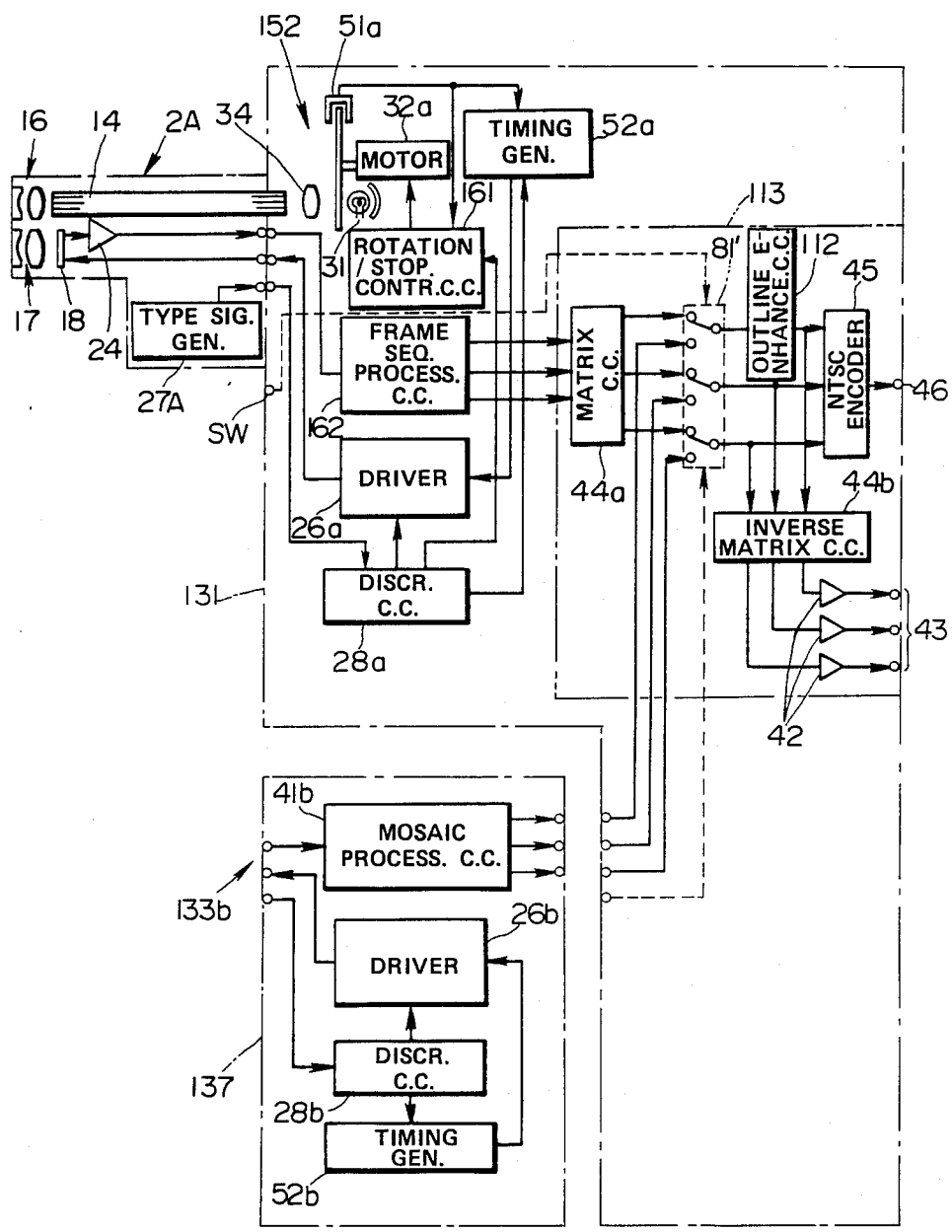
FIG. 35 is a formation diagram of an imaging apparatus in the eleventh embodiment.
Figure 36:
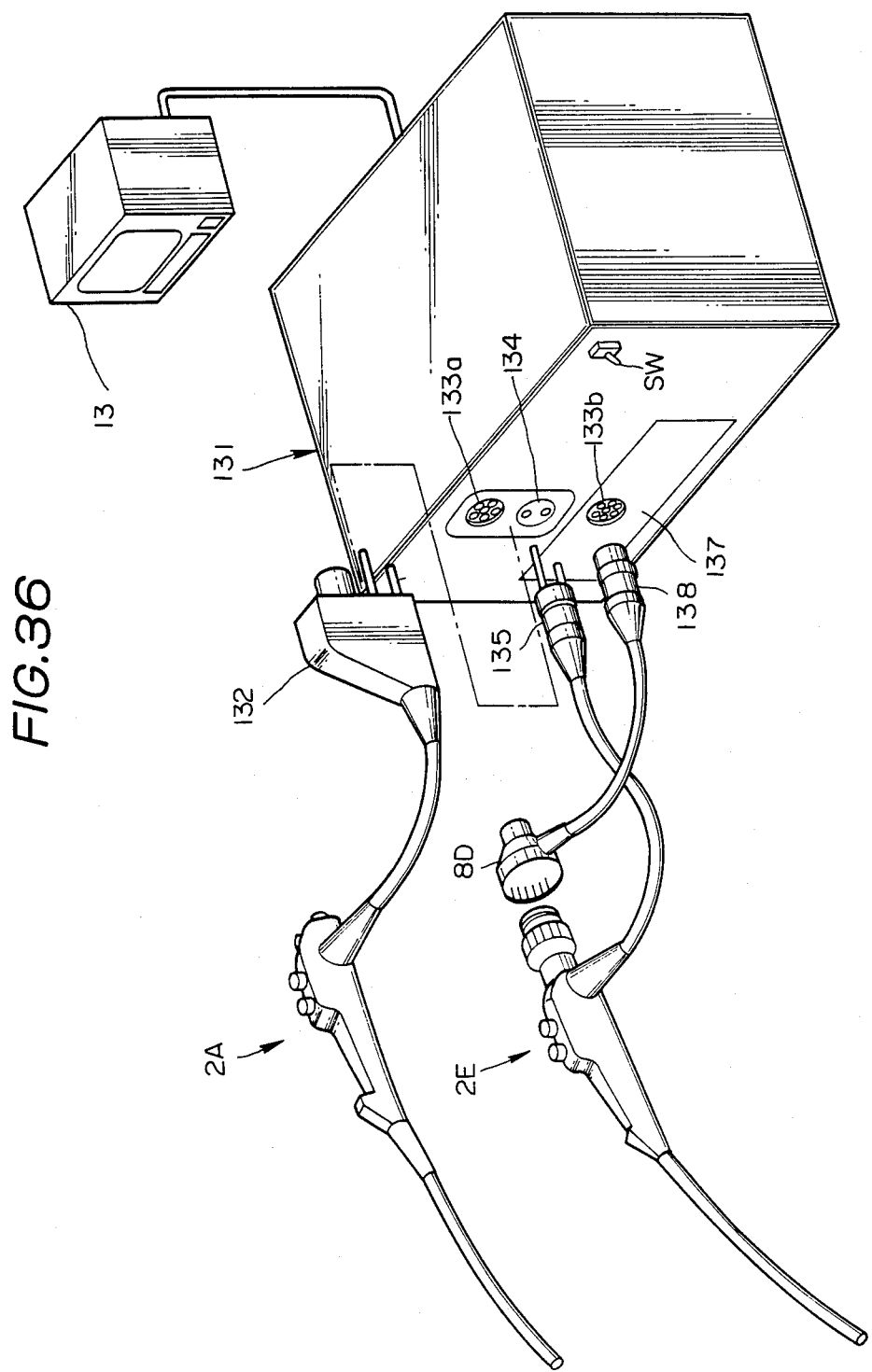
FIG. 36 is a perspective view showing an example of the system of the eleventh embodiment.

FIG. 35 shows the formation of the eleventh embodiment of the present invention and FIG. 36 shows the contour.

The imaging apparatus body 131 shown in FIG. 36 is provided with a light source connector receptacle 134 used in common with a frame sequential type signal connector receptacle 133a so that the connector 132 of the frame sequential type electronic scope 2A may be connected. The image is color-displayed by a color monitor 13. The connector (not illustrated) of the fiber scope 2C fitted with the frame sequential type TV camera can be used as connected to the above mentioned connector receptacles 133a and 134.

Also, in the case of the fiber scope 2E, its connector 135 is connected to the light source connector receptacle 134 so that an observation by a naked eye may be made.

The light source part inside the above mentioned light source connector receptacle 134 can normally output a white color light. When the rotary filter is rotated, a frame sequential illumination will be made.

When the frame sequential type connector is connected to the frame sequential type signal connector receptacle 133a, the rotary filter will be rotated by the type signal output in such case to make a frame sequential illumination.

Now, a recess is provided on the lower side on the front surface of the above mentioned imaging apparatus 131 so that the mosaic type preprocessor unit 137 may be plugged in and fitted. A mosaic type signal connector receptacle 133b is provided on the front surface of this mosaic type preprocessor unit 137. The signal connector 138 of the mosaic type TV camera 8D or the signal connector (not illustrated) of the mosaic type electronic scope 2B can be connected to this connector receptacle 133b.

As shown in FIG. 35, within the above mentioned imaging apparatus 131, the same light source part as is shown in FIG. 21 is contained and also the frame sequential processor is contained. This frame sequential type processor is substantially the same as is selected in case the switch 103 is switched to the frame sequential side in the processor shown in FIG. 21 and further on its output side is made an output circuit 113 provided with a function of processing the outline enhancing signal shown in FIG. 14.

The switching switch 81' within the output circuit 113 provided with this signal processing means will be switched when the mosaic type pre-processor unit 137 is plugged in.

According to this embodiment, if the mosaic type pre-processor unit 137 is acquired (bought) later as required, even the mosaic type scope can be used and the function of the apparatus can be economically expanded.

So that, even in case the above mentioned mosaic type pre-processor unit 137 is plugged in, the frame sequential type and mosaic type can be switched and used, a switching switch SW is provided, for example, on the front surface of the apparatus body 131 and the switching of this switching switch 81' can be controlled with this switch SW.

In the above mentioned tenth embodiment, the plug-in unit can be fitted on the front surface side. However, the mosaic type video processor unit or a part of it is fitted into an expanding slot provided on the rear side or the like so as to be used for the scope of either of the frame sequential type and mosaic type by the above mentioned switch SW or the like.

Figure 37:
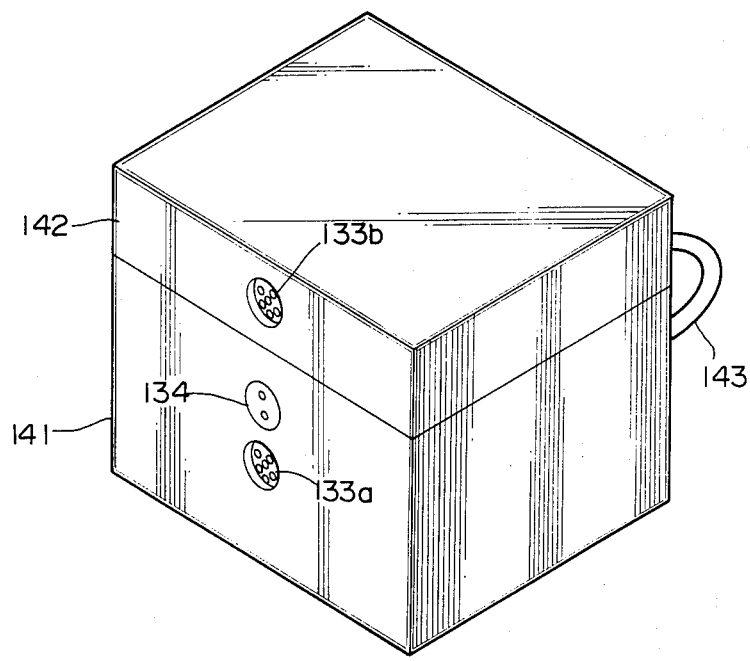
FIG. 37 is a perspective view showing a system of a modification of the eleventh embodiment.

Also, as shown in FIG. 37, a mosaic type video processor 142 is overlapped on the upper surface of an imaging apparatus body 141 provided with a signal processing means for the scope of the frame sequential type and a signal cable 143 from the mosaic type video processor 142 is connected to the connector receptacle of the imaging apparatus 141 so that the imaging apparatus 141 may be used for the scope of either system.

On the front surface of the imaging apparatus 141, such connector receptacles 133a and 134 are provided and, on the mosaic type video processor 142, a connector receptacle 133b is provided.

Figure 39:
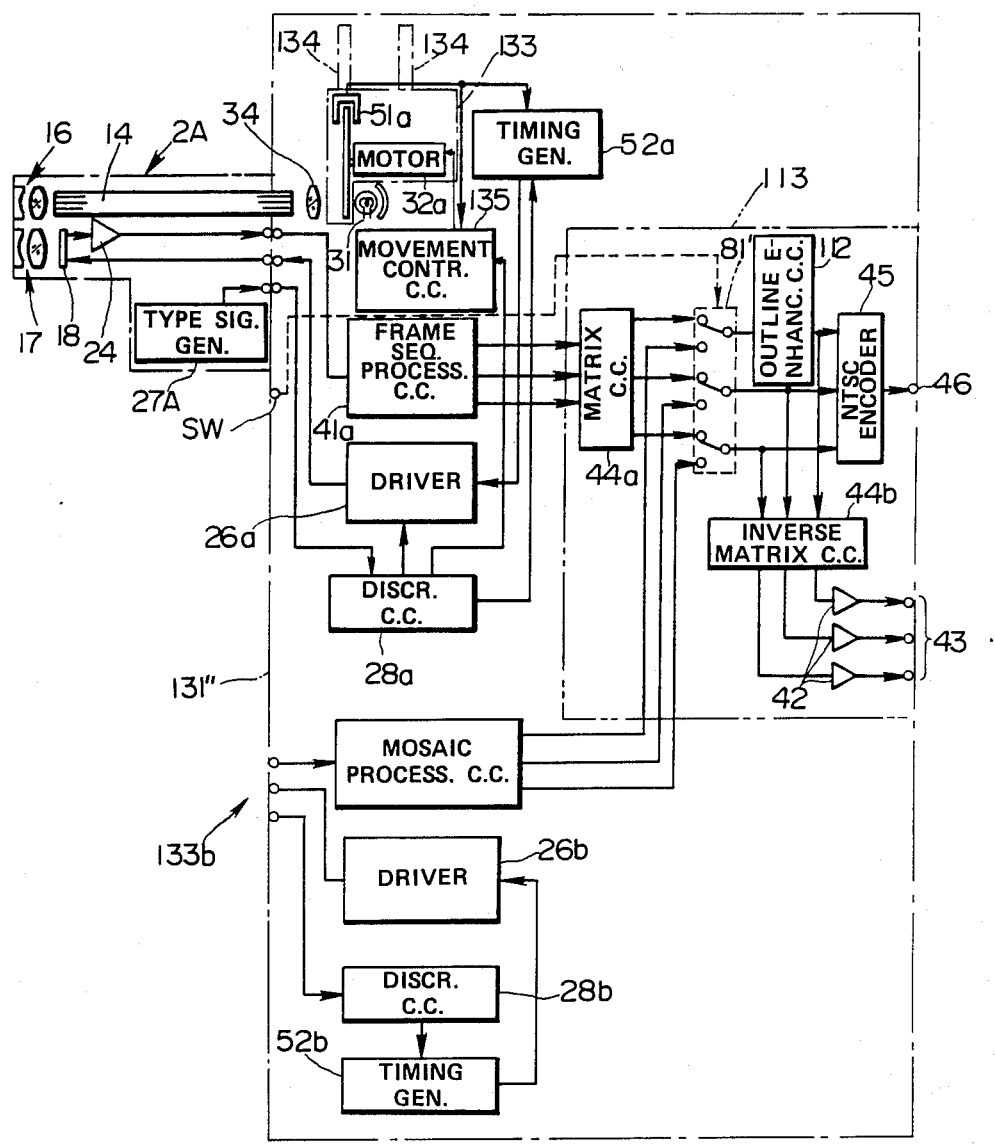
FIG. 39 is a formation diagram of an imaging apparatus in another modification of the eleventh embodiment.

The imaging apparatus of the formation shown in the above mentioned FIG. 35 may be made an imaging apparatus 131' made integral from the first and shown in FIG. 38. Also, in the imaging apparatus 131' shown in FIG. 38, the light source part shown, for example, in FIG. 18 may be used to make an imaging apparatus 132" shown in FIG. 39. In this case, the frame sequential type process circuit 41a shown, for example, in FIG. 2 is used. In the above mentioned FIGS. 38 and 39, the other signal than for enhancing the outline may be processed.

Further, in FIG. 35, drivers 26a and 26b and discriminating circuits 28a and 28b may be commonly used. The light source part shown in FIG. 35 may be replaced with another formation.

In the apparatus shown in FIG. 35, the frame sequential imaging apparatus 131 has a mosaic type unit 137 plugged in and fitted to be used. A frame sequential type unit can be fitted to the mosaic type.

Now, the number of pixels of the CCD22 of the TV camera 8C or 8D connected to the fiber scope 2E may be made larger than the number of pixels of CCD18 of the electronic scope 2A or 2B so that the resolution may be improved. In case the number of pixels of the TV camera 8C or 8D is thus made larger, a signal processing circuit means corresponding to the number of pixels in the case of the TV camera 8C or 8D may be provided.

Figure 40:
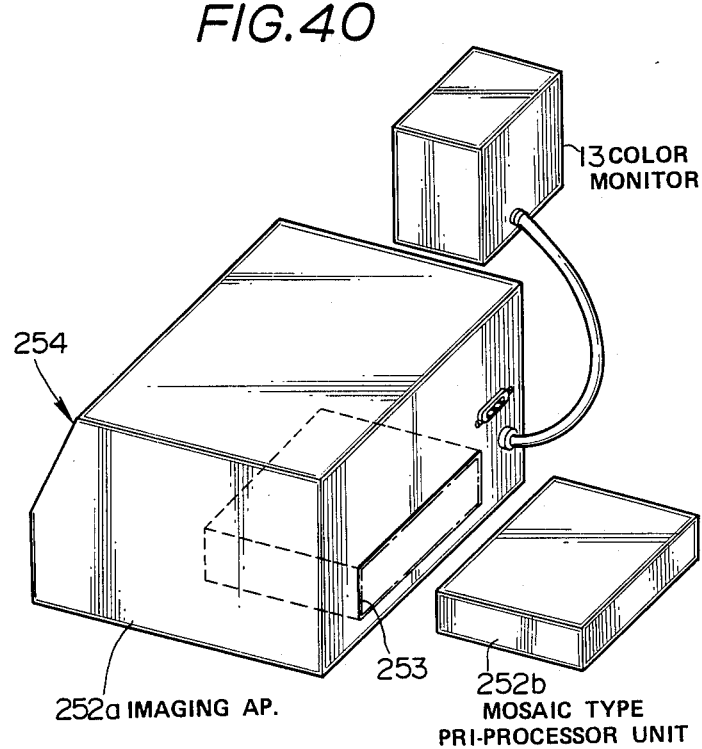
FIG. 40 is a perspective view showing an imaging apparatus in the twelfth embodiment of the present invention.

Now, in FIG. 36, the mosaic type pre-processor 137 can be fitted to the front surface side of the imaging apparatus 131. As shown in FIG. 40, the mosaic type pre-processor unit 252b may be fitted to the fitting part 253 provided on the rear surface side of the imaging apparatus 252a provided with a frame sequential signal processing means as shown in FIG. 40.

Figure 41:
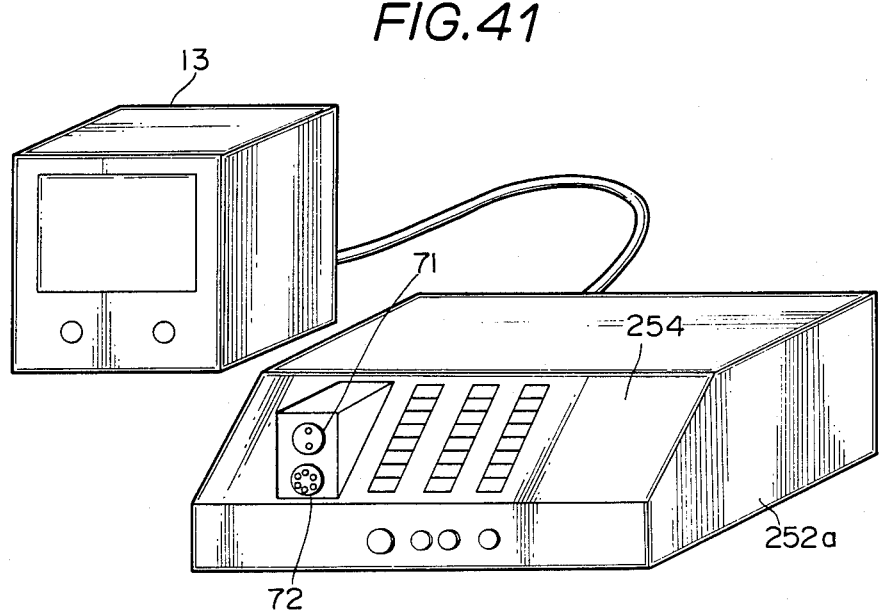
FIG. 41 is a perspective view as seen in a direction different from that in FIG. 40.

As shown in FIG. 41, on the front surface side of the imaging apparatus 252, a panel 254 is provided with a light source connector receptacle 71 and signal connector receptacle 72.

Figure 42:
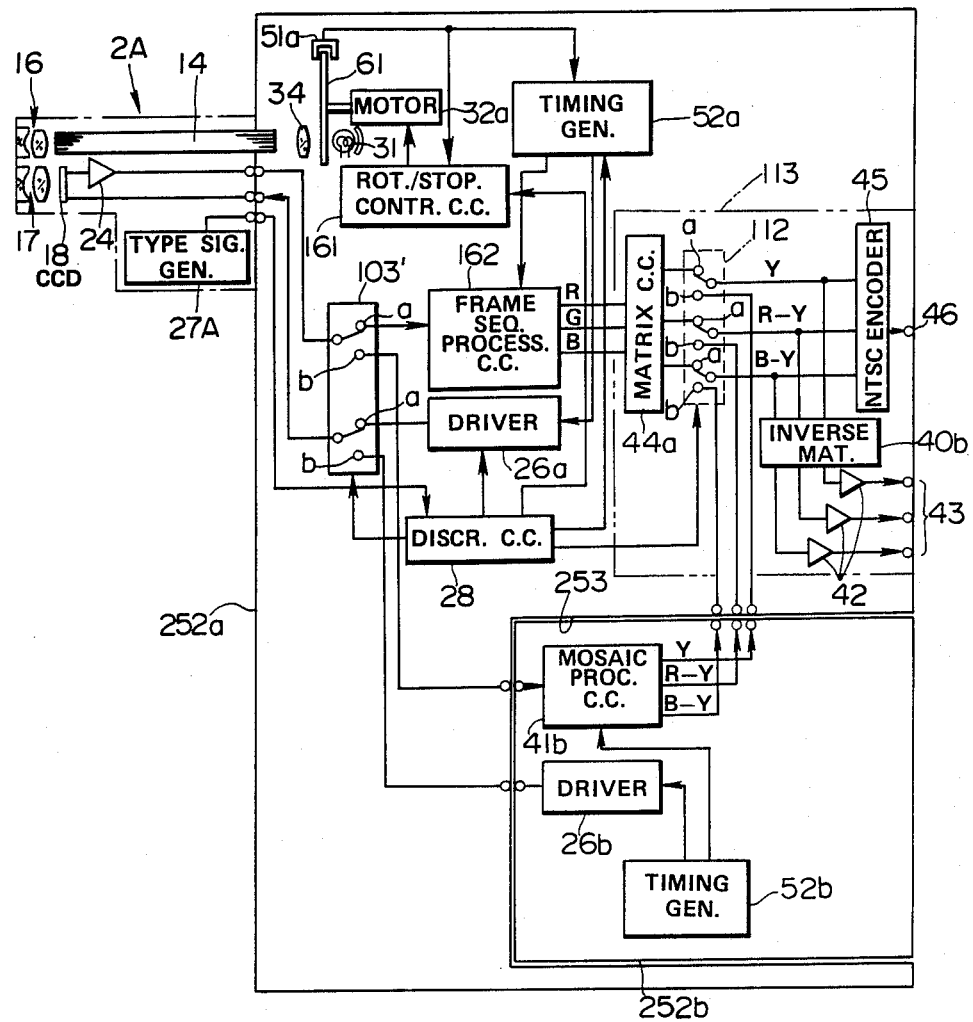
FIG. 42 is a formation diagram of an electronic system of the imaging apparatus of the twelfth embodiment.

The circuit formation of the above mentioned imaging apparatus 252a and mosaic type pre-processor unit 252b is shown in FIG. 42. This circuit formation is a combination of the one shown in FIG. 21 and the one shown in FIG. 35.

When the above mentioned imaging apparatus 252a is fitted with the mosaic type pre-processor unit (mosaic type unit) 252b, the imaging apparatus can be used for the mosaic type scopes 2B and 2D. That is to say, in this imaging apparatus 252a, normally the input signal switch 103' is held to be ON on the contact b side and the switch 81' within the output circuit 113 is also held to be ON on the contact b side. Therefore, when the mosaic type scope 2B or 2D is connected, a driving signal will be applied to the CCD19 through the switch 103' from the driver 26b and the signal read out by this application will be input into the mosaic type process circuit 316 through the switch 103'.

In this case, the discriminating circuit 28 will output a stopping control signal to the rotation/stop circuit 161 and the rotary filter 61 (shown in FIG. 10) will be held in the stopping state. Therefore, in this case, a white color light will be output.

On the other hand, when the frame sequential type scope 2A or 2C is connected, the frame sequential type will be identified by the discriminating circuit 28 and the switch 103' will be switched to be conductive on the contact a side. Also, the switch 44a will be switched to be selected on the contact a side.

The above mentioned discriminating circuit 28 applies a rotating control signal to the rotation/stop control circuit 161, rotates the rotary filter 61 fitted to the motor 32a and outputs a frame sequential light.

Figure 43:
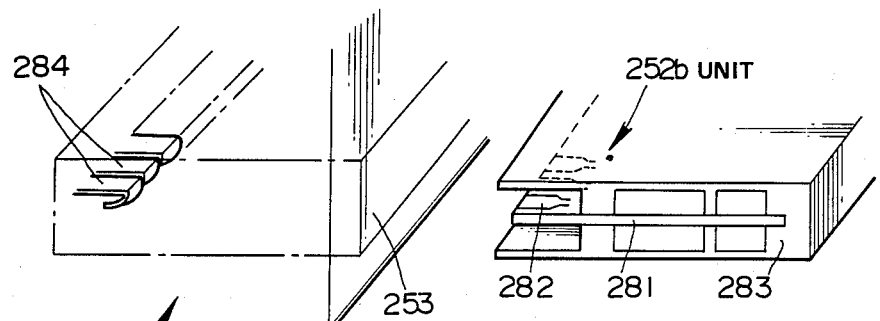
FIG. 43 is a perspective view showing a fitting port part in the twelfth embodiment.

Now, the structures of the above mentioned fitting part 253 and of the connecting part of the unit 252b fitted to this fitting part 253 are shown in FIG. 43.

The end part of a substrate 281 is present in the removably fitting side end part of a mosaic type unit 252b and is provided with connecting lands. Both upper and lower surfaces and the other end side of this substrate 281 are covered with a housing 283.

Figure 44:
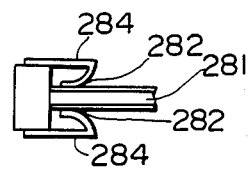
FIG. 44 is a side view showing a connecting part in the twelfth embodiment.

On the other hand, the fitting part 253 of the imaging apparatus 252a is provided in the deep part with connecting lead pieces 284 (only the upper side ones are shown in FIG. 43) which hold the lands 282 of the inserted unit 252b from both upper and lower sides as shown in FIG. 44 to hold the electric connection and fitted state.

When this unit 252b is fitted, the unit 252b may be flush with the rear surface of the imaging apparatus 252a, may somewhat project or may somewhat retreat.

According to the thus formed twelfth embodiment, in the case of first buying it, in case it can not be bought en bloc due to budget limitation, the frame sequential type scope apparatus, that is, the frame sequential type scope 2A or 2C (or both), frame sequential type imaging apparatus 252a and monitor 13 can be bought and used.

When the mosaic type unit 252b is bought, any scope can be used. This unit 252b can be simply fitted by being inserted into the fitting part 253.

Figure 45:
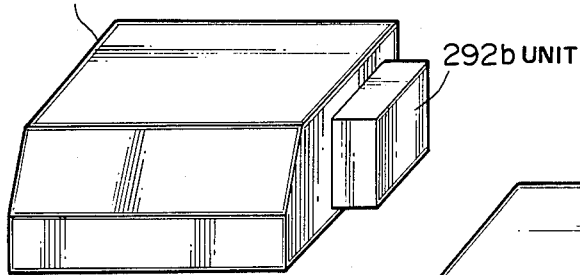
FIGS. 45 and 46 are perspective views each showing an imaging apparatus and a pre-processor unit fittable to this imaging apparatus in the thirteenth embodiment of the present invention.

FIG. 45 shows the thirteenth embodiment of the present invention.

In this embodiment, a mosaic type pre-processor unit 292b can be fitted to the side of a frame sequential type imaging apparatus 292a.

Figure 46:
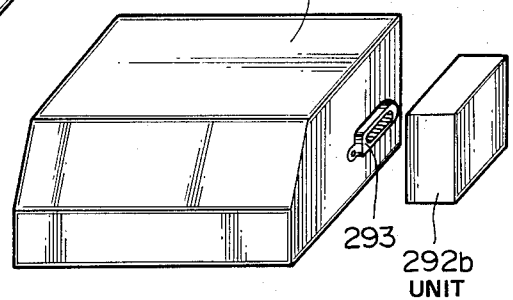

In this case, as shown in FIG. 46, a connector receptacle 293 is provided on the side of an imaging apparatus 292a. On the other hand, a connector to be removably fitted to the above mentioned connector receptacle 293 is provided on one surface. By fitting the connector to the above mentioned connector receptacle 293, both can be electrically connected and can be held as fitted.

The other parts than the connecting part are the same as in the above mentioned twelfth embodiment.

The operation and effect of this embodiment are substantially the same as in the above mentioned twelfth embodiment. The contour of the unit 292b may conform to the side shape of the imaging apparatus 292a.

Figure 47:
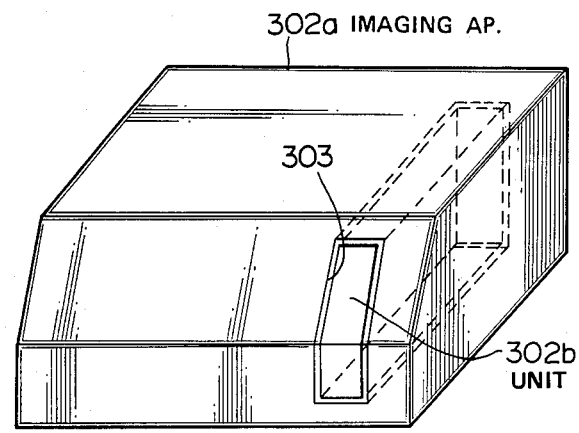
FIG. 47 is a perspective view showing an imaging apparatus of a structure fittable with a pre-processor in a modification of the thirteenth embodiment.

FIG. 47 shows a modification of the thirteenth embodiment of the present invention.

In the above mentioned twelfth embodiment, the unit 252b can be fitted to the rear surface of the imaging apparatus 252a but, in this modification, a fitting part 303 is provided in a position, for example, near one side part on the front surface of an imaging apparatus 302a and can be fitted with a mosaic type unit 302b.

Also, in this modification, in case the unit 302b is fitted, the rear surface (exposed to the panel side of the imaging apparatus 302a) of the unit 302b will be flush with the surface of the panel of the imaging apparatus 302a so as not to obstruct the appearance.

The operation and effect of this modification are substantially the same as in the above mentioned first embodiment.

Figure 48:
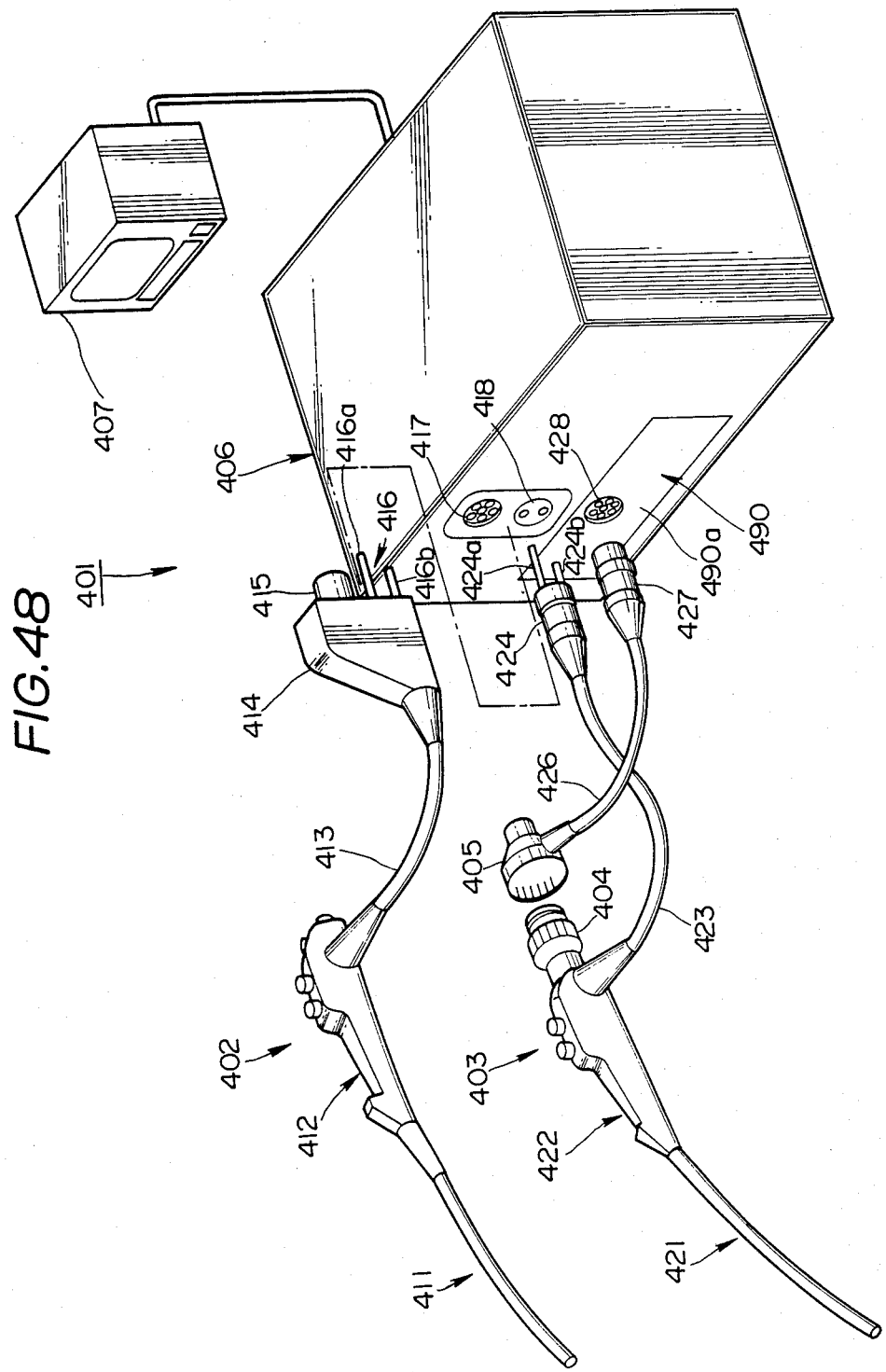
FIG. 48 is a perspective view showing a system of the fourteenth embodiment of the present invention.

FIG. 48 shows the fourteenth embodiment of the present invention.

As shown in FIG. 48, an endoscope system 401 of the fourteenth embodiment comprises a frame sequential type electronic endoscope 402, a fiber scope 403 having an image guide consisting of a fiber bundle as an image transmitting means, a mosaic type television camera 405 removably connected to an eyepiece part 404 of this fiber scope 403, a control apparatus (imaging apparatus) 406 containing a light source apparatus and video signal processing circuit and connected with the above mentioned electronic endoscope 402, fiber scope 403 and television camera 405 and a color CRT monitor 407 as a displaying means connected to this control apparatus 406.

In the above mentioned electronic endoscope 402, a thick operating part 412 is connected to the rear end of an elongate, for example, flexible insertable part 411. A flexible cable 413 is extended sidewise from the rear end of the above mentioned operating part 412 and is provided at the tip with a connector 414 provided integrally with an electric system socket 415 and illuminating system socket 416. The above mentioned illuminating system socket 416 is provided with an illuminating system terminal 416a and an air and water feeding system terminal 416b communicating with an air and water feeding channel not illustrated provided within the above mentioned insertable part 411. A frame sequential type electric system connector receptacle 417 and an illuminating system connector 418 to which the above mentioned electric system socket 415 and illuminating system socket 416 are respectively connected are provided, for example, on the front surface of the above mentioned control apparatus 406 so that the above mentioned electronic endoscope 402 may be connected to the control apparatus 406 by these sockets 415 and 416 and connector receptacles 417 and 418.

Not only the frame sequential system electronic endoscope 402 but also the frame sequential system television camera can be connected to the above mentioned frame sequential type electric system connector 417.

On the other hand, in the above mentioned fiber scope 403, the same as in the above mentioned electronic endoscope 402, a thick operating part 422 is connected to the rear end of an elongate, for example, flexible insertable part 421. A flexible cable 423 is extended sidewise from the rear end of the above mentioned operating part 422 and is provided at the tip with an illuminating system connector 424. The above mentioned illuminating system connector 424 is provided with an illuminating system terminal 424a and an air and water feeding system terminal 424b communicating with an air and water feeding channel not illustrated provided within the above mentioned insertable part 421. The above mentioned illuminating system connector 424 is to be connected to the above mentioned illuminating system connector receptacle 418. The above mentioned illuminating system connector 424 can be connected not only to the illuminating system connector receptacle 418 of the above mentioned control apparatus 406 but also to various light source apparatus 398 for the endoscopes of the light guide system as shown in FIG. 52.

A flexible cable 426 is extended sidewise from the above mentioned television camera 405 and is provided at the tip with an electric system connector 427. This electric system connector 427 is to be connected to a mosaic type electric system connector receptacle 428 provided adjacently below the above mentioned illuminating system connector receptacle 418 on the front surface, for example, of the above mentioned control apparatus 406.

Not only the above mentioned fiber scope 403 and television camera 405 but also the mosaic type electronic endoscope having a mosaic type solid state imaging device in the tip part of the insertable part can be connected to the above mentioned illuminating system connector receptacle 418 and mosaic type electric system connector receptacle 428.

Figure 49:
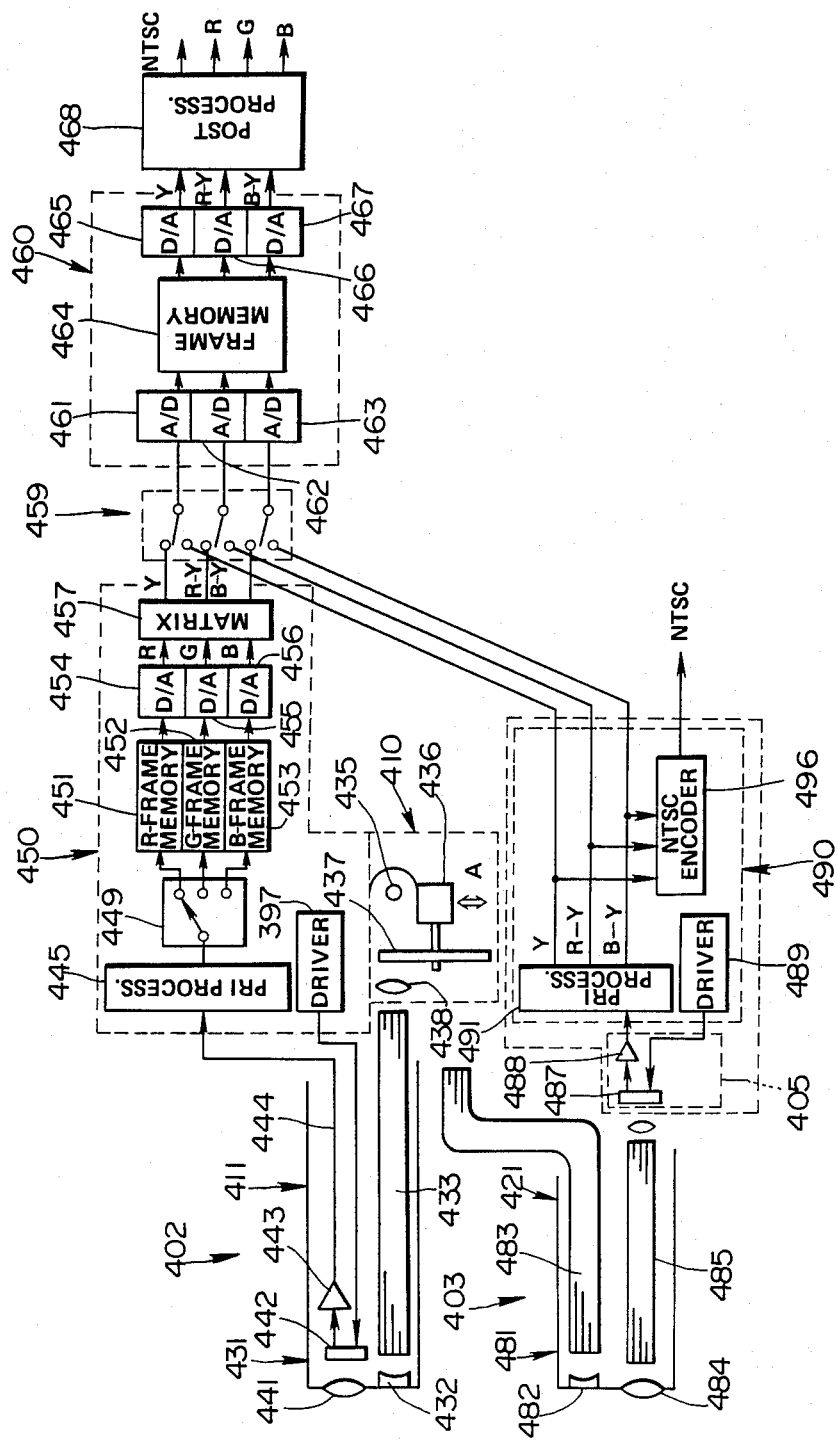
FIG. 49 is a formation diagram of a system of the fourteenth embodiment.

As shown in FIG. 49, a light distributing lens 432 is arranged in the tip part 431 of the insertable part 411 of the above mentioned electronic endoscope 432 and the exit end of a light guide 433 consisting of a flexible fiber bundle inserted through the above mentioned insertable part 411 is arranged on the rear end side of this light distributing lens 432. This light guide 433 is connected at the base end to the above mentioned illuminating system socket 416. When this connector 414 is connected to the connector receptacles 417 and 418 of the control apparatus 406, the illuminating light emitted from the light source apparatus 410 within the control apparatus 406 will be incident upon the above mentioned light guide 433. The above mentioned light source apparatus 410 is provided with a lamp 435 emitting a white light and a rotary color filter 437 having a red (R), green (G) and blue (B) three primary color transmitting filter and rotated by a motor 436. The illuminating light emitted from the above mentioned lamp 435 is made lights of the respective wavelengths of red, green and blue in turn, is condensed by a condenser lens 438 and is incident upon the above mentioned light guide 433. In this embodiment, the above mentioned rotary color filter 437 is movable in the direction indicated by the arrow A and is removably insertable between the above mentioned lamp 435 and condenser lens 438. The light incident upon the above mentioned light guide 433 is led to the above mentioned tip part 431 by this light guide 433, is emitted from the exit end of this light guide 433 and is radiated onto an object through the above mentioned light distributing lens 432.

Figure 50:
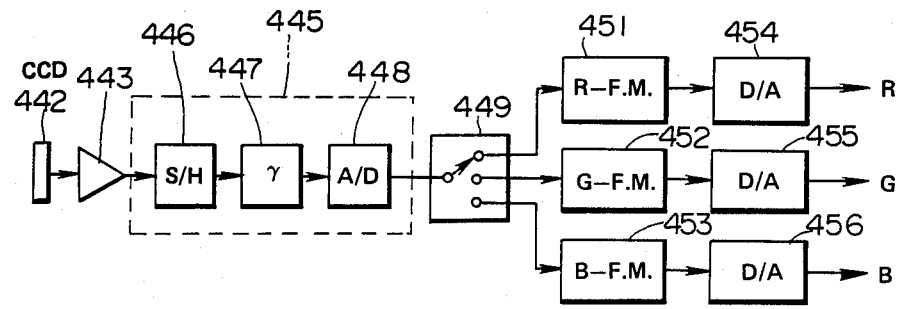
FIG. 50 is a formation diagram of a pre-process circuit in the fourteenth embodiment.

An image forming optical system 441 consisting of an objective or the like is provided in the tip part 431 of the above mentioned electronic endoscope 402. A solid state imaging device 442 as a CCD as an imaging means is arranged in the image forming position of this image forming optical system 441. This solid state imaging device 442 such is driven by a frame sequential system driver 397 within the above mentioned control apparatus 406. Returning lights corresponding to the respective color lights of red, green and blue from the above mentioned object are received by the above mentioned solid state imaging device 442 through the above mentioned image forming optical, system 441. The output signal of this solid state imaging device 442 is amplified by a pre-amplifier 443 provided within the above mentioned tip part 431 and is input into a frame sequential system video signal processing part 450 within the control apparatus 406 through a signal line 444 inserted through a cable 413, an electric system socket 415 of the above mentioned connector 414 and a frame sequential type electric system connector. In this video signal processing part 50, the output signal of he above mentioned solid state imaging device 442 is first input into such pre-process circuit 445 as in shown, for example, in FIG. 50. In this pre-process circuit 445, a video signal is extracted from the output signal of the above mentioned solid state imaging device 442 in a sample holding circuit 446, is γ-corrected in a γ-correcting circuit 447 and is then converted to a digital signal by an A/D converter 448. This digital signal is switched as synchronized with a color frame sequential illumination by a multiplexer 449 and is stored in an R frame memory 451, G frame memory 452 and B frame memory 453 corresponding to the respective colors of red, green and blue in turn. These frame memories 451, 452 and 453 are read out simultaneously at a velocity matching such displaying apparatus as a color CRT monitor 407, are converted to analogue signals respectively by D/A converters 454, 455 and 456 to produce R, G and B color signals. These R, G and B color signals are converted to a luminance signal Y and color difference signal R-Y and B-Y by a matrix circuit 457.

Figure 51:
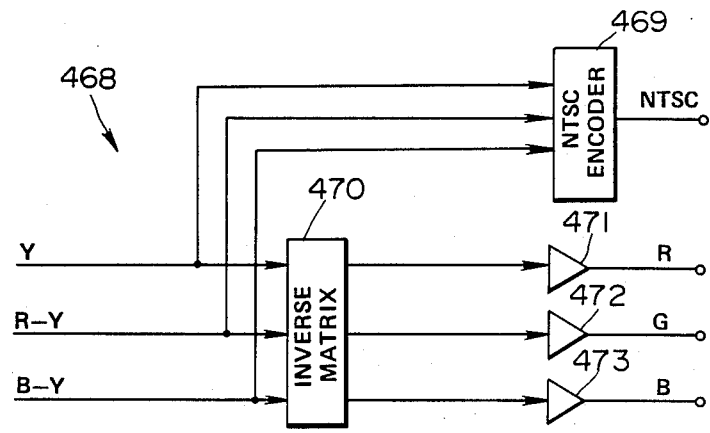
FIG. 51 is a formation diagram of a post-process circuit in the fourteenth embodiment.

The respective output ends of the luminance signal Y and color difference signals R-Y and B-Y of the above mentioned matrix circuit 457 are connected to one switching contact of the switching switch 459 and the above mentioned luminance signal Y and color difference signal R-Y and B-Y are input into a freezing part 460 through this switching switch 459. In this freezing part 460, the above mentioned luminance signal Y and color difference signals R-Y and B-Y are converted to digital signals respectively by A/D converters 461, 462 and 463 and are then stored in a frame memory 464. The digital signal red out of this frame memory 464 is converted to an analogue signal by D/A converters 465 and 466 and is input into such post-process circuit 468 as is shown, for example, in FIG. 51. In this post-process circuit 46, the luminance signal Y and color difference signals R-Y and B-Y are input into an NTSC encoder 469, is converted to an NTSC signal and is output. The above mentioned luminous signal Y and color difference signals R-Y and B-Y are input also into an inverse matrix circuit 470, are converted to R, G and B signals by this inverse matrix circuit 470 and are output respectively through drivers 471, 472 and 473. Thus, in this embodiment, the NTSC signal and R, G and B signals can be output. The above mentioned NTSC signal or R, G and B signals are input into the monitor 407 and an observed image is displayed.

In the above mentioned freezing part 460, at the time of freezing, data by one frame will be stored then, the writing into the above mentioned frame memory 464 will be stopped and a stationary picture image can be displayed in the monitor 407.

On the other hand, a light distributing lens 482 is arranged in the tip part 481 of the insertable part 421 of the above mentioned fiber scope 403 and the exit end of a light guide 483 consisting of a flexible fiber bundle inserted through the above mentioned insertable part 421 is arranged on the rear end side of this light distributing lens 481. This light guide 483 is connected at the base end to the above mentioned illuminating system connector 24. The illuminating light emitted from the light source apparatus 410 within the above mentioned control apparatus 406 is incident upon the above mentioned light guide 483. In case the illuminating system connector 424 of this fiber scope 403 is connected to the illuminating system connector receptacle 418 of the above mentioned control apparatus 406, the rotary color filter 437 of the light source apparatus 410 will be moved so as to retreat from the optical axis in the direction indicated by the arrow A and the white illuminating light emitted from the lamp 435 will be incident upon the above mentioned light guide 483 without passing through the above mentioned rotary color filter 437. The light incident upon the above mentioned light guide 483 is led by this light guide 483, is emitted from the exit end of this light guide 483 and is radiated onto an object through the above mentioned light distributing lens 482.

An image forming optical system 483 consisting of an objective or the like is provided in the tip part 481 of the above mentioned fiber scope 403. The tip surface of an image guide 485 consisting of a fiber bundle inserted through the insertable part 421 is arranged in the image forming position of this image forming optical system 484. The observed image formed by the above mentioned image forming optical system 484 is led to the eyepiece part 404 by the above mentioned image guide 485 so as to be observed by this eyepiece part 404. The above mentioned observed image can be imaged by connecting the television camera 405 to this eyepiece part 404.

The above mentioned television camera 405 is provided with a solid state imaging device 487 arranged in the image forming position of the above mentioned eyepiece part 404 and a pre-amplifier 488 amplifying the output signal of this solid state imaging device 487. A filter array not illustrated in which color filters transmitting respectively such color lights such as R, G and B are arranged in the form of a mosaic or the like is provided on the front surface of the above mentioned solid state imaging device 487. The above mentioned solid state imaging device 487 is driven by a mosaic type driver 489 within the control apparatus 406. The output signal of the above mentioned solid state imaging device 487 is amplified by the above mentioned pre-amplifier 488 and is input into a mosaic type video signal processing part 490 within the control apparatus 406. In this video signal processing part 490, the output signal of the above mentioned solid state imaging device 487 is first input into a pre-process circuit 491 of the same formation as of the process circuit 41b shown, for example, in FIG. 8.

The luminance signal Y and color difference signals R-Y and B-Y produced by this pre-process circuit 491 are input into an encoder 496 and are converted to an NTSC signal to be output. The respective output ends of the above mentioned luminance signal Y and color difference signals %-Y and B-Y of the above mentioned pre-process circuit 491 are connected to the other switching contacts of the above mentioned switch 459. The above mentioned luminance signal Y and color difference signals R-Y and B-Y are input into the above mentioned freezing part 460 through this switching switch 459. That is to say, in this embodiment, the above mentioned freezing part 460 and post-process part 468 are commonly used by the frame sequential system electronic endoscope 402 and mosaic type television camera 405. By switching the above mentioned switching switch 459 from the above mentioned post-process circuit 468, the video signal of the observed image by the above mentioned electronic endoscope 402 and the video signal of the observed image imaged by the above mentioned fiber scope 403 and television camera are switched and output.

Now, in this embodiment, as shown in FIGS. 48 and 52, the above mentioned mosaic type video signal process part 490 is contained within a housing 490a, is made a unit removably fitted to the control apparatus 406 and can be used with only the mosaic type imaging means. This unit video signal process part 490 can be removably inserted into the above mentioned control apparatus 406 from the front surface side. When it is fitted to the control apparatus 406, the respective output ends of the luminance signal Y and color difference signals R-Y and B-Y of the pre-process circuit 491 will be connected to the switching contacts of the switching switch 459. Also, the mosaic type electric system connector receptacle 428 is provided on the front surface of the housing 490a of the above mentioned mosaic system video signal processing part 490a.

Therefore, as shown in FIG. 52, when the illuminating system connector 424 of the fiber scope 403 is connected to the light source apparatus 398 for the light guide system endoscope and the electric system connector 427 of the television camera 405 connected to the eyepiece part 404 of this fiber scope 403 is connected to the electric system connector receptacle 428 of the above mentioned video signal processing part 490, an NTSC signal will be output from the above mentioned video signal processing part 490 and the observed image imaged by the mosaic system can be displayed in the monitor 407.

Thus, in this embodiment, there are provided the frame sequential system electronic endoscope 402, fiber scope 403 and mosaic type television camera 405 connected to the eyepiece part 404 of this fiber scope 403 and the control apparatus 406 to which they are connected. Within the above mentioned control apparatus 406, there are provided the light sources apparatus 410 which can feed a frame sequential illuminating light adapted to the above mentioned electronic endoscope 402 and a white illuminating light adapted to the above mentioned television camera 405, frame sequential system video signal processing part 450 and mosaic type video signal processing part 490. Therefore, both of the electronic endoscope 402 which is a frame sequential system imaging means and the television camera 405 connected to the fiber scope 403 which is a mosaic type imaging means can be used.

Further, the above mentioned mosaic type video signal processing part 490 is made a unit removably fitted to the control apparatus 406 and can be used with only the mosaic type imaging means. Therefore, the television camera 405 connected to the fiber scope 403 which is a mosaic type imaging means can be used even alone.

FIG. 53 is a perspective view of a control apparatus relating to the fifteenth embodiment of the present invention.

In this embodiment, the mosaic type video signal processing part 490 can be removably fitted to the upper part of the other part of the control apparatus 406. When it is mounted on the upper part of the other part of the control apparatus 406, the respective output ends of the luminance signal Y and color difference signals R-Y and B-Y of the pre-process circuit 491 will be connected to the switching contacts of the switching switch 459.

The other formations, operations and effects are the same as in the fourteenth embodiment.

Figure 54:
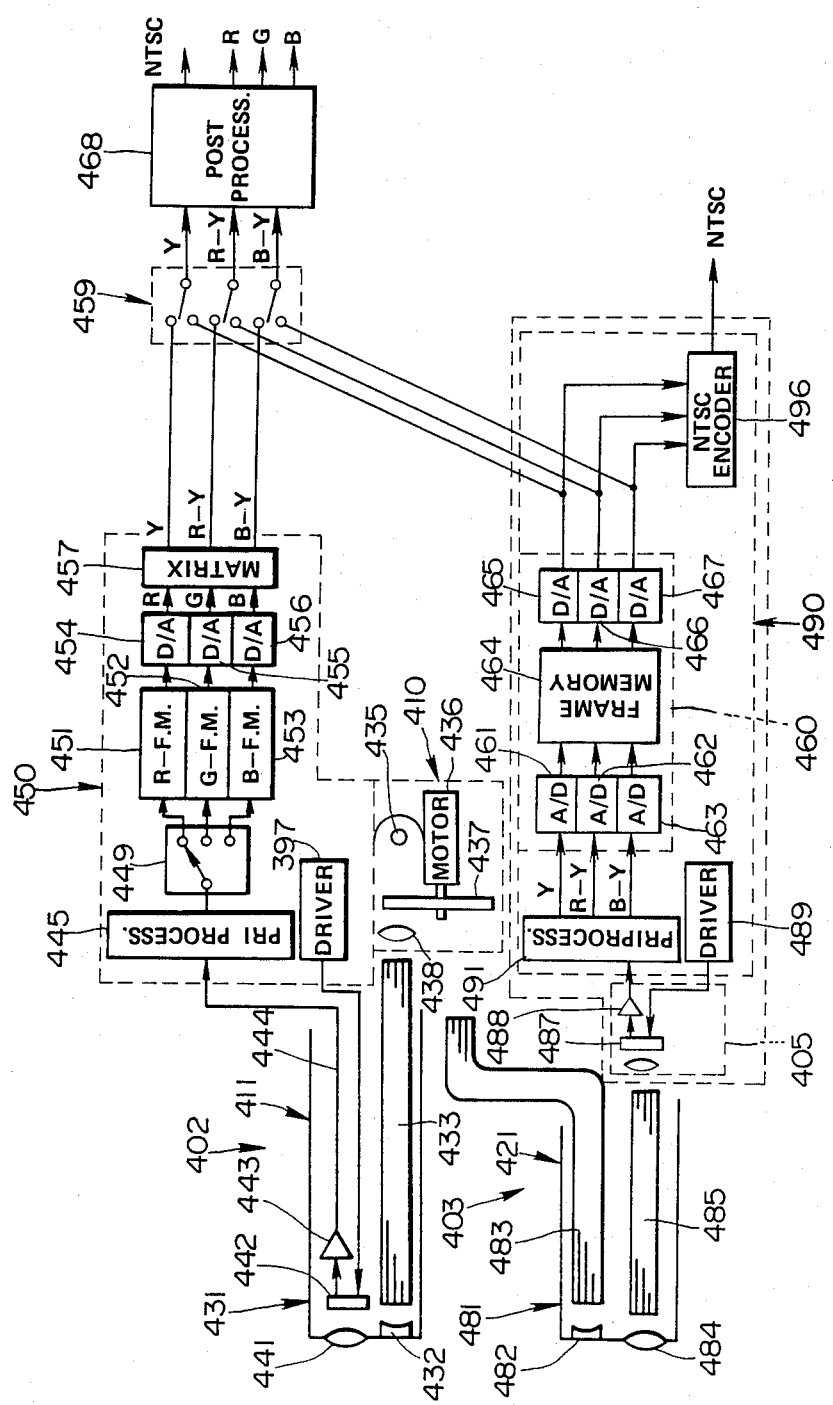

FIG. 54 is a block diagram showing the formation of an endoscope system relating to the sixteenth embodiment of the present invention.

In this embodiment, the freezing part 460 within the control apparatus 406 is not provided between the switching switch 459 and post-process 468 but is provided within the mosaic type video signal processing part 490. That is to say, the luminance signal Y and color difference signals R-Y and B-Y are output to the NTSC encoder 499 and the above mentioned switching switch 459 through the above mentioned freezing part 460. The other formations are the same as in the fourteenth embodiment.

According to this embodiment, even in case the television camera 405 connected to the fiber scope 403 which is a mosaic type imaging means is used alone, by using the above mentioned freezing part 460, the NTSC signal can be frozen and a stationary picture image can be displayed.

In case a frame sequential type imaging means is used, a stationary picture image can be displayed by using the frame memories 451, 452 and 453 within the frame sequential type video signal processing 450.

The other operations and effects are the same as in the fourteenth embodiment.

The present invention is not limited to the above mentioned embodiment. For example, the frame sequential system imaging means may be the frame sequential type television camera connected to the eyepiece part 404 of the fiber scope 403. The mosaic type imaging means may be the electronic endoscope provided with the mosaic type solid state imaging device in the tip part of the insertable part.

In case the frame sequential type and mosaic type commonly use the light source apparatus 410, the connector receptacles may be separately provided to move the lamp. The rotary color filter 437 may be provided with a transparent part so that, in case the mosaic type imaging means is used, the white light emitted from the lamp 435 may be incident upon the light guide 483 through this transparent part. Also, the light source apparatus for the frame sequential type and for the mosaic type may be separately provided.

The electric system connector receptacle nd illuminating system connector receptacle may be respectively common or separate.

Further, the frame sequential type video signal processing part 450 or both of the frame sequential type video signal processing part 450 and mosaic type video signal processing part 490 may be removably fitted to the control apparatus 406. The removably fitting means is not limited to the ones shown in the fourteenth and fifteenth embodiments. There can be used such various means as, for example, removably connecting both video signal processing parts 450 and 490 on the right and left.

The frame sequential system and mosaic system video signal processing circuits are not limited to the partly used in common as in the above mentioned embodiment but may be separately provided.

Further, not only the monitor 407 but also a picture image file, monitor type still camera and video tape recorder may be connected to the control apparatus 406.

Figure 55:
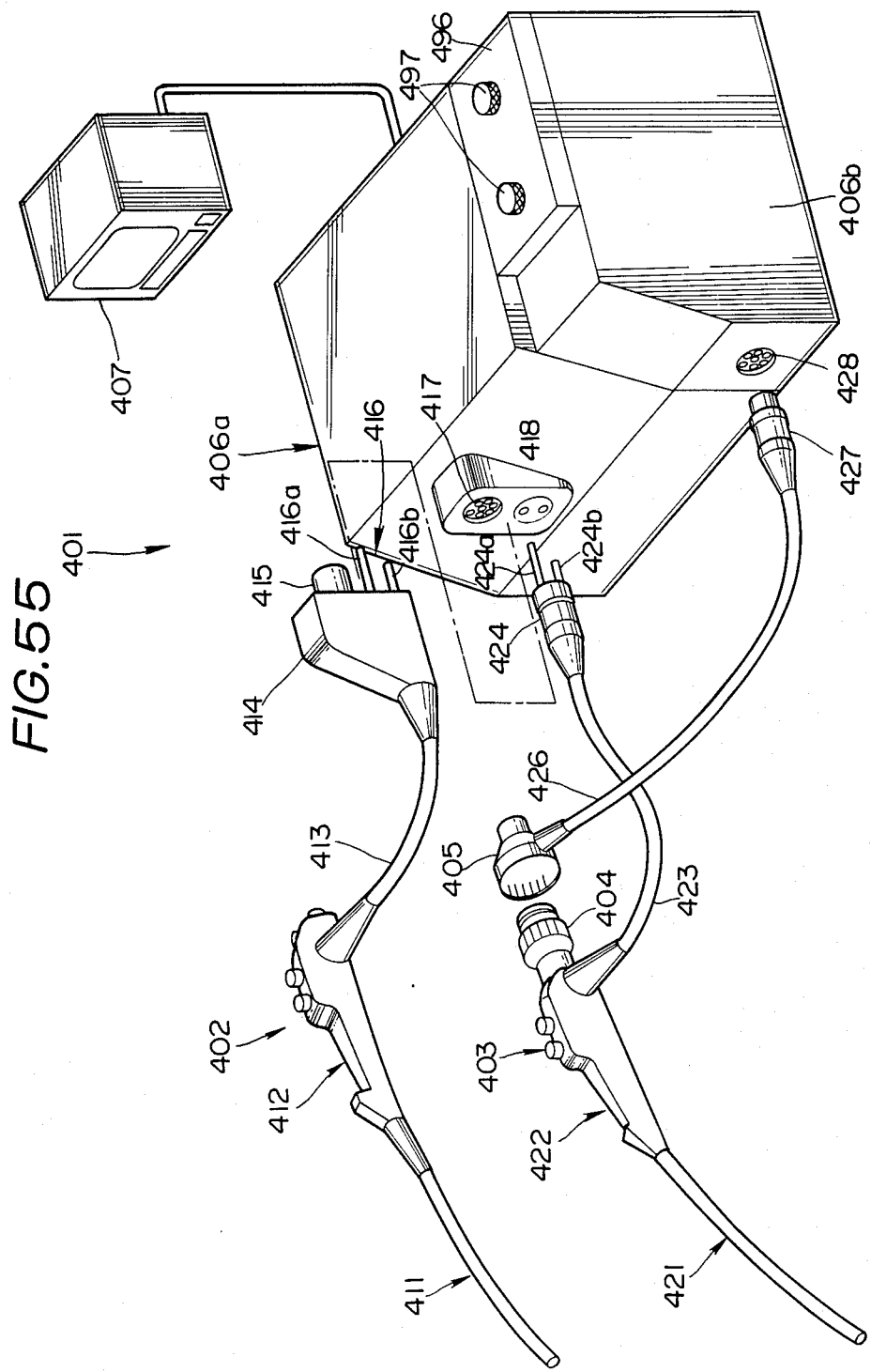
FIG. 55 is a perspective view of a system of the seventeenth embodiment of the present invention.

In the system of the seventeenth embodiment of the present invention shown in FIG. 55, the mosaic type control apparatus unit 406b is to be fitted to the side of the frame sequential type control apparatus 406a.

In this system, the mosaic type video processing part 490 is made fittable to the side of the control apparatus 406 in the system 401 shown in FIG. 48. The structure of the fitting part is shown in FIG. 56.

Figure 56:
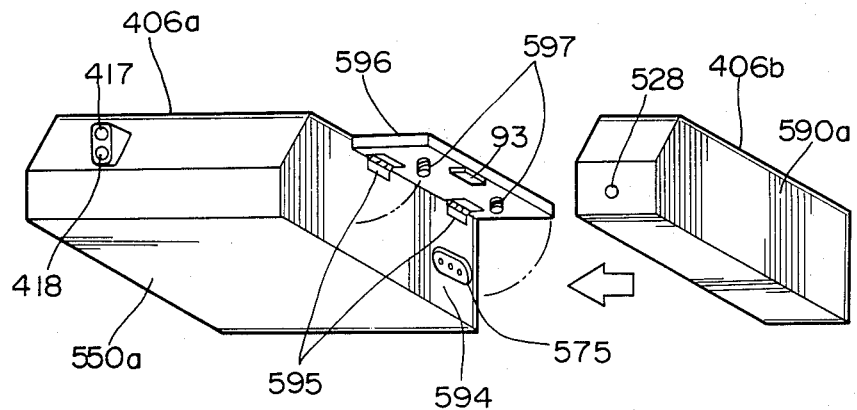
FIG. 56 is a perspective view showing that the control apparatus in the seventeenth embodiment is of a detachable structure.

That is to say, in this embodiment, as shown in FIGS. 55 and 56, a housing 550a containing the above mentioned frame sequential type video signal processing part 450a is provided with lid 596 on one side plate so as to be opened upward by hinges 595 which are opening and closing members. Further, as in FIG. 55, the frame sequential type housing 550a and the mosaic type housing 590a are removably fitted by screwing fixing screws 597 as jointing means provided rotatably on the above mentioned lid 596 so as not to drop off into female screw-parts provided on the upper surface of the housing 590a containing the mosaic type video signal processing part 490.

A connector receptacle 575 electrically connecting the frame sequential type control apparatus 406a and mosaic type control apparatus 406b is provided on the side plate 594 to which the frame sequential type housing 550a and mosaic type housing 590a are jointed. A connector receptacle 576 is provided on the side plate of the mosaic type housing 590a corresponding to the above mentioned connector receptacle 575. By doing this, the mosaic type housing 590a can be jointed to the frame sequential type housing 550 and at the same time the circuits can be connected.

Figure 57:
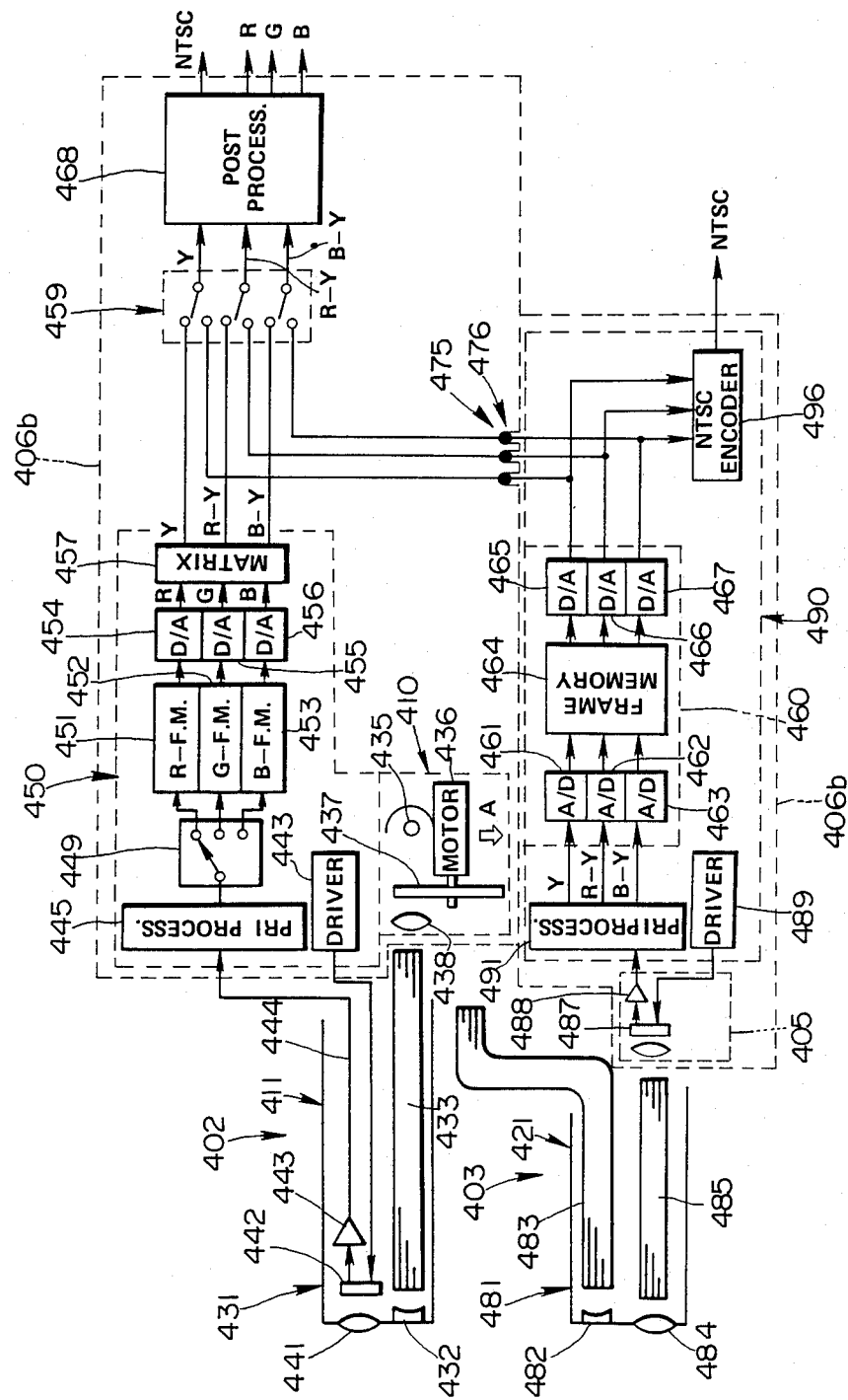
FIG. 57 is a formation diagram of a system of the seventeenth embodiment.

As shown in FIG. 57, the formation of the electric system of the system of this embodiment is substantially the same as in shown in FIG. 49.

According to this embodiment, the housings 550a and 590a can be fitted simply and positively. In the case of using only the frame sequential type control apparatus 406a, if the lid 496 is made to fall on the side plate 494 side, it will not be in the way and, even in case the mosaic type control apparatus 406b is jointed, the unit fitting structure is good in the appearance.

Figure 58:
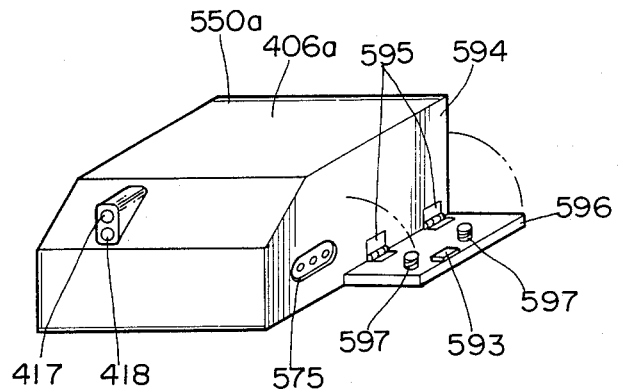
FIG. 58 is a perspective view showing a jointing device of a control apparatus in a modification of the seventeenth embodiment.

FIG. 58 is a perspective view of a formation showing a jointing means of a frame sequential type control apparatus relating to a modification of the seventeenth embodiment of the present invention.

In this modification, the housing 550a containing the above mentioned frame sequential type video signal processing part 450 is provided on one side plate with a lid 596 so as to be opened downward by hinges 595 which are opening and closing members. Further, the frame sequential type housing 550a and the mosaic type housing 590a are removably fitted by screwing fixing screws 597 as jointing means provided rotatably on the above mentioned lid 596 so as not to drop off into female screw parts provided on the lower surface of the housing 5909a containing the mosaic type video signal processing part 490. The lid 596 is provided with a magnet 593 which can attract the side plate 594 of the housing 550a made, for example of a metal so that, in case the mosaic type control apparatus 406b is not jointed, the lid 96 may be fixed to the side plate 594.

The other formations are the same as in the seventeenth embodiment.

Figure 59:
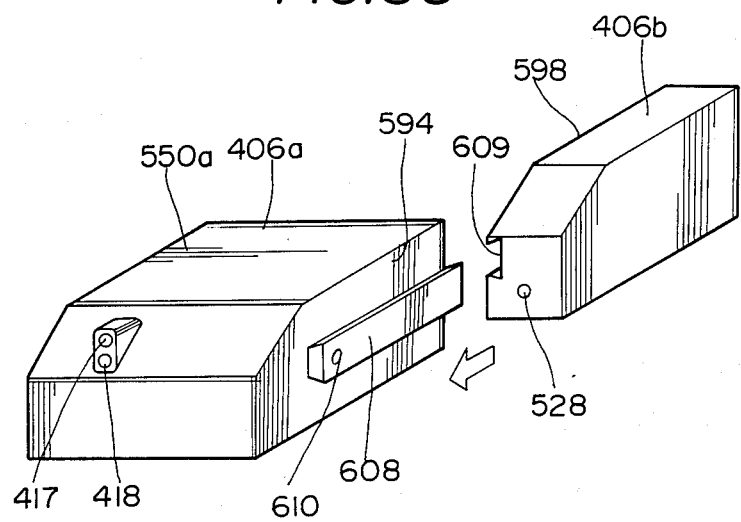
FIG. 59 is a perspective view showing a jointing device of a control apparatus in the eighteenth embodiment of the present invention.

FIG. 59 is a perspective view of a formation showing a jointing means of a frame sequential system control apparatus relating to the eighteenth embodiment of the present invention.

In this embodiment, a projection 608 expanding to the tip part on the front surface from the rear surface of the above mentioned control apparatus 406 is provided on one side plate 594 of the housing 550a of the frame sequential type control apparatus 406a and a recess 609 fitting the above mentioned projection is provided on the side plate 598 of the housing 590a of the mosaic type control apparatus 406b corresponding to the frame sequential type control apparatus so that the frame sequential type control apparatus 406a and mosaic type control apparatus 406b may be fitted and jointed to each other.

A clicking device 610 is provided on the tip surface of the above mentioned projection 608 so that the frame sequential type control apparatus 406a and mosaic type control apparatus 406b may be jointed in a predetermined position and further may be electrically connected at the jointing time point.

The other formations are the same as in the seventeenth embodiment.

Figure 60:
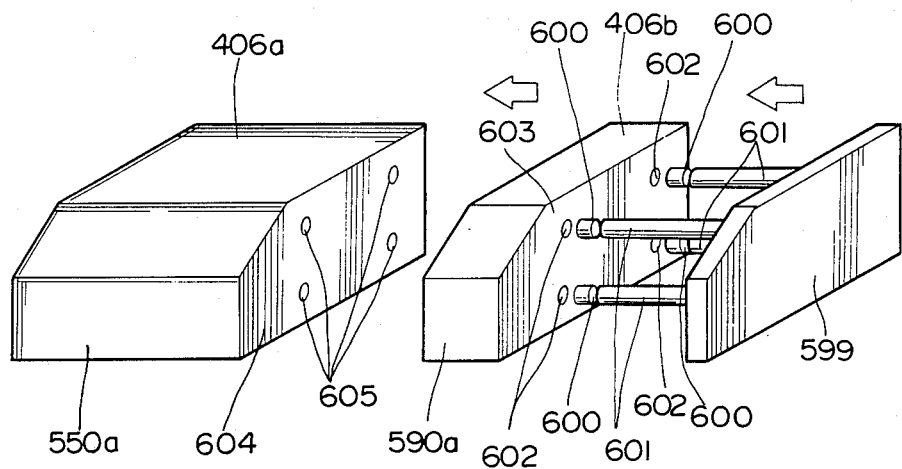
FIG. 60 is a perspective view showing a jointing device of a control apparatus in the nineteenth embodiment of the present invention.
Figure 61:
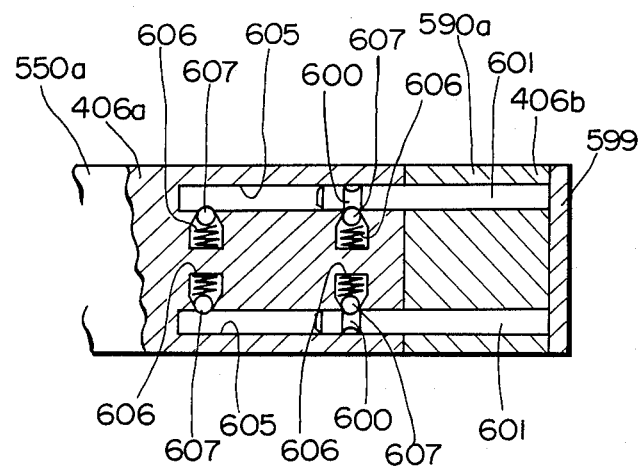
FIG. 61 is a sectioned view showing as magnified a jointing part in the nineteenth embodiment.

FIG. 60 relates to the nineteenth embodiment of the present invention and shows a jointing means of the frame sequential type control apparatus and mosaic type control apparatus. Bars 602 each having a peripheral groove 600 near the tip are provided on one side of a lid 599 of the same shape as of the sides 603 and 604 of the frame sequential type and mosaic type housings 550a and 590a. Through holes 602 and bottomed holes 605 are provided respectively on the side 603 of the housing 590a of the mosaic type control apparatus 406b corresponding to the above mentioned bars 601 and on the side 604 of the housing 550a of the frame sequential type control apparatus 406a. Balls 607 energized by springs 606 are provided respectively in the position reached by the groove 600 of the bar 601 when the mosaic type housing 590a is inserted as shown in FIG. 61 in the above mentioned bottomed hole 605 and in the position reached by the groove 600 of the bar 601 when the mosaic type housing 590a is not inserted but the lid 599 is jointed to the housing 550a. When the bar 601 is inserted in the bottomed hole 605, the bar 601 will enter the hole against the energizing force of the spring 606. When the ball 607 reaches the position of the groove 600, the ball 607 will fit in the groove 600 and the lid 599 will be fixed.

The other formations are the same as in the seventeenth embodiment.

Now, in the system of each of the above described embodiments, a fiber scope is used as an optical endoscope but a rigid endoscope can be used the same.

For example, in the system 1 of the first embodiment, not only the fiber scope 2E and the fiber scopes 2C and 2D fitted with TV cameras but also the rigid endoscope 752F shown in FIG. 2, the rigid endoscope 752G fitted with the frame sequential TV camera 753 or mosaic type TV camera 754 in the rigid endoscope 752F and the rigid endoscope 752H fitted with the mosaic type TV camera can be used.

Figure 63:
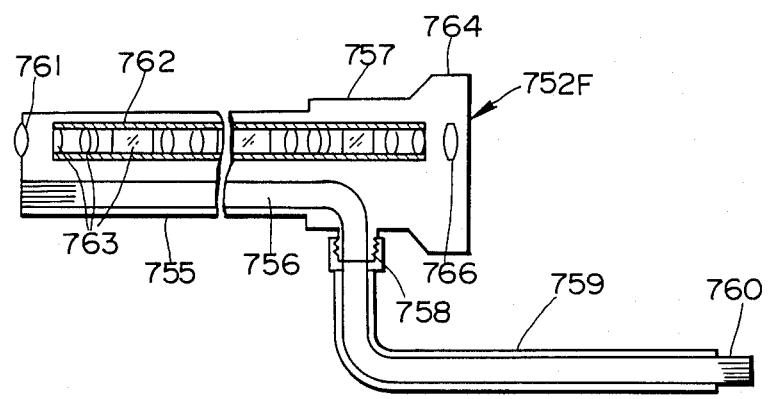
FIG. 63 is a formation view showing a schematic structure of a rigid endoscope.

In the above mentioned rigid endoscope 752F, as shown in FIG. 63, a light guide 756 is inserted through a rigid insertable part 755 and is fixed at the end on the base side with a light guide mouthpiece 758 of a holding part 757. A light guide cable 759 can be connected to this light guide mouth piece 758, has a light guide connector 760 formed, transmits the illuminating light fed from the light source part to the light guide 756 and emits it from the exit end surface on the tip side of the insertable part 755. The object illuminated by the illuminating light emitted from this exit end surface is made to form an image in the focal plane by an objective 761 fitted to the tip part. The optical image formed by this objective is transmitted to the exit end side on the eyepiece part 164 side by a relay optical system 763 fitted through a rigid lens tube 762 and can be observed with a naked eye through an eyepiece arranged within an eyepiece part 764. When a removable TV camera 753 or 754 is fitted to this eyepiece part 764, the image can be formed in the imaging plane of a CCD 767 by an image forming lens 766. A color separating mosaic filter 768 is fitted to the imaging surface of the CCD 767 in the mosaic type TV camera 754.

Signal cables 769 are connected from the above mentioned TV cameras 753 and 754 and are fitted at the ends respectively with signal connectors 770G and 770H.

The TV cameras 753 and 754 contain respectively type signal generating circuits 771G and 771H (abbreviated as T.S.G.) which output type signals respectively indicating the frame sequential type and mosaic type color imaging means.

The rigid endoscope 752F or rigid endoscopes 752G and 152H fitted respectively with the frame sequential type TV camera 753 and 754 can be applied also to the other embodiments by changing the connector 760 or 770G and 770H.

In the above described embodiments, there can be provided a correcting circuit means correcting the temperature dependency of the light emitting characteristics of the light source lamp 31 or the like.

Different embodiments can be formed by combining parts of the above described respective embodiments and belong also to the present invention.

As described above, according to the present invention, a signal processing means processing the signals corresponding respectively to color imaging scopes of different systems is formed to display the images by a color monitor and therefore scopes of different types can be used.

What is claimed is:

1. A endoscope imaging system comprising:
   a color imaging means provided with a color filter using a solid state imaging device fitted with a color separating color filter in front of an imaging part having a photoelectric converting function;
   a frame sequential type color imaging means using a solid state imaging device not fitted with said color separating color filter in front of an imaging part having a photoelectric converting function;
   a light output means and signal processing means either of which is provided with functions corresponding to said color imaging means provided with said color filter and said frame sequential type color imaging means; and
   a color monitoring means color-displaying predetermined color video signals output from said signal processing means.

2. An endoscope imaging system comprising:
   a color imaging means provided with a color filter using a solid state imaging device fitted with a color separating color filter in front of an imaging part having a photoelectric converting function;
   a light output means outputting a white light corresponding to said color imaging means provided with said color filter;
   a signal processing means provided with a function of processing the signal corresponding to said color imaging means provided with said color filter and a function of processing the signal corresponding to a frame sequential type color imaging means; and
   a color monitoring means color-displaying predetermined color video signals output from said signal processing means.

3. An endoscope imaging system comprising:
   a color imaging means provided with a color filter using a solid state imaging device fitted with a color separating color filter in front of an imaging part having a photoelectric converting function;
   a light outputting means provided with a function of outputting a white light corresponding to said color imaging means provided with said color filter and a function of outputting a frame sequential light in wavelength ranges different from each other in time series;

a signal processing means processing the signal corresponding to said color imaging means provided with said color filter; and
a color monitoring means color-displaying predetermined color video signals output from said signal processing means.

4. An endoscope imaging system comprising:
a frame sequential type color imaging means using a solid state imaging device not fitted with a color separating color filter in front of an imaging part having a photoelectric converting function;
a light outputting means outputting frame sequential light in wavelength ranges different from each other in time series;
a signal processing means provided with a function of processing the signal corresponding to said frame sequential type color imaging means and a function of processing the signal corresponding to a color imaging means provided with a color filter;
a color monitoring means color-displaying predetermined color video signals output from said signal processing means.

5. An endoscope imaging system comprising:
a frame sequential type color imaging means using a solid state imaging device not fitted with a color separating color filter in front of an imaging part having a photoelectric converting function;
a light outputting means for selectively outputting a frame sequential light, in wavelength ranges different form each other in time series, and a white light;
a signal processing means processing the signal corresponding to said frame sequential type color imaging means; and
a color monitoring means color-displaying predetermined color video signals output from said signal processing means.

6. An endoscope imaging system comprising:
a color imaging means provided with a color filter using a solid state imaging device fitted with a color separating color filter in front of an imaging part having a photoelectric converting function;
a frame sequential type color imaging means using a solid state imaging device fitted with a color separating color filter in front of an imaging part having a photoelectric converting function;
a light output means provided with functions corresponding to said color imaging means provided with said color filter and said frame sequential type color imaging means;
a signal processing means provided with functions corresponding to said color imaging means provided with said color filter and said frame sequential type color imaging means;
a color monitoring means color-displaying predetermined color video signals output from said signal processing means; and
a housing means including said light output means and said signal processing means.

7. An endoscope imaging system according to claim 1 wherein said light outputting means is provided with both functions of a white light outputting means outputting a white light and a frame sequential type light outputting means outputting an illuminating light in wavelength ranges different from each other in time series.

8. An endoscope imaging system according to claim 2 wherein said light outputting means has a function of outputting a frame sequential light in wavelength ranges different from each other in time series.

9. An endoscope imaging system according to claim 4 wherein said light outputting means has a function of outputting a white light.

10. An endoscope imaging system according to claim 1 wherein said signal processing means has a function of processing the signal corresponding to said color imaging means provided with said color filter and a function of processing the signal corresponding to said frame sequential type color imaging means.

11. An endoscope imaging system according to any one of claims 2, 3, 5, 9, 7 or 6 wherein an optical endoscope can be fitted to an outputting end of said light outputting means.

12. An endoscope system according to any of claims 2, 4 or 10 wherein said signal processing means has a common signal connector receptacle connectable with signal connectors fitted respectively to said color imaging means provided with said color filter and said frame sequential type color imaging means and said light outputting means has individual light source connector receptacles.

13. An endoscope imaging system according to any of claims 2, 4 or 10 wherein said signal processing means is formed of a first kind signal processing part processing the signal corresponding to said color imaging means provided with said color filter and a second kind signal processing part processing the signal corresponding to said frame sequential type color imaging means.

14. An endoscope system according to claim 13 wherein, of said first kind signal processing part and said second kind signal processing part, one signal processing part can be fitted to the other signal processing part.

15. An endoscope system according to claim 14 wherein a first housing containing said one signal processing part can be fitted to a fitting port provided on a second housing containing said other signal processing part.

16. An endoscope system according to claim 14 wherein said first housing containing said one signal processing part can be fitted to the side of said second housing containing said other signal processing part.

17. An endoscope system according to claim 15 wherein said fitting port is provided on the front surface of said second housing.

18. An endoscope system according to claim 15 herein said fitting port is provided on the back surface of said second housing.

19. An endoscope system according to claim 13 wherein said first kind signal processing part and said second kind signal processing part are contained in the same housing.

20. An endoscope system according to claim 19 wherein said first kind signal processing part and said second kind signal processing part have at least the output end in common.

21. An endoscope system according to claim 19 wherein said first kind signal processing part and said second kind signal processing part output NTSC system color video signals.

22. An endoscope system according to claim 13 wherein said first kind signal processing part and said second kind signal processing part have a common circuit having a part of the formation circuit in common.

23. An endoscope system according to claim 22 wherein said common circuit has a freezing frame memory.

24. An endoscope system according to claim 22 wherein said first kind signal processing part and said second kind signal processing part output NTSC system color video signals.

25. An endoscope imaging system according to any of claims 1, 2, 3 or 6 wherein said color imaging means provided with a color filter is contained in the tip side of an elongate insertable part of an electronic scope.

26. An endoscope imaging system according to any of claims 1, 4, 5 or 6 wherein said frame sequential type color imaging means is contained in the tip side of an elongate insertable part of an electronic scope.

27. An endoscope imaging system according to any of claims 1, 2, 3 or 6 wherein said color imaging means provided with said color filter is contained within a television camera fittable to an eyepiece part of an optical endoscope having an image guide.

28. An endoscope imaging system according to claim 27 wherein said optical endoscope is a fiber scope in which said image guide is formed of a fiber bundle.

29. An endoscope imaging system according to claim 27 wherein said optical endoscope is a rigid endoscope in which said image guide is formed of a relay optical system.

30. An endoscope imaging system according to any of claims 1, 4, 5 or 6 wherein said frame sequential type color imaging means is contained within a television camera fittable to an eyepiece part of an optical endoscope having an image guide.

31. An endoscope imaging system according to claim 30 wherein said optical endoscope is a fiber scope in which said image guide is formed of a fiber bundle.

32. An endoscope imaging system according to claim 30 wherein said optical endoscope is a rigid endoscope in which said image guide is formed of a relay optical system.

33. An endoscope system according to any of claims 1, 2, 3, 4, or 5 wherein said light outputting means and said signal processing means are contained within the same housing.

34. An endoscope system according to any of claims 1, 2, 3, 4 or 5 wherein said light outputting means and said signal processing means are contained respectively within separate housings.

35. An endoscope system according to any of claims 3, 5, 8 or 9 wherein said light outputting means has a common light source connector receptacle outputting selectively said frame sequential light and said white light and said signal processing means has individual signal connector receptacles.

36. An endoscope imaging system according to claim 8 further comprising a frame sequential type color imaging means.

37. An endoscope imaging system according to claim 9 further comprising a color imaging means provided with a color filter.

38. An endoscope system according to claim 36 or 37 wherein said color imaging means provided with said color filter and said frame sequential color imaging means have type signal generating means outputting type signals different from each other.

39. An endoscope system according to claim 38 wherein said light outputting means has a switching means capable of outputting selectively said frame sequential light and said white light.

40. An endoscope imaging system according to claim 39 wherein said signal processing means has a means for discriminating said type signal.

41. An endoscope imaging system according to claim 40 wherein said switching means is switched by the discriminating signal by said type signal discriminating means.

42. An endoscope system according to claim 38 wherein said signal processing means is formed of a first kind signal processing part processing the signal corresponding to said color imaging means provided with said color filter and a second kind signal processing part processing the signal corresponding to said frame sequential type color imaging means.

43. An endoscope system according to claim 42 wherein said signal processing means has a type signal discriminating means.

44. An endoscope system according to claim 43 further comprising a switching means switching selectively said first kind signal processing part and said second kind signal processing part.

45. An endoscope system according to claim 44 wherein said signal type discriminating means discriminates type signals and switches said switching means.

46. An endoscope imaging system according to claim 6, wherein said light outputting means and said signal processing means each having a common light source connector receptacle and a common signal connector receptacle.

47. An endoscope imaging system according to claim 11 wherein said light outputting means outputs a white light when said optical endoscope is fitted to the system.

48. An endoscope imaging system according to claim 6 wherein said light outputting means has a function of outputting a frame sequential light in wavelength ranges different from each other in time series.

49. An endoscope imaging system according to claim 6 wherein said light outputting means has a function of outputting a white light.

50. An endoscope imaging system according to claim 48 further comprising a frame sequential type color imaging means.

51. An endoscope imaging system according to claim 49 further comprising a color imaging means provided with a color filter.

52. An endoscope system according to claims 50 or 51 wherein said color imaging means provided with said color filter and said frame sequential color imaging means have type signal generating means outputting type signals different from each other.

53. An endoscope system according to claim 52 wherein said light outputting means has a switching means capable of outputting selectively said frame sequential light and said white light.

54. An endoscope imaging system according to claim 53 wherein said signal processing means has a means for discriminating said type signal.

55. An endoscope imaging system according to claim 54 wherein said switching means is switched by the discriminating signal by said type signal discriminating means.

56. An endoscope system according to claim 52 wherein said signal processing means is formed of a first kind signal processing part processing the signal corresponding to said color imaging means provided with said color filter and a second kind signal processing part processing the signal corresponding to said frame sequential type color imaging means.

57. An endoscope system according to claim 56 wherein said signal processing means has said type signal discriminating means.

58. An endoscope system according to claim 57 further comprising a switching means switching selectively said first kind signal processing part and said second kind signal processing part.

59. An endoscope system according to claim 58 wherein said signal type discriminating means discriminates type signals and switches said switching means.

60. An endoscope imaging system according to claim 6 wherein said signal processing means is formed of a first kind signal processing part processing the signal corresponding to said color imaging means provided with said color filter and a second kind signal processing part processing the signal corresponding to said frame sequential type color imaging means.

61. An endoscope system according to claim 60 wherein, of said first kind signal processing part and said second kind signal processing part, one signal part can be fitted to the other signal processing part.

62. An endoscope system according to claim 60 wherein said first kind signal processing part and said second kind signal processing part have a common circuit having a part of the formation circuit in common.

63. An endoscope system according to claim 62 wherein said common circuit has a freezing frame memory.

* * * * *